(12) United States Patent
Guettner et al.

(10) Patent No.: US 9,717,791 B2
(45) Date of Patent: Aug. 1, 2017

(54) METHODS OF TREATING PSORIASIS USING IL-17 ANTIBODY

(75) Inventors: Achim Guettner, Binzen (DE); Matthias Machacek, Allschwil (CH); Charis Papavassilis, Loerrach (DE); Oliver Sander, Basel (CH)

(73) Assignee: Novartis AG, Basel (CH)

( * ) Notice: Subject to any disclaimer, the term of this patent is extended or adjusted under 35 U.S.C. 154(b) by 184 days.

(21) Appl. No.: 13/876,367

(22) PCT Filed: Oct. 7, 2011

(86) PCT No.: PCT/EP2011/067522
§ 371 (c)(1),
(2), (4) Date: Mar. 27, 2013

(87) PCT Pub. No.: WO2012/045848
PCT Pub. Date: Apr. 12, 2012

(65) Prior Publication Data
US 2013/0202610 A1 Aug. 8, 2013

(51) Int. Cl.
*A61K 39/395* (2006.01)
*C07K 16/24* (2006.01)
*A61K 39/00* (2006.01)

(52) U.S. Cl.
CPC ........ *A61K 39/3955* (2013.01); *C07K 16/244* (2013.01); *A61K 2039/505* (2013.01); *A61K 2039/545* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,807,155 B2 * | 10/2010 | Di Padova et al. | 424/130.1 |
| 8,119,131 B2 * | 2/2012 | Di Padova et al. | 424/130.1 |
| 2002/0098185 A1 * | 7/2002 | Sims et al. | 424/145.1 |
| 2006/0009385 A1 * | 1/2006 | Hoffman et al. | 514/12 |
| 2010/0003243 A1 * | 1/2010 | Okun et al. | 424/133.1 |

FOREIGN PATENT DOCUMENTS

| | | |
|---|---|---|
| RU | 2341272 C1 | 12/2008 |
| WO | WO 2006/013107 A1 | 2/2006 |
| WO | WO 2007/070750 A1 | 6/2007 |
| WO | WO 2007/149032 A1 | 12/2007 |
| WO | WO 2010/034443 A1 | 4/2010 |

OTHER PUBLICATIONS

Hueber et al. Effects of AIN457, a fully human antibody to interleukin-17A, on psoriasis, rheumatoid arthritis, and uveitis. Sci Transl Med. Oct. 6, 2010;2(52):52ra72.*
Gordon et al. Clinical response to adalimumab treatment in patients with moderate to severe psoriasis: Double-blind, randomized controlled trial and open-label extension study. J Am Acad Dermatol. Oct. 2006;55(4):598-606.*
Menter et al. Adalimumab therapy for moderate to severe psoriasis: A randomized, controlled phase III trial. J Am Acad Dermatol. Jan. 2008;58(1):106-15. Epub Oct. 23, 2007.*
Clinical trial NCT01406938, Jul. 12, 2011.*
Reich et al. Improvement in quality of life with infliximab induction and maintenance therapy in patients with moderate-to-severe psoriasis: a randomized controlled trial. Br. J Dermatol. Jun. 2006;154(6):1161-8.*
Clinical trial NCT00941031, Jun. 16, 2009.*
M.F. Haller, Converting Intravenous Dosing to Subcutaneous Dosing With Recombinant Human Hyaluronidase. Pharmaceutical Technology, Oct. 2, 2007.*
Boffa et al. Methotrexate for psoriasis. Clin Exp Dermatol. Nov. 1996;21(6):399-408.*
NHSC publication—Secukinumab for plaque psoriasis (Apr. 2012).*
Clinical trial 2008-007525-39, Jun. 9, 2009 (https://www.clinicaltrialsregister.eu/ctr-search/trial/2008-007525-39/DE#A).*
Clinical trial NCT01071252, Feb. 18, 2010.*
Mrowietz et al. (2013) "Secukinumab 'fixed-interval' versus 'retreatment-as-needed' regimen for moderate-to-servere plaque psoriases: A study comparing secukinumab use in long-term psoriais maintenance therapy (SCULPTURE)" Presented Oct. 3, 2013 at EADV conference held Oct. 2-6, 2013, Istanbul, Turkey.
Langley et al (2013) "Secukinumab Compared With Placebo and Etancercept: A Head-to-Head Comparison of Two Biologies in a Phase 3 Study of Moderate-to-Severe Plaque Psoriasis (FIXTURE)" Presented Oct. 3, 2013 at EADV conference held Oct. 2-6, 2013, Istanbul, Turkey.
Feldman S Advances in psoriasis treatment. Dermatol Online J 2000;6:4.
Hueber W et al, "Effects of AIN457, a Fully Human Antibody to Interleukin-17A, on Psoriasis, Rheumatoid Arthritis, and Uveitis", Database Biosis, Biosciences Information Service, Database accession No. PREV201100223273, abstract, Oct. 6, 2010. [XP002666877].
"A Multicenter Extension Trial of Subcutaneously Administered AIN547 in Patients With Moderate to Severe Chronic-Plaque Type Psoriasis", Clinical Trial Identifier: NCT01132612, Updated: May 27, 2010, ClinicalTrials.gov archive; Title: NCT01132612 on May 27, 2010, available at http://clinicaltrials.gov/archive/NCT01132612/2010_05_27, May 27, 2010.
MacDonald and Burden, "Psoriasis: advances in pathophysiology and management", (2007),Postgrad Med. J. 83:690-697.
Miller, Tamera, "Intense focus on a molecule called IL-17 could unlock the door to more psoriasis treatments", (2012) in Medicine of the Future, available at http://www.psoriasis.org/advance/features/interleukin-17-could-unlock-psoriasis-treatments Downloaded Jun. 3, 2014.
Lalonde et al., "Model-based Drug Development", (2007), Clin. Pharm. & Ther. 82:21-32.
Recker et al., "Insufficiently dosed intravenous ibandronate injections are associated with suboptimal antifracture efficacy in postmenopausal osteoporosis", (2004), Bone 34(5):890-898.

(Continued)

Primary Examiner — Vanessa L Ford
(74) Attorney, Agent, or Firm — Leslie Fischer

(57) ABSTRACT

The disclosure relates to novel regimens for treating psoriasis, which employ a therapeutically effective amount of an IL-17 antagonist, e.g., an IL-17 binding molecule, e.g., an IL-17 antibody, such as the secukinumab antibody, or an IL-17 receptor binding molecule, e.g., an IL-17 receptor antibody.

14 Claims, 11 Drawing Sheets

(56) References Cited

OTHER PUBLICATIONS

Zhao et al., "Clinical pharmacology considerations in biologics development", (2012) Acta Pharm. Sinica 33:1339-1347.
Kagan et al., "Subcutaneous Absorption of Monocolonal Antibodies : Role of Dose. Site of Injection, and Injection Volume on Rituximab Pharmacokinetics in Rats", (2012), Pharm. Res. 29:490-99.
Porter, "Lymphatic Transport of Proteins After Subcutaneous Administration", (2000), J. Pharm. Sci. 89:297-310.
Haller, Michael F., "Converting Intravenous Dosing to Subcutaneous Dosing With Recombinant Human Hyaluronidase", (2007), in Pharmaceutical Technology, available at http://license.icopyright.net/user/viewFreeUse.act?fuid=MTc5NzkxMTQ%3D Downloaded Mar. 26, 2014.
De Cesare, Antonella, "The IL-23/Th17 Axis in the Immunopathogenesis of Psoriasis", (2009), J. Invest. Dermatol. 129: 1339-1350.
Clark, Rachel, A., "Skin-Resident T Cells: The Ups and Downs of On Site Immunity", (2010), J. Invest. Derm. 130 362-370.
Kagami et al., "Circulation Th17, Th22, and Th1 Cells Are Increased in Psoriasis", (2010) J. Invest. Dermatol 130: 1373-1383.
Zhang et al., "Increased Th17 cells are accompanied by FoxP3+ treg cell accumulation and correlated with psoriasis disease severity", (2010), Clin. Immunol. 136:108-117.
African et al., "Serum Levels of TNF-α, IFN-γ, IL-6, IL-8, IL-12, IL-17, and IL-18 in Patients With Active Psoriasis and Correlation With Disease Severity", (2005), Mediators Inflamm. 2005:273-279.
Takahashi et al., "Serum cytokines and growth factor levels in Japanese patients with psoriasis", (2010), Clin. Exp. Dermatol. 35:645-649.
Caproni et al., "Serum Levels of IL-17 and IL-22 Are reduced by Etanercept, but not by Acitretin, in Patients with Psoriasis: a Randomized-Controlled Trial", (2009), J. Clin. Immunol. 29-210-4.
Lynde et al., "Interleukin 17A: Toward a new understanding of psoriasis pathogenesis", (2014), J. Am. Acad. Dermatol Published on line Mar. 18, 2014, available at http://dx.doi.org.10.1016/j.jaad.2013.12.036.
Coimbra et al., "Interleukin (IL)-22, IL-23, IL-8, vascular endothelial growth factor and tumor necrosis factor-α levels in patients with psoriasis before, during, and after psoralen-ultraviolet A and narrowband ultraviolet B therapy", (2010), Br. J. Dermatol. 163:1282-90.
Jancin, Bruce, "Secukinumab soars in phase III psoriasis studies", (2013) in Skin & Allergy News; available at http://www.skinandallergynews.com/single-view/secukinumab-soars-in-phase-iii-psoriasis-studies/dd37980df8cdc76b3aaf6a3aded3c867.html Downloaded Apr. 29, 2014.
Sacks et al., "Scientific and Regulatory Reasons for Delay and Denial of FDA Approval of Initial Applications for New Drugs, 2000-2012", (2014), JAMA 311:378-84.
Richter et al., "Mechanistic Determinates of Biotherapeutics Absorption Following SC Administration", (2012), AAPS Journal 14 :559-570.
Porter et al., "Lymphatic transport of proteins after s.c injection: implications of animal model selection", (2001), Adv. Drug. Delivery Reviews 50:157-171.
Wang et al., "Monoclonal Antibody Pharmacokinetics and Pharmacodynamics", (2008) Clin Pharmacol Ther. 84(5):548-58.
Mortensen et al., "Pharmacokinetics and Parmacodynanimcs of Multiple Weekly Subcutaneous Elazumab Doses in Patients With Plaque Psoriasis", (2005) J. Clin. Pharmacol. 45:286-98.
Dayneka et al., "Comparison of Four Basic Models of Indirect Pharmacodynamic responses", J Pharacokinetics and Biopharmaceutics, vol. 21, No. 4, pp. 457-478, (1993).
Lalonde et al., "Model-based Drug Development", Clinical Pharmacology & Therapeutics, vol. 82, No. 1, pp. 21-32, (Jul. 2007).
Hutmacher et al., "Modeling of the Exposure-Response Relationship of Etanercept in the Treatment of Patients With Chronic Moderate to Severe Plaque Psoriasis", J Clin Pharmacol, vol. 47, pp. 238-248, (2007).
Wyatt, Nicole, "New psoriasis drug shows potential in UAB-led phase III trial", UAB News, Jul. 16, 2014, [downloaded from https://www.uab.edu/news/innovation/item/4964-new-psoriasis-drug-shows-potential-in- . . . Dec. 10, 2014 downloaded Dec. 10, 2014].
Osterwil, Neil, "Experimental Secukinumab Clears Psoriasis in Some Patients", Medscape, Jul. 11, 2014 [Downloaded from http://medscape.com/viewarticle/828178 downloaded on Dec. 10, 2014].
Novartis AG, "Head-to-head psoriasis study demonstrates superiority of Novartis Cosentyx to Stelara in clearing Skin", Dec. 12, 2014 [Downloaded from http://www.novartis.com/newsroom/media-releases/en/2014/1879309.shtml].
Jancin, (Oct. 24, 2013) "Is PASI 90 Becoming the New PASI 75?"available at http://www.edermatologynews.com/single-article-page/is-pasi-90-becoming-the-new-pasi-75/8bb5e809073c6bc522fadaf91946006e.html.
Seston et al., "Balancing the Benefits and Risks of Drug Treatment", Arch. Dermatol, vol. 143, No. 9, pp. 1175-1179, (2007).
Christophers et al., "The unmet treatment need for moderate to severe psoriasis: results of a survey and chart review", JEADV, vol. 20, pp. 921-925, (2006).
Christophers et al., "Clinical improvement and satisfaction with biological therapy in patients with severe plaque psoriasis: results of a European cross-sectional observational study", J. of Derm. Treatment, vol. 24, pp. 193-198, (2013).
Stern et al., Psoriasis Is Common, Carries a Substantial Burden Even When Not Extensive, and Is Associated with Widespread Treatment Dissatisfaction, J Investig Dermatol Symp Proc, vol. 9, pp. 136-139, (2004).
Search of https://www.clinicaltrialsregister.eu/ for "AIN457 or secukinumab" performed Feb. 4, 2015.
"Pharmaceuticals: today, the EU Register of Clinical Trials is launched Online", dated Mar. 22, 2011 available at http://europa.eu/rapid/press-release IP-11-339 en.htm.
"Frequently Asked Questions, EU Clinical Trials Register", available at http://www.pei.de/SharedDocs/Downloads/EN/pu/clinical-trials/faq-eu-clinical-trials-register.pdf?blob=publicationFile&v=1, downloaded Mar. 3, 2015.
Papp et al., "Secukinumab, a novel fully human antibody to interieukin-17A, in the treatment of moderate-to-severe plaque psoriasis: Efficacy and safety interim results from a phase II intravenous induction dose-ranging study" Abstract No. 0630, Presented at the 20th Congress of the European Academy of Dermatology and Venereology (EADV) Oct. 20-24, 2011, Lisbon, Portugal.
Bastick, Jan. 23, 2015 "FDA approves secukinumab for moderate-to-severe plaque psoriasis", available at: http://formularyjournal.modernmedicine.com/.
Walsh, Jul. 9, 2014 "Novel Antibody Obliterates Psoriasis" available at: http://www.medpagetoday.com/Dermatology/Psoriasis/46691.
Worchester, Feb. 27, 2015 "New psoriasis drugs offer treatment advantages" available at: http://www.rheumatologynews.com/.
Blauvet et al., "Secukinumab Treatment Maintains Efficacy in Moderate to Severe Plaque Psoriasis With Monthly Dosing Through a Second Year of Treatment: A Randomized Extension of the ERASURE and FIXTURE Studies" Abstract presented at 2015 Annual Meeting American Academy of Dermatology, held San Francisco, Mar. 20-24, 2015.
Thaci et al., "Secukinumab is superior to ustekinumab in clearing skin of subjects with moderate to severe plaque psoriasis: 16-week results from the clear study" Abstract presented at 2015 Annual Meeting American Academy of Dermatology, held San Francisco, Mar. 20-24, 2015.
Rich at al "Secukinumab induction and maintenance therapy in moderate-to-severe plaque psoriasis: a randomized, double-blind, placebo-controlled, phase II regimen-finding study" Br J Dermatol. Feb. 2013;168(2):402-11.
Papp at al "Efficacy and safety of secukinumab in the treatment of moderate-to-severe plaque psoriasis: a randomized, double-blind, placebo-controlled phase II dose-ranging study." Br J Dermatol Feb. 2013:168(2):412-21.

(56) References Cited

OTHER PUBLICATIONS

Paul et al., "Secukinumab improves hand, foot and nail lesions in moderate-to-severe plaque psoriasis: subanalysis of a randomized, double-blind, placebo-controlled, regimen-finding phase 2 trial" J Eur Acad Dermatol Venerol. Dec. 2014;28(12),1670-5.
Blauvet et al., (Mar. 20, 2015) "Secukinumab Treatment Maintains Efficacy in Moderate to severe Plaque Psoriasis Through Second Year of Treatment. A Randomized Extension of the ERASURE and FIXTURE Studies" delivered at American Academy of Dermatology annual meeting San Francisco, Mar. 20, 2015.
Thaci et al. (Mar. 30, 2015) "Secukinumab Is Superior to Ustekinumab in Clearing Skin of Subjects With Moderate to Severe Plaque Psoriasis: 16-Week Results From the Clear Study" delivered at American Academy of Dermatology annual meeting San Francisco, Mar. 20, 2015.
Walsh, Jan. 21, 2015 "Cosentyx gets FDA nod for Psoriasis" available at: http://www.medpagetoday.com/Dermatology/Psoriasis/46691.
TrialTroveID 043947 publication updated May 31, 2014, available at http://novartis.citeline.com/search.asp?#.
TrialTrove ID 076073 publication updated Jan. 23, 2015, available at http://novartis.citeline.com/search.asp?#.
TrialTrove ID 081770 publication updated May 20, 2013, available at http://novartis.citeline.com/search.asp?#.
TriaiTrove ID 086003 publication updated Sep. 16, 2014, available at http://novartis.citeline.com/search.asp?#.
TrialTrove ID 101212 publication updated Jun. 10, 2014, available at http://novartis.citeline.com/search.asp?#.
TrialTrove ID 101213 publication updated Sep. 27, 2013, available at http://novartis.citeline.com/search.asp?#.
TrialTrove ID 101786, publication updated Jan. 23, 2015, available at http://novartis.citeline.com/search.asp?#.
TrialTrove ID 102154, publication updated May 17, 2014, available at http://novartis.citeline.com/search.asp?#.
TrialTrove ID 111067, publication updated Oct. 6, 2014, available at http://novartis.citeline.com/search.asp?#.
TrialTrove ID 111963, pubication updated Jan. 23, 2015, available at http://novartis.citeline.com/search.asp?#.
TrialTrove ID 111976, publication updated Nov. 8, 2011, available at http://novartis.citeline.com/search.asp?#.
TrialTrove ID 117251, publication updated Sep. 12, 2014, available at http://novartis.citeline.com/search.asp?#.
TrialTrove ID 118356, publication updated Sep. 11, 2014, available at http://novartis.citeline.com/search.asp?#.
TrialTrove ID 123037, publication updated Jan. 23, 2015, available at http://novartis.citeline.com/search.asp?#.
TrialTrove ID 126068, publication updated Dec. 19, 2014, available at http://novartis.citeline.com/search.asp?#.
TrialTrove ID 128101, publication updated Sep. 29, 2014, available at http://novartis.citeline.com/search.asp?#.
TrialTrove ID 128557, publication updated Jan. 23, 2015, available at http://novartis.citeline.com/search.asp?#.
TrialTrove ID 128645, publication updated Feb. 2, 2015, available at http://novartis.citeline.com/search.asp?#.
TrialTrove ID 131793, publication updated Dec. 23, 2013, available at http://novartis.citeline.com/search.asp?#.
TrialTrove ID 138695, publication updated Jan. 10, 2013, available at http://novartis.citeline.com/search.asp?#.
TrialTrove ID 146855, publication updated Jan. 21, 2015, available at http://novartis.citeline.com/search.asp?#.
TrialTrove ID 147040, publication updated Nov. 14, 2014, available at http://novartis.citeline.com/search.asp?#.
TrialTrove ID 147500, publication updated Dec. 30, 2014 available at http://novartis.citeline.com/search.asp?#.
TrialTrove ID 147571, publication updated Jan. 23, 2015, available at http://novartis.citeline.com/search.asp?#.
TrialTrove ID 148447, publication updated Feb. 2, 2015, available at http://novartis.citeline.com/search.asp?#.
TrialTrove ID 150779, publication updated Jan. 23, 2015, available at http://novartis.citeline.com/search.asp?#.
TrialTrove ID 151251, publication updated Jan. 23, 2015 available at http://novartis.citeline.com/search.asp?#.
TrialTrove ID 152134, publication updated Aug. 13, 2014, available at http://novartis.citeline.com/search.asp?#.
TrialTrove ID 152773, publication updated Dec. 4, 2013, available at http://novartis.citeline.com/search.asp?#.
TrialTrove ID 152884, publication updated Sep. 17, 2014, available at http://novartis.citeline.com/search.asp?#.
TrialTrove ID 157295, publication updated Dec. 4, 2014, available at http://novartis.citeline.com/search.asp?#.
TrialTrove ID 162826, publication updated Jan. 22, 2015, available at http://novartis.citeline.com/search.asp?#.
TrialTrove ID 163005, publication updated Sep. 8, 2014, available at http://novartis.citeline.com/search.asp?#.
TrialTrove ID 163568, publication updated Feb. 4, 2015, available at http://novartis.citeline.com/search.asp?#.
TrialTrove ID 163991, publication updated Jan. 23, 2015, available at http://novartis.citeline.com/search.asp?#.
TrialTrove ID 170947, publication updated Jan. 23, 2015, available at http://novartis.citeline.com/search.asp?#.
TrialTrove ID 171256, publication updated Oct. 22, 2014, available at http://novartis.citeline.com/search.asp?#.
TrialTrove ID 171269, publication updated Feb. 2, 2015, available at http://novartis.citeline.com/search.asp?#.
TrialTrove ID 171802, publication updated Nov. 26, 2014, available at http://novartis.citeline.com/search.asp?#.
TrialTrove ID 175435, publication updated Feb. 2, 2015, available at http://novartis.citeline.com/search.asp?#.
TrialTrove ID 179377, publication updated Dec. 30, 2014, available at http://novartis.citeline.com/search.asp?#.
TrialTrove ID 182998, publication updated Jan. 23, 2015, available at http://novartis.citeline.com/search.asp?#.
TrialTrove ID 183013, publication updated Nov. 25, 2014, available at http://novartis.citeline.com/search.asp?#.
TrialTrove ID 184542, publication updated Nov. 10, 2014, available at http://novartis.citeline.com/search.asp?#.
TrialTrove ID 187318, publication updated Dec. 5, 2014, available at http://novartis.citeline.com/search.asp?#.
TrialTrove ID 188301, publication updated Sep. 6, 2014, available at http://novartis.citeline.com/search.asp?#.
TrialTrove ID 189840, publication updated Jan. 22, 2015, available at http://novartis.citeline.com/search.asp?#.
TrialTrove ID 190419, publication updated Jun. 10, 2014, available at http://novartis.citeline.com/search.asp?#.
TrialTrove ID 190457, publication updated Feb. 2, 2015, available at http://novartis.citeline.com/search.asp?#.
TrialTrove ID 194579, publication updated Jan. 31, 2015, available at http://novartis.citeline.com/search.asp?#.
TrialTrove ID 195065, publication updated Oct. 9, 2013, available at http://novartis.citeline.com/search.asp?#.
TrialTrove ID 195312, publication updated Oct. 2013, available at http://novartis.citeline.com/search.asp?#.
TrialTrove ID 197625, publication updated Jan. 16, 2015, available at http://novartis.citeline.com/search.asp?#.
TrialTrove ID 198998, publication updated Feb. 4, 2015, available at http://novartis.citeline.com/search.asp?#.
TrialTrove ID 199025, publication updated Nov. 20, 2014, available at http://novartis.citeline.com/search.asp?#.
TrialTrove ID 199854, publication updated Dec. 15, 2014, available at http://novartis.citeline.com/search.asp?#.
TrialTrove ID 201436, publication updated Jun. 25, 2014, available at http://novartis.citeline.com/search.asp?#.
TrialTrove ID 210649, publication updated Dec. 17, 2014, available at http://novartis.citeline.com/search.asp?#.
TrialTrove ID 218983, publication updated Dec. 12, 2014, available at http://novartis.citeline.com/search.asp?#.
TrialTrove ID 221001, publication updated Nov. 21, 2014, available at http://novartis.citeline.com/search.asp?#.
TrialTrove ID 251464, publication updated Feb. 3, 2015, available at http://novartis.citeline.com/search.asp?#.
TrialTrove ID 253309, publication updated Mar. 17, 2015, available at http://novartis.citeline.com/search.asp?#.

(56) References Cited

OTHER PUBLICATIONS

TrialTrove ID 253310, publication updated Mar. 7, 2015, available at http://novartis.citeline.com/search.asp?#.
TrialTrove ID NCT00685399, publication updated Nov. 18, 2013, available at http://novartis.citeline.com/search.asp?#.
TrialTrove ID NCT00995709, publication updated Nov. 6, 2014, available at http://novartis.citeline.com/search.asp?#.
TrialTrove ID NCT01032915, publication updated Feb. 14, 2013, available at http://novartis.citeline.com/search.asp?#.
TrialTrove ID NCT01090310, publication updated Jul. 25, 2013, available at http://novartis.citeline.com/search.asp?#.
TrialTrove ID NCT01093846, publication updated May 2, 2012, available at http://novartis.citeline.com/search.asp?#.
TrialTrove ID NCT01095250, publication updated May 2, 2012, available at http://novartis.citeline.com/search.asp?#.
TrialTrove ID NCT01103024, publication updated May 2, 2012, available at http://novartis.citeline.com/search.asp?#.
TrialTrove ID NCT01327664, publication updated Dec. 5, 2013, available at http://novartis.citeline.com/search.asp?#.
TrialTrove ID NCT01364389, publication updated Mar. 12, 2013, available at http://novartis.citeline.com/search.asp?#.
Dick et al. (2013) Opthalmology 120(4) p. 777.
Clinical Trial NCT00584740 publication dated Jan. 1, 2008, available at http://clinicaltrials.gov.
Clinical Trial NCT00584740 publication dated Sep. 7, 2010, available at http://clinicaltrials.gov.
Clinical Trial NCT00669916 publication dated Apr. 30, 2008, available at http://clinicaltrials.gov.
Clinical Trial NCT00669916 publication dated Dec. 15, 2008 available at http://clinicaltrials.gov.
Clinical Trial NCT00669942 publication dated Apr. 30, 2008, available at http://clinicaltrials.gov.
Clinical Trial NCT00669942 publication dated Sep. 20, 2010, available at http://clinicaltrials.gov.
Clinical Trial NCT00685399 publication dated May 27, 2008, available at http://clinicaltrials.gov.
Clinical Trial NCT00685399 publication dated Mar. 9, 2010, available at http://clinicaltrials.gov.
Clinical Trial NCT00770965 publication dated Oct. 9, 2008, available at http://clinicaltrials.gov.
Clinical Trial NCT00770965 publication dated Jun. 1, 2009 available at http://clinicaltrials.gov.
Clinical Trial NCT00805480 publication dated Dec. 8, 2008, available at http://clinicaltrials.gov.
Clinical Trial NCT00805480 publication dated Aug. 24, 2009, available at http://clinicaltrials.gov.
Clinical Trial NCT00809159 publication dated Dec. 16, 2008, available at http://clinicaltrials.gov.
Clinical Trial NCT00809159 publication dated Jun. 22 2010, available at http://clinicaltrials.gov.
Clinical Trial NCT00809614 publication dated Dec. 16, 2008, available at http://clinicaltrials.gov.
Clinical Trial NCT00809614 publication dated Apr. 29, 2010, available at http://clinicaltrials.gov.
Clinical Trial NCT00920933 publication dated Jun. 13, 2009, available at http://clinicaltrials.gov.
Clinical Trial NCT00920933 publication dated Apr. 8, 2010, available at http://clinicaltrials.gov.
Clinical Trial NCT00928512 publication dated Jun. 25, 2009, available at http://clinicaltrials.gov.
Clinical Trial NCT00928512 publication dated Mar. 12, 2010, available at http://clinicaltrials.gov.
Clinical Trial NCT00936585 publication dated Jul. 9, 2009, available at http://clinicaltrials.gov.
Clinical Trial NCT00936585 publication dated Sep. 17, 2010, available at http://clinicaltrials.gov.
Clinical Trial NCT00941031 publication dated Jul. 16, 2009, available at http://clinicaltrials.gov.
Clinical Trial NCT00941031 publication dated Feb. 2, 2010, available at http://clinicaltrials.gov.
Clinical Trial NCT00995709 publication dated Oct. 14, 2009, available at http://clinicaltrials.gov.
Clinical Trial NCT00995709 publication dated May 26, 2010, available at http://clinicaltrials.gov.
Clinical Trial NCT01009281 publication dated Nov. 5, 2009, available at http://clinicaltrials.gov.
Clinical Trial NCT01009281 publication dated Sep. 7, 2010, available at http://clinicaltrials.gov.
Clinical Trial NCT01032915 publication dated Dec. 15, 2009, available at http://clinicaltrials.gov.
Clinical Trial NCT01032915 publication dated Aug. 2, 2010, available at http://clinicaltrials.gov.
Clinical Trial NCT01051817 publication dated Aug. 24, 2010, available at http://clinicaltrials.gov.
Clinical Trial NCT01090310 publication dated Mar. 18, 2010 available at http://clinicaltrials.gov.
Clinical Trial NCT01090310 publication dated Sep. 28, 2010, available at http://clinicaltrials.gov.
Clinical Trial NCT01093846 publication dated Mar. 25, 2010, available at http://clinicaltrials.gov.
Clinical Trial NCT01095250 publication dated Mar. 29, 2010, available at http://clinicaltrials.gov.
Clinical Trial NCT01095250 publication dated Sep. 29, 2010, available at http://clinicaltrials.gov.
Clinical Trial NCT01103024 publication dated Apr. 12, 2010, available at http://clinicaltrials.gov.
Clinical Trial NCT01109940 publication dated Apr. 22, 2010, available at http://clinicaltrials.gov.
Clinical Trial NCT01109940 publication dated Jun. 22, 2010, available at http://clinicaltrials.gov.
Clinical Trial NCT01132612 publication dated May 27, 2010, available at http://clinicaltrials.gov.
Clinical Trial NCT01169844 publication dated Jul. 23, 2010, available at http://clinicaltrials.gov.
Letko et al, "IV Secukinumab is an Effective Treatment in Patients With Noninfectious Uveitis Requiring Steroid Sparing Immunosuppressive Therapy", Invest Ophthalmol Vis Sci;54: E-Abstract 5929, (2013) [http://abstracts.iovs.org/cgi/content/abstract/54/6 15929 downloaded Aug. 14, 2014].
Dick et al., "Secukinumab in the Treatment of Noninfectious Uveitis: result of Three Randomized Controlled Clinical Trials", Ophthalmology, vol. 120, No. 4, pp. 777-787, (2013).
Buggage et al., "The Study of IL-17A Expression as a Biomarker for Patients With Active Noninfectious Uveitis Treated With AIN457", Assoc for Research in Vision and Ophthalmology, abstract 3799/D1066, Session 383, Presented May 4, 2010, (2010).
Langley RG, Elewski BE, Lebwohl M, et al., "Secukinumab in plaque psoriasis: results of two phase three trials", N Engl J Med., vol. 371, No. 4 pp. 326-338, Jul. 9, 2014.
Blauvelt A, Prinz J, Gottlieb AB, et al., "Secukinumab Administration by Pre-filled Syringe: Efficacy, Safety, and Usability Results from a Randomized Controlled Trial in Psoriasis (FEATURE)", Br J Dermatol., 2014; [published online ahead of print Aug. 16, 2014].
Paul C, Lacour JP, Tedremets L, et al., "Efficacy, safety, and usability of secukinumab administration by autoinjector/pen in psoriasis: a randomized, controlled trial (JUNCTURE)", J Eur Acad Dermatol Venereol., 2014; [published online ahead of print Sep. 22, 2014].
Media Release, "Novartis Cosentyx receives positive CHMP opinion for first-line treatment of moderate-to-severe psoriasis patients", Nov. 21, 2014. [Downloaded Dec. 2, 2014 at http://multimediacapsule.thomsonone.com/file/download/2049/FullPressRelease/1266].
Declaration of Dr. Wolfgang Hueber, dated Dec. 18, 2015.
Cirriculum Vitae of Dr. Wolfgang Hueber, effective May 27, 2009, Appendix A to Declaration of Dr. Hueber.
NCT00669916 clinicatltrials.gov archive database entry, dated Apr. 30, 2008, Appendix B to Declaration of Dr. Hueber.
Hueber (2010), Sci Transl Med 2, Appendix C to Declaration of Dr. Hueber.
Cumming et al. (2007), Journal of Cell Biology, 177:7-11, Appendix D to Declaration of Dr. Hueber.

(56) References Cited

OTHER PUBLICATIONS

GraphPad—FAQ 1362—What you can conclude when two error bars overlap (or don't), last modified Apr. 22, 2020, available at http://www.graphpad.com/support/faqid/1362/, Appendix E to Declaration of Dr. Hueber.
Gordon KB et al., "Clinical response in psoriasis patients discontinued from and then reinitiated on etanercept therapy", Journal of Dermatology Treatment, 17(1):9-17;2006.
Brezinsky EA et al., Off-label biologic regimens in psoriasis: a systemactic review on efficacy and safety of dose escalation, reduction, and interrupted biological therapy, PLoS ONE, 7(4):e33486, Apr. 11, 2012.
Sandborn and Hanauer, "Infliximab in the Treatment of Crohn's Disease: A User's Guide for Clinicians", Am. J. Gastroenterol., vol. 97, No. 12, pp. 2962-2972, 2002.
Reich et al., "Infliximab induction and maintenance therapy for moderate-to-severe psoriasis: a phase III, multicentre, double-blind trial", Lancet, vol. 366, No. 9494, pp. 1367-1374, 2005.
Menter et al., "A randomized comparison of continuous vs. intermittent infliximab maintenance regimens over 1 year in the treatment of moderate-to-severe plaque psoriasis", J. Am. Acad. Dermatol., vol. 56, No. 1, pp. 31.e1-31.e15, 2007.
Armstrong et al JAMA Dermatol. 2013;149(10):1180-1185.
Dauden et al Actas Dermosifiliogr. 2011;102(4):270-276.
Renzi et al British Journal of Dermatology 2001;145:617±623.
van Cranenburgh et al British Journal of Dermatology 2013;169:398-405.
Bissonette et al. Late breaker abstract presented at EADV, Copenhagen Oct. 7-11, 2015.
Al-Suwaidan and Feldman, J Am Acad Dermatol 2000;42:796-802.
Arican et al. Mediators of Inflammation, 2005;5:273-279.
Bowman et al. J Am Acad Dermatol. 2001;45(3):476.
Fossiez et al. J. Exp. Med. 1996;183:2593-2603.
David Grainger, Forbes online, Dec. 15, 2014, available at: http://onforb.es/1yS9HPo.
Kumar et al. et al. J. Acad. Dermatol 2001;45:153.
Ian Lang, Nature World Report online, Jun. 29, 2015, available at: http://www.natureworldreport.com/2015/06/novartis-bullish-on-prospects-for-psoriasis-drug-cosentyx/.
Mattei et al. JEADV 2014;28:333-337.
Thaci et al. J. Am. Acad. Dermatol. 2015;73:400-409.
Revicki et al. Dermatology 2008;216:260-270.
Mould and Sweeney, Curr. Opin. Drug Discovery & Dev. 2007;10(1):84-96.
Iskar et al. (2010) PloS Compt. Biol. 6(9):1-8.
Declaration of Dr. Mark Lebwohl, including Exhibits A-G, dated Oct. 6, 2015.
Declaration of Dr. Oliver Sander, including Exhibits A-K, dated Oct. 19, 2015.
Declaration of Dr. Charis Papavassilis, including Exhibits A-I, dated Oct. 26, 2015.
WHO Drug Information, "International Nonproprietary Names for Pharmaceutical Substances (INN)", vol. 24, No. 3, pp. 259-290, 2010.
Registry entry 1229022-83-6 downloaded Apr. 10, 2016.
Kubanova A.A. et al., "Immune mechanisms of psoriasis. New strategies of biological therapy/", Vestnik dermatologii i venerologii., 2010, No. 1, pp. 35-47, found Sep. 11, 2015 on the Internet: http://www.vestnikdv.ru/archive/10_01_07.pdf; (English Abstract).

* cited by examiner

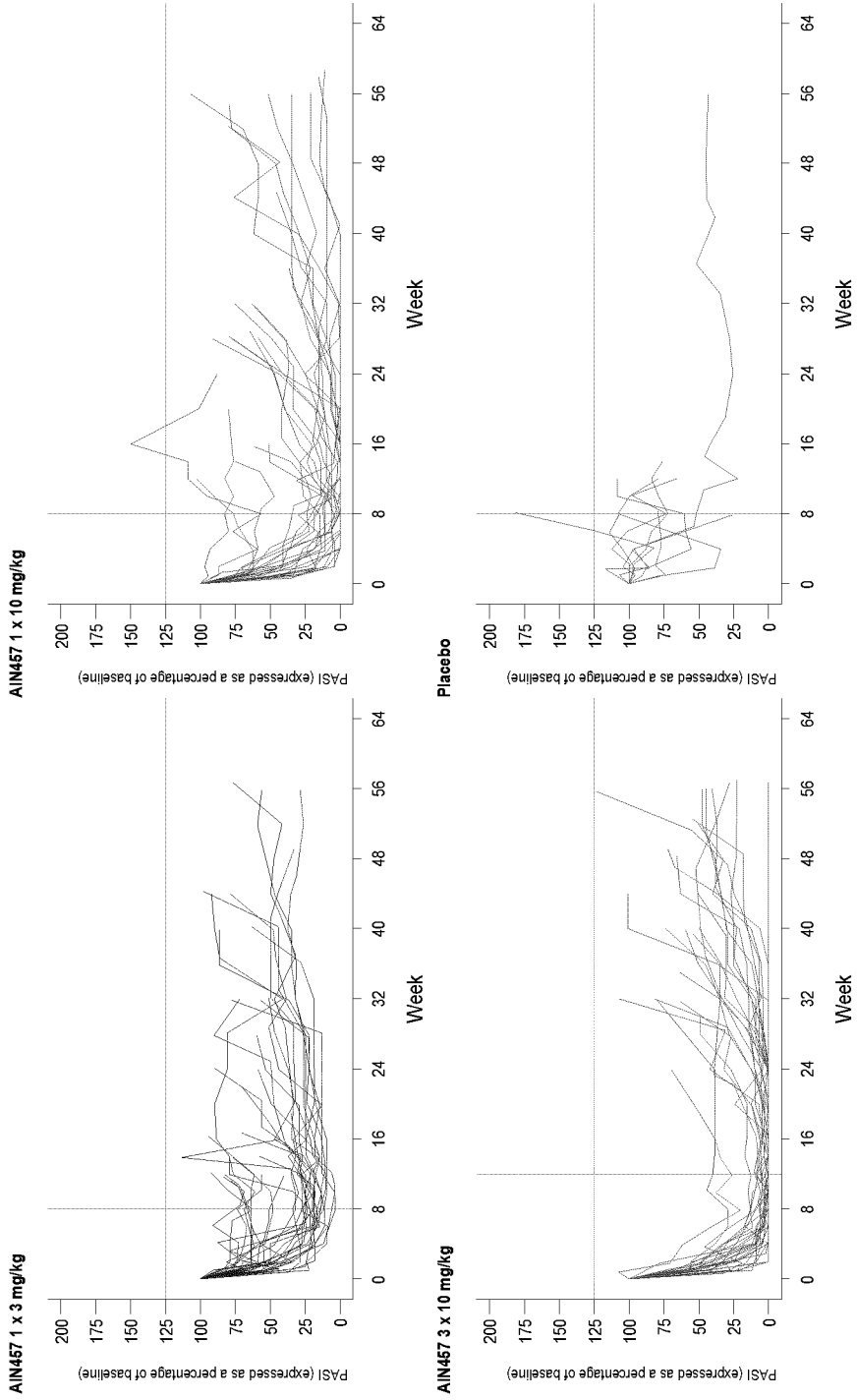
Figure 1: No rebound is observed in secukinumab-treated patients within 8 weeks after dosing.

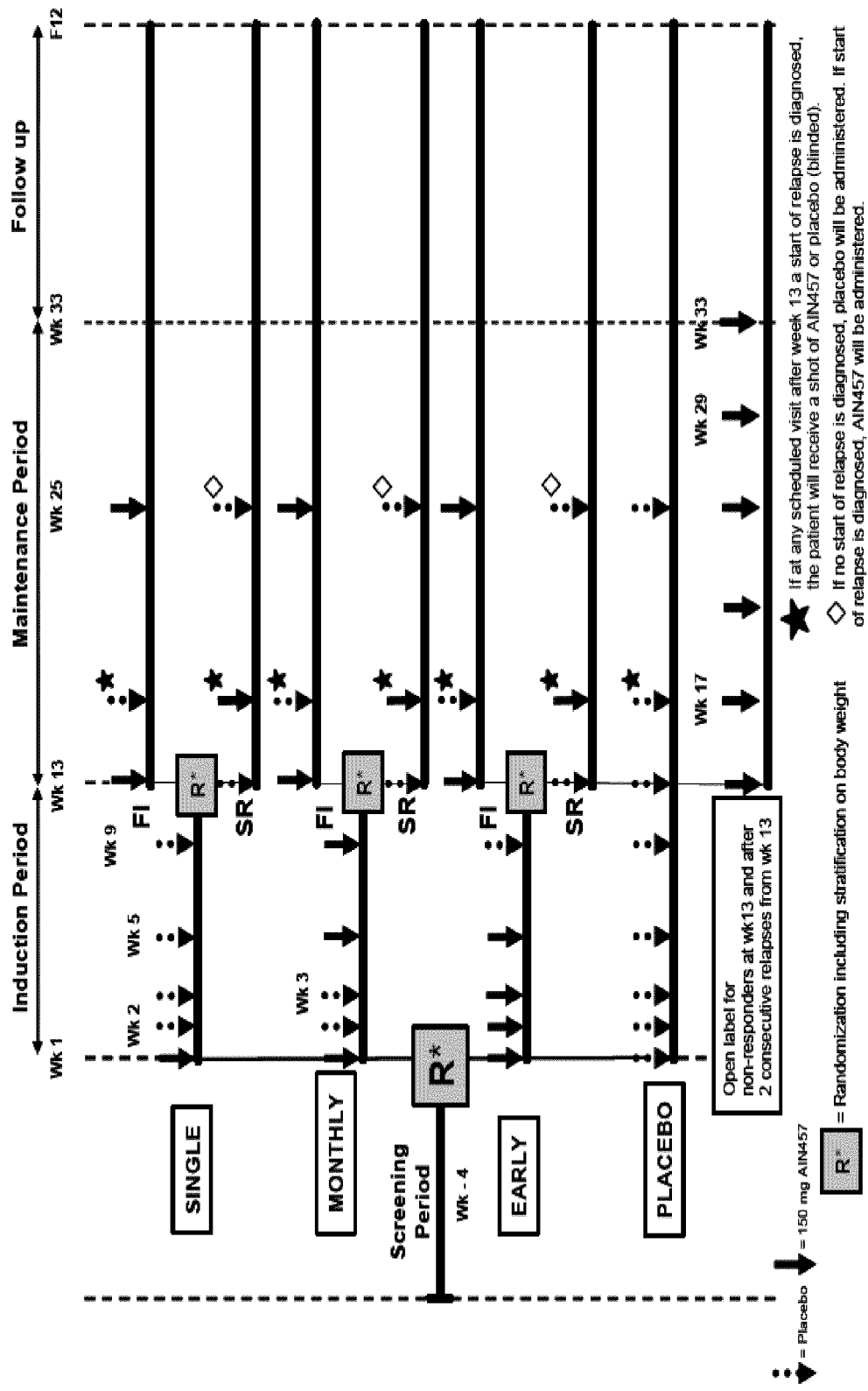
Figure 2: CAIN457A2211 Study Design

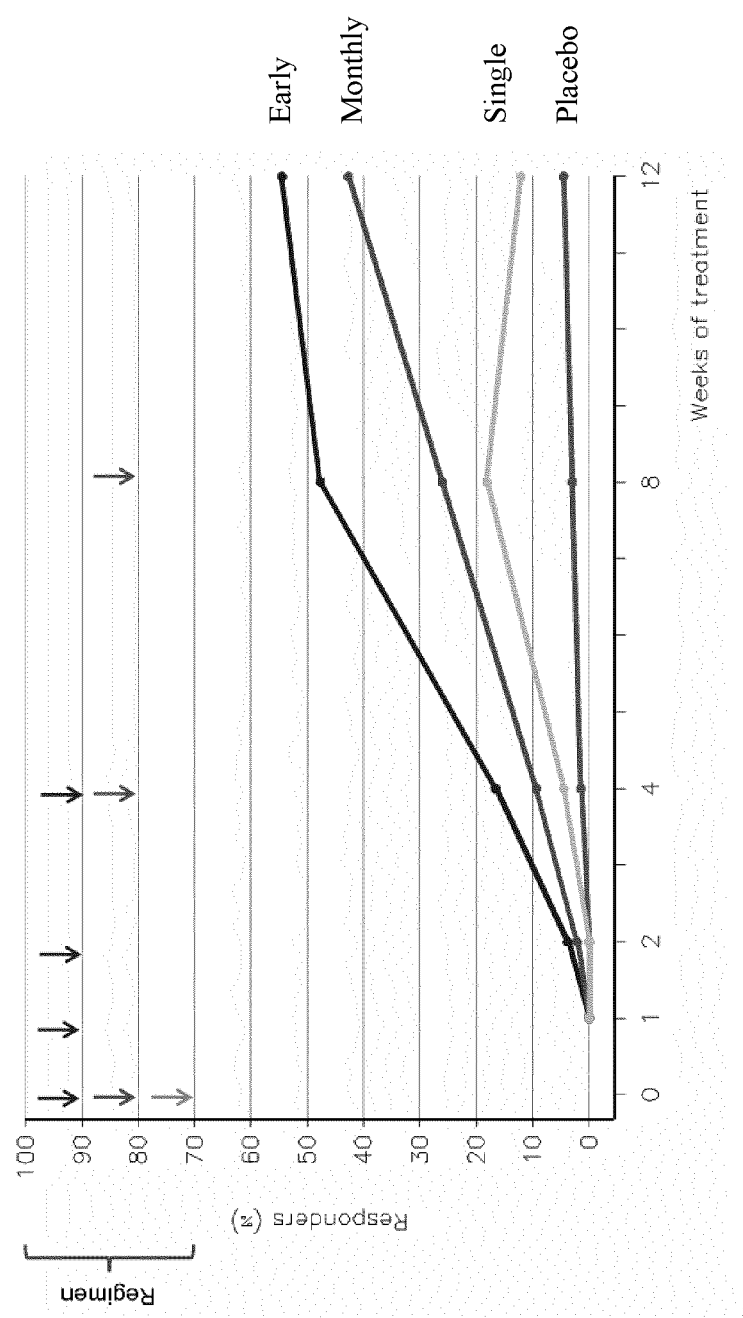
Figure 3: PASI75 response rates in study CAIN457A2211 during the 12 week induction phase, following different treatment regimens of 150 mg s.c. secukinumab,

Figure 4: Study A2211 PASI 75 achievement by patient visit (subgroup of subjects randomized to the maintenance period)
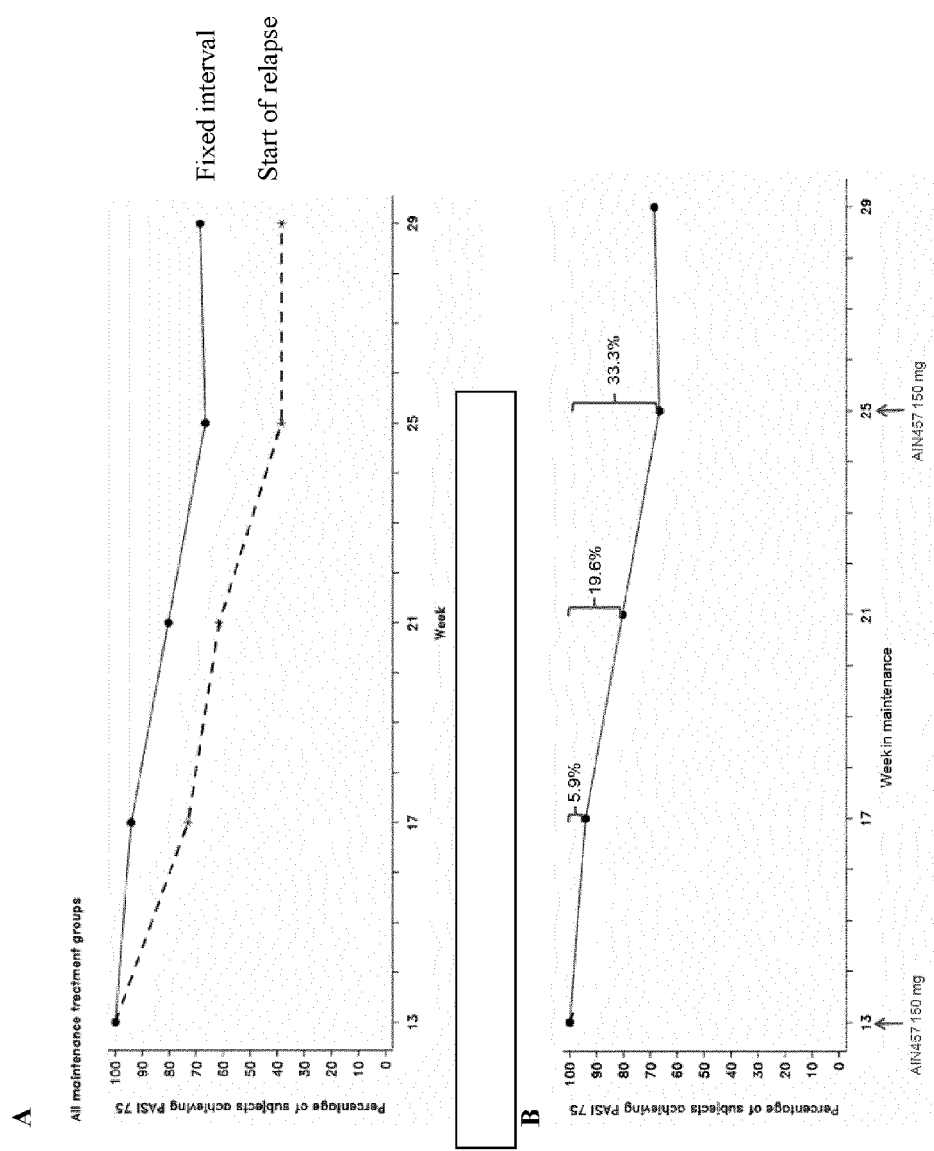

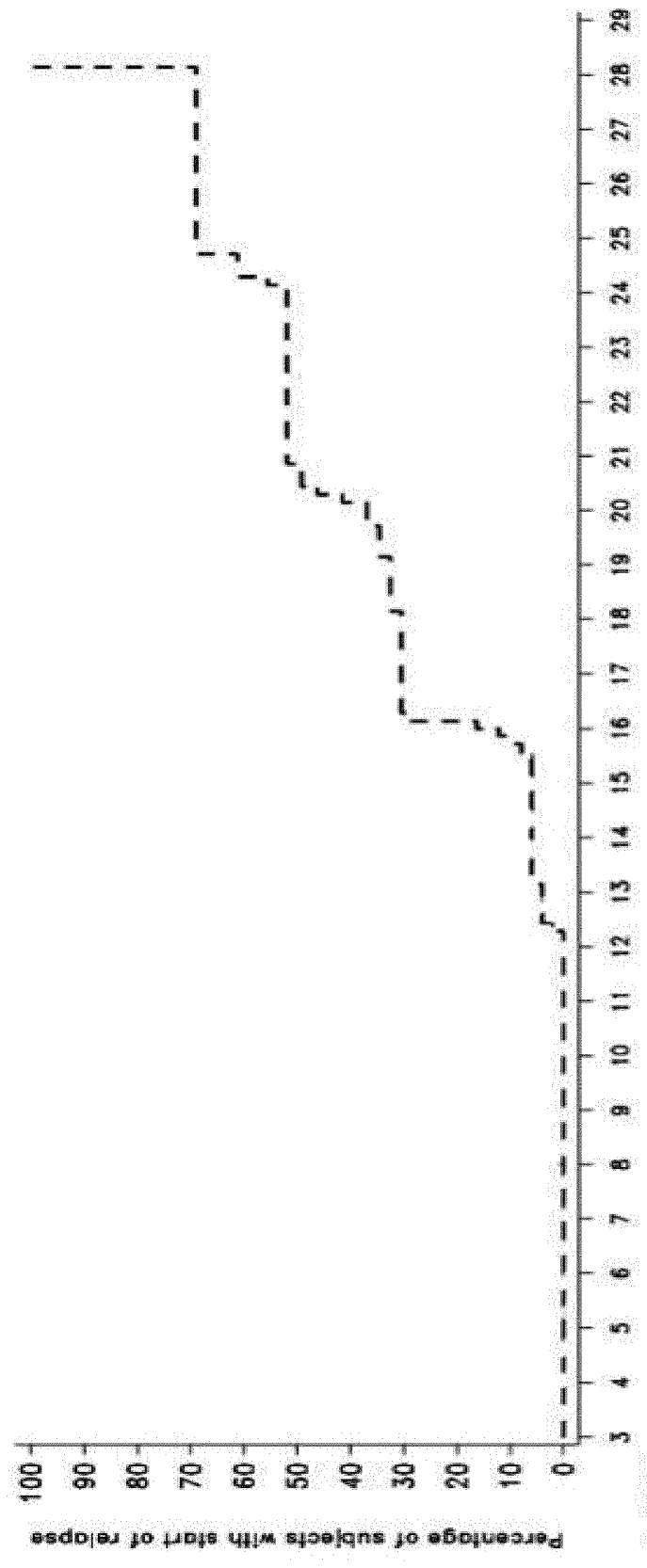
Figure 5: Observed cumulative probability to experience "Start of Relapse" in "individualized treatment" maintenance in study CAIN457A2211.

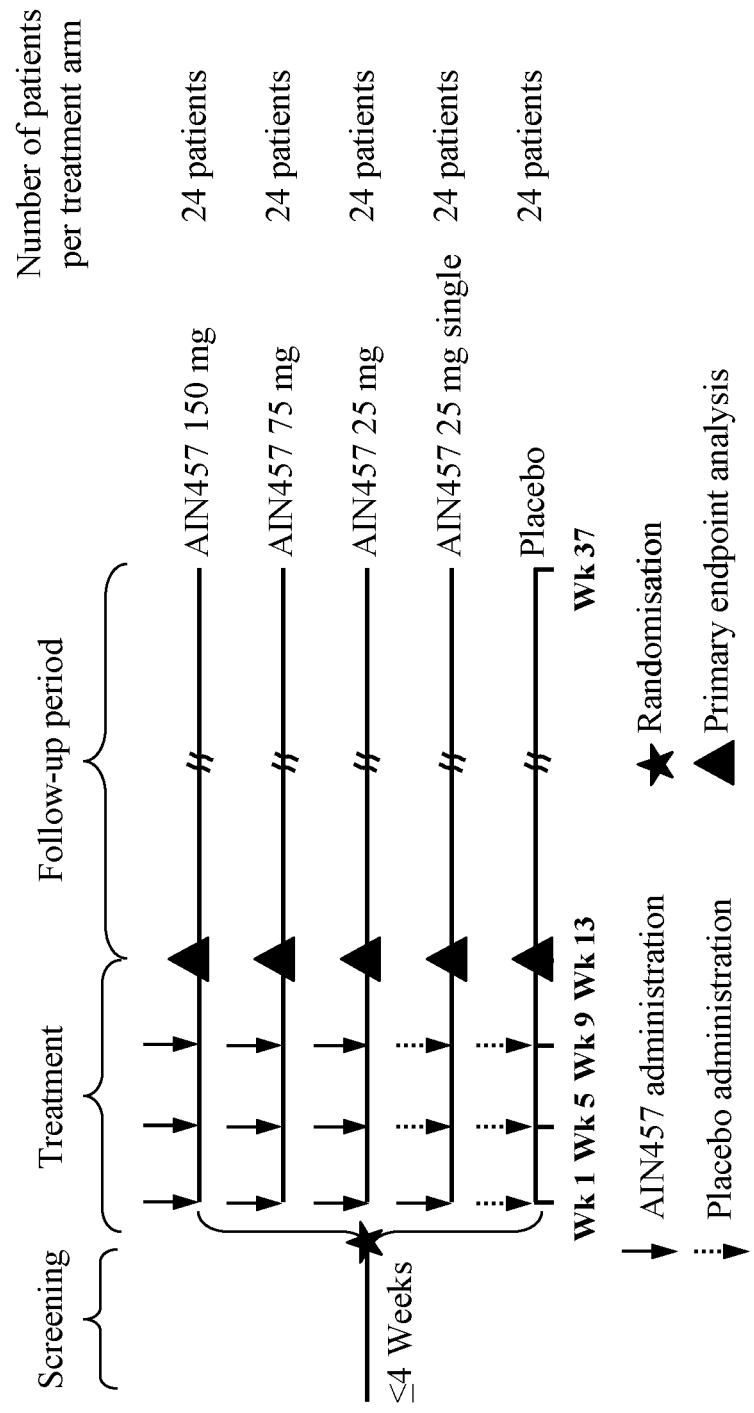
Figure 6: CAIN457A2220 Study Design

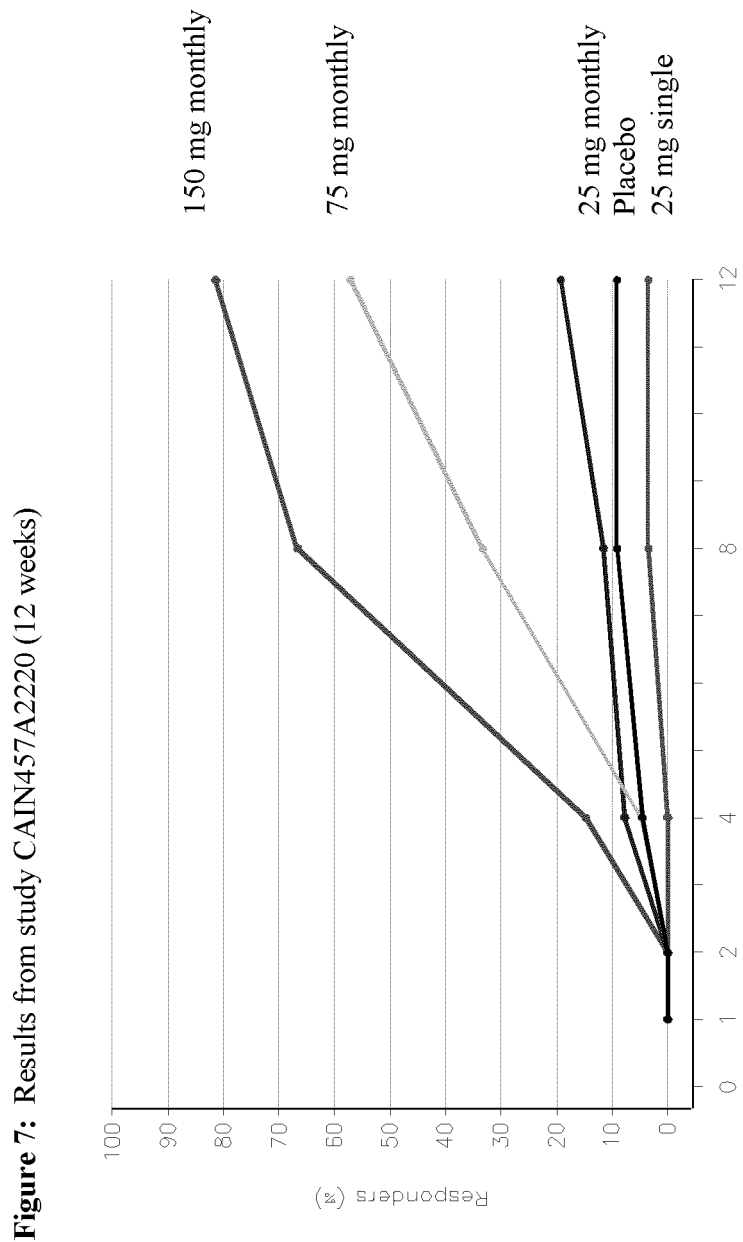
Figure 7: Results from study CAIN457A2220 (12 weeks)

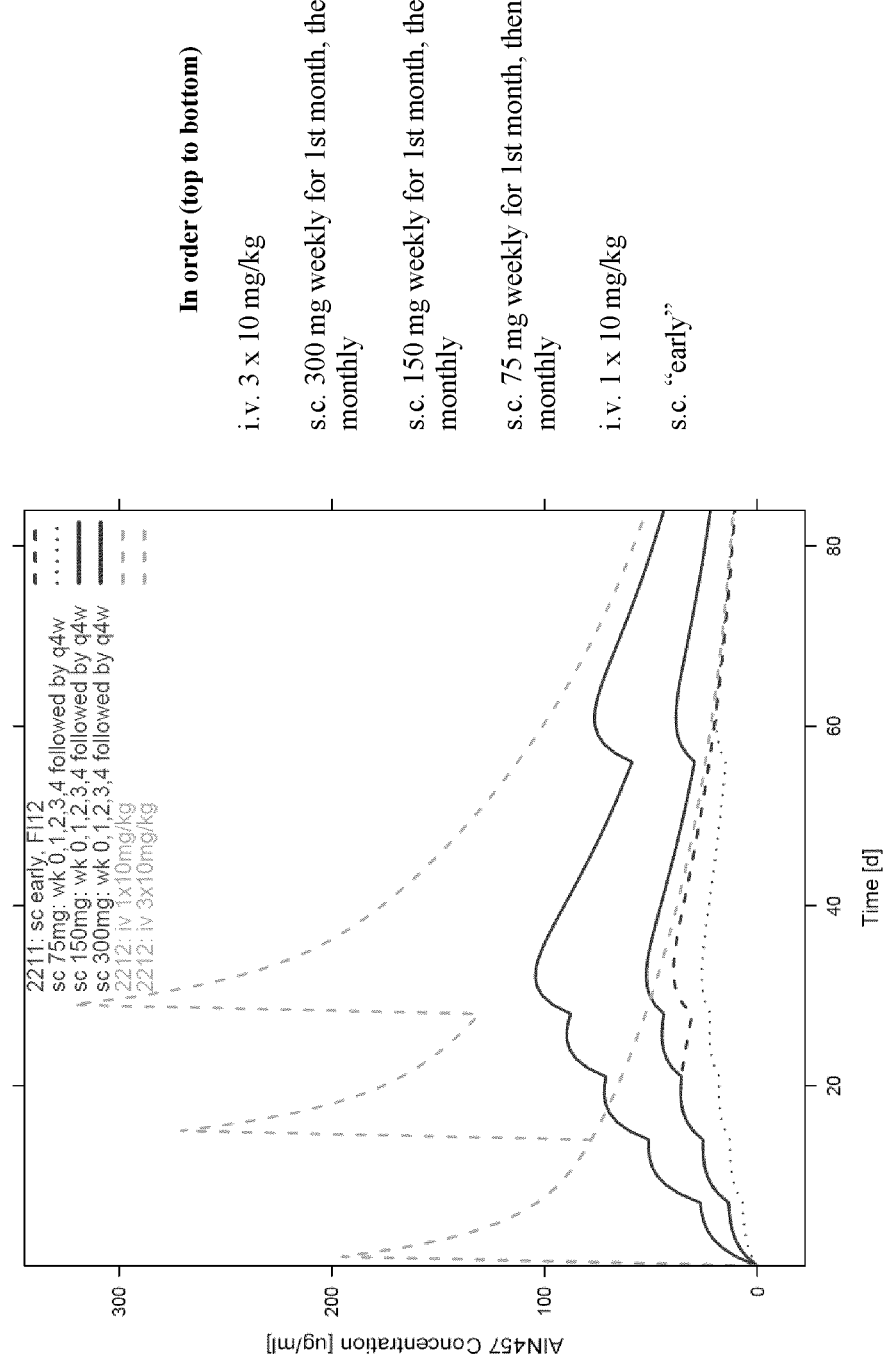
Figure 8: Simulated i.v. and s.c. exposures for different secukinumab regimens

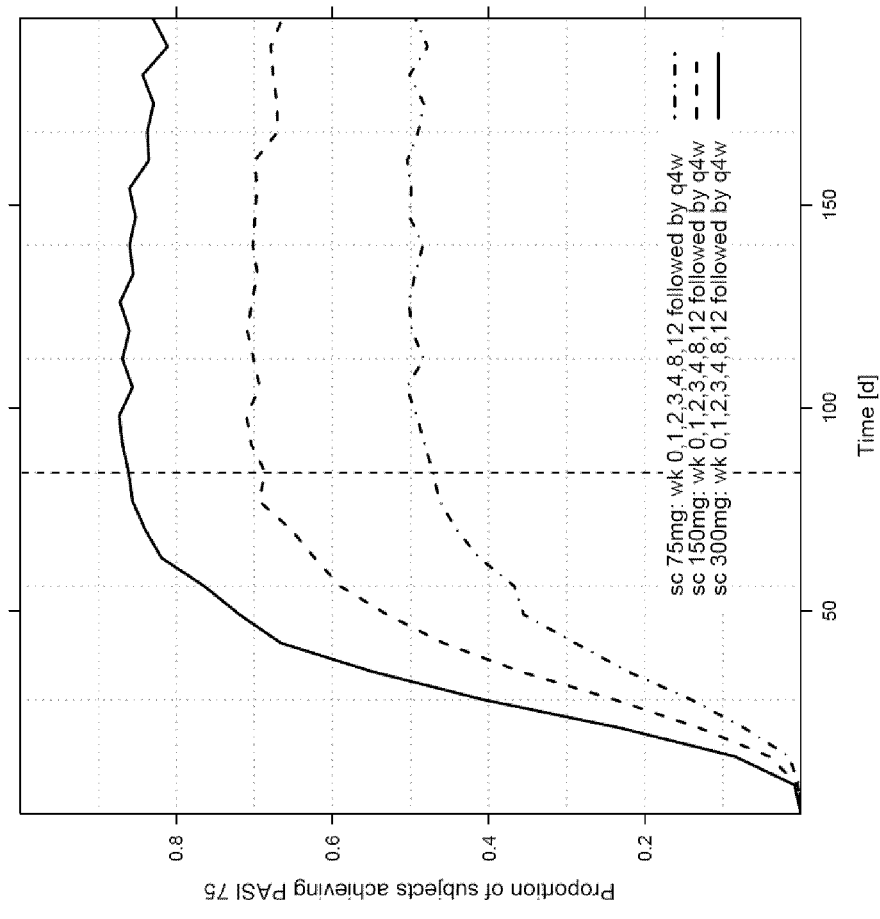
Figure 9: Simulated PASI 75 induction and maintenance response rates for phase III doses

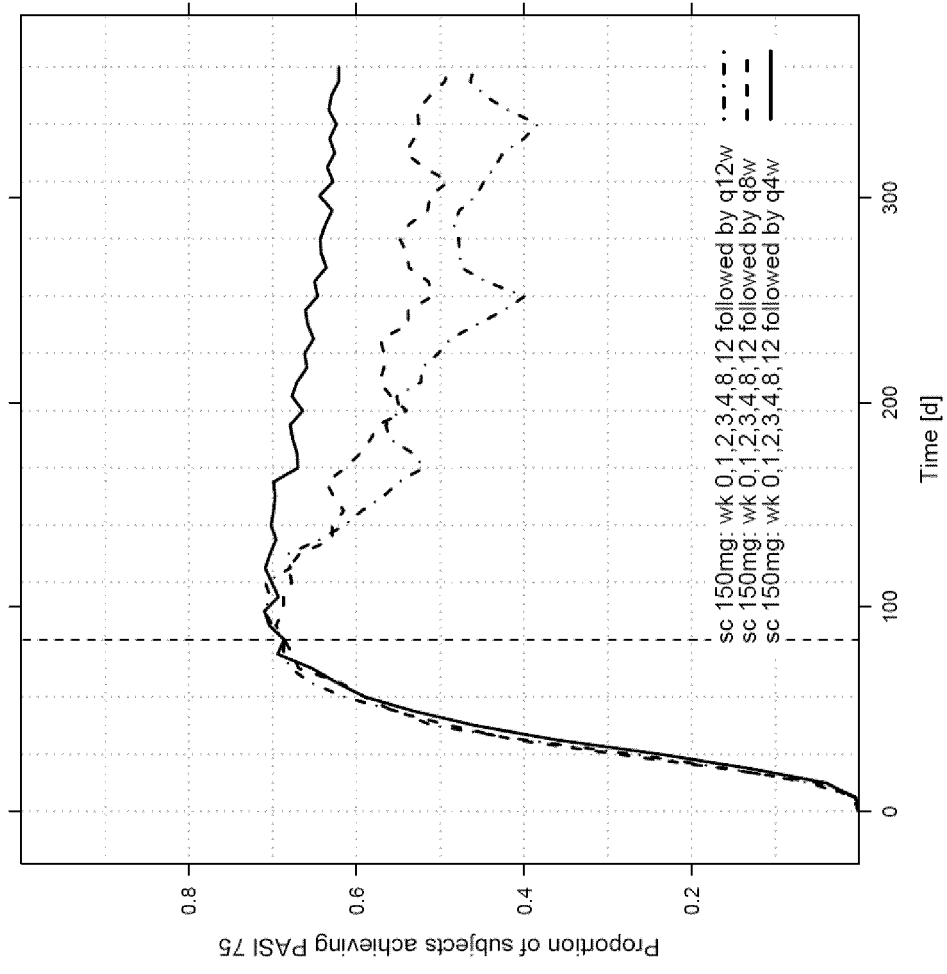
Figure 10: Simulated PASI 75 response rates for different fixed treatment intervals

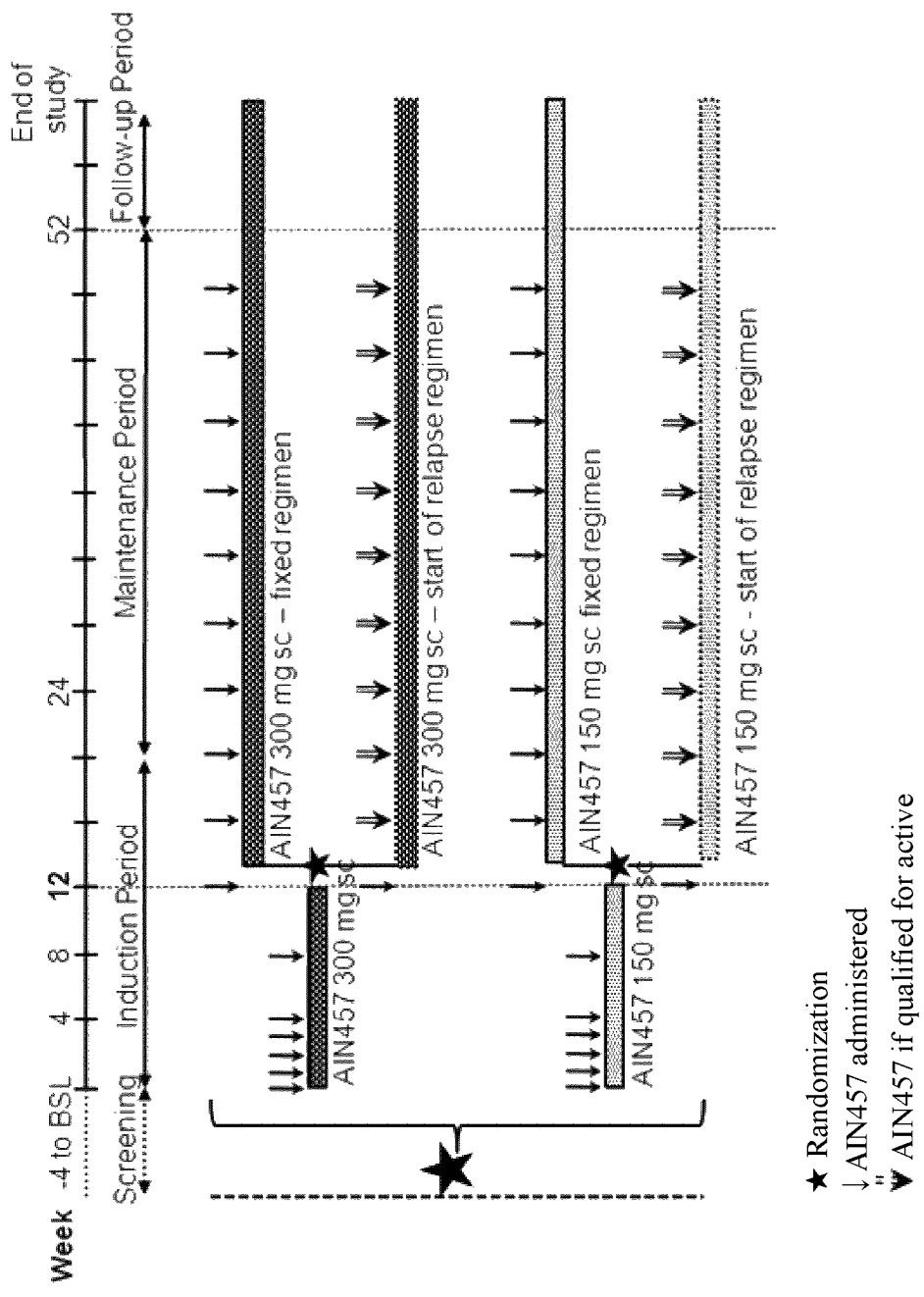
Figure 11: CAIN457A2304 Study design

METHODS OF TREATING PSORIASIS USING IL-17 ANTIBODY

This application is a 371 of PCT/EP2011/067522 filed on Oct. 7, 2011 which claims benefit of U.S. Provisional Application No. 61/391,388 filed on Oct. 8, 2010, which in their entirety are herein incorporated by reference.

TECHNICAL FIELD

The disclosure relates to novel regimens for treating psoriasis, which employ a therapeutically effective amount of an IL-17 antagonist, e.g., an IL-17 binding molecule, e.g., an IL-17 antibody, such as the AIN457 antibody (which is also known as "secukinumab").

BACKGROUND OF THE DISCLOSURE

Psoriasis is a chronic relapsing disease of the skin characterized by variable clinical features. Plaque (also called plaque-type or chronic plaque) psoriasis, which presents with erythrosquamous plaques, is the most frequent clinical presentation and, therefore, also called psoriasis vulgaris. Accumulating evidence indicates that psoriasis is a multifactorial disorder caused by the concerted action of multiple disease genes in a single individual, triggered by environmental factors. It has been speculated that this could be due to the effects of a chronic inflammatory condition. Regardless of the origin, once psoriasis has appeared as a localized disease, it persists throughout life, manifesting at often unpredictable intervals.

Traditional approaches for treating moderate to severe psoriasis include topical therapy, phototherapy (UVB, PUVA), and small molecule systemic therapy, namely methotrexate and cyclosporin. Safety, largely related to cumulative kidney and liver toxicity, is a major concern during long-term psoriasis treatment using cyclosporine and methotrexate, and requires frequent monitoring. McClure et al. (2001) Drug Safety 25:913-27. To reduce safety concerns, physicians have developed strategies such as combination, rotation, sequential and intermittent approaches in order to avoid cumulative organ toxicity (or, in the case of phototherapy, potential malignancy). Van de Kerkhoff et al. (2001) Clin. Exp. Dermatol 26:356-61. In general, when rotating to a new therapy, a first drug is gradually tapered while a next drug (or next therapy) is introduced. In some cases, after a first drug is tapered, a patient may be untreated until mild symptoms appear, at which time phototherapy or topical therapy is employed until symptoms are no longer tolerable, and a second drug is then introduced. Using this method, repeat treatment with a first drug may be delayed as long as possible (e.g., years). However, rebound can occur during cyclical therapies, e.g., in response to cyclosporin. Moreover, even during a "holiday" from the primary drug, the patient is typically undergoing psoriasis treatment using phototherapy or topical therapy.

Biologics appeared to present a solution to the unwieldy, dangerous, and inconvenient traditional systemic psoriasis treatment regimens. Given that biologics should have no organ toxicity, prolonged use thereof would be expected to be safe, making life-long treatment feasible. Unfortunately, adverse events have occurred to varying extent during chronic biologic treatment of psoriasis, most notably the reactivation of latent tuberculosis infections and the induction (or exacerbation of) demyelinating conditions due to TNF-alpha antagonism. Ferrandiz et al. (2010) Clinics in Dermatology 28:81-87. Other adverse events include thrombocytopenia, psoriasis-related adverse events (e.g., papular eruptions and inflammatory flares), liver toxicity, lymphopenia, and cardiovascular complications (including congestive heart failure or its worsening). Ferrandiz et al.; Sullivan and Preda (2009) Aust. Prescr. 32:14-18; Korkina et al. (2010) Drugs of Today 46:119-36. As a result, some clinicians have modified biological treatment regimens in their practice, i.e., by discontinuing and reinitiating therapy. However, concerns about intermittent biologic therapy, which include rebound, immunogenicity upon retreatment, and decreased response compared to that achieved during a first regimen (which occurs during infliximab, adalimumab and etanercept retreatment), suggest that some biologic therapies are best used in a continuous rather than on-demand setting. Ferrandiz et al.; Sullivan and Preda; Menter et al. (2008) J. Am. Acad. Dermatol 58:826-850; Gelfand et al. (2008) Value in Health 11:400-407; Menter et al. (2007) Am Acad Dermatol. 56(1):31.

The financial burden of long term continuous biological treatment is tremendous. There are also concerns that the long term usage of biologics, especially chronic TNF-alpha antagonists, might result in malignancies and other serious disorders. Accordingly, new psoriasis treatment regimens, which avoid the dangers of traditional continuous systemic therapy (i.e., inconvenient rotational therapy, side effects, organ toxicity) and continuous biologic therapy (i.e., infection, potential malignancy, financial burden, unknown longterm side effects), as well as the drawbacks of intermittent therapy (i.e., rebound, decreased retreatment response) are needed. Herein are disclosed novel regimens for the treatment of psoriasis, which overcome the obstacles encountered during continuous systemic therapy (both small molecule or biological) and intermittent biologic therapy.

SUMMARY OF THE DISCLOSURE

IL-17A is the central lymphokine of a subset of inflammatory T cells, the Th17 cells which, in several animal models, are pivotal in several autoimmune and inflammatory processes. IL-17A is mainly produced by memory effector CD4+ and CD8+ T lymphocytes. IL-17A is being recognized as one of the principal pro-inflammatory cytokines in immune mediated inflammatory diseases. Neutralization of IL-17A may be used to treat the underlying pathophysiology of immune mediated disease, and as a consequence provide relief of symptoms.

The psoriasis treatment regimens of the disclosure employ a therapeutically effective amount of an IL-17 antagonist, e.g., an IL-17 binding molecule, e.g., an IL-17 antibody, such as the AIN457 antibody (secukinumab). Secukinumab, disclosed in WO 2006/013107 (also published as US20090280131, which is hereby incorporated by reference in its entirety), is a recombinant high-affinity fully human monoclonal anti-human Interleukin-17A antibody of the IgG1/κ-class. Secukinumab binds to human IL-17A and neutralizes the bioactivity of this cytokine. Secukinumab has a very high affinity for IL-17, i.e., a $K_D$ of about 100-200 μM and an $IC_{50}$ of about 0.4 nM for in vitro neutralization of the biological activity of 0.67 nM human IL-17A. Thus, secukinumab neutralizes antigen at a molar ratio of about 1:1. This high binding affinity makes secukinumab particularly suitable for therapeutic applications. Furthermore, secukinumab has a very long half life, i.e., about 4 weeks (i.e., about 30 days), which allows for prolonged periods between administration, an exceptional property when treating chronic life-long disorders, such as psoriasis. Due to the long half-life, high affinity and fast onset of action of secukinumab, it is possible to treat psoriasis using relatively low doses of secukinumab administered at infrequent intervals.

It is an object of the disclosure to provide novel treatment regimens for psoriasis, which employ induction and/or maintenance regimens using therapeutically effective amounts of an IL-17 antagonist, e.g., an IL-17 binding molecule, e.g., IL-17 antibody, such as secukinumab. It is an another object of the disclosure to provide novel methods of treating psoriasis in patients at start of relapse (SoR), which employ a therapeutically effective amount of an IL-17 antagonist, e.g., an IL-17 binding molecule, e.g., IL-17 antibody, such as secukinumab. Treatment at SoR allows an individualized approach to psoriasis therapy and provides effective relief, while employing the lowest possible dose of drug.

Accordingly, disclosed herein are methods of treating psoriasis, comprising: a) administering an IL-17 antagonist, e.g., an IL-17 binding molecule, to a patient in need thereof during an induction regimen; and b) thereafter administering the IL-17 antagonist, e.g., IL-17 binding molecule, to the patient during a maintenance regimen. The maintenance regimen may employ continuous (e.g., monthly treatment) or intermittent dosing (e.g., treatment at SoR).

Disclosed herein are methods of treating psoriasis, comprising: a) administering an IL-17 antagonist, e.g., IL-17 binding molecule to a patient in need thereof during an induction regimen, wherein the induction regimen comprises a loading regimen, wherein the loading regimen comprises administering the patient five doses of about 75 mg-about 300 mg (e.g., about 150 mg-about 300 mg) of the IL-17 antagonist, e.g., IL-17 binding molecule, each of the five doses being delivered weekly, beginning on week zero; and b) thereafter, administering the IL-17 antagonist, e.g., IL-17 binding molecule to the patient during a maintenance regimen.

Disclosed herein are IL-17 antagonists, e.g., IL-17 binding molecules for use in treating psoriasis, characterized in that at least one dose of the IL-17 antagonist, e.g., IL-17 binding molecule is administered to a patient at start of relapse from a prior treatment with the IL-17 antagonist, e.g., IL-17 binding molecule. Also disclosed herein are methods of treating psoriasis, comprising: a) identifying a patient at start of relapse from a prior psoriasis treatment employing an IL-17 antagonist, e.g., IL-17 binding molecule; and b) administering to the patient at least one dose of the IL-17 antagonist, e.g., IL-17 binding molecule.

Disclosed herein are methods of treating psoriasis, comprising: a) administering a patient in need thereof five doses of about 75 mg-about 300 mg (e.g., about 150 mg-about 300 mg) of an IL-17 antagonist, e.g., IL-17 binding molecule, each of the five doses being delivered weekly, beginning on week zero; b) administering the patient about 75 mg-about 300 mg (e.g., about 150 mg-about 300 mg) the IL-17 binding molecule during week eight; c) administering the patient at least one dose of about 75 mg-about 300 mg (e.g., about 150 mg-about 300 mg) the IL-17 antagonist, e.g., IL-17 binding molecule at start of relapse; and d) repeating step c) at each additional start of relapse.

Disclosed herein are therapeutic regimens for treating psoriasis, comprising: a) administering an IL-17 antagonist, e.g., IL-17 binding molecule to a patient in need thereof during an induction regimen comprising: i. administering about 75 mg-about 300 mg (e.g., about 150 mg-about 300 mg) of the IL-17 antagonist, e.g., IL-17 binding molecule to the patient weekly for five weeks, wherein the first dose of the IL-17 antagonist, e.g., IL-17 binding molecule is administered during week zero; and ii. thereafter administering about 75 mg-about 300 mg (e.g., about 150 mg-about 300 mg) of the IL-17 antagonist, e.g., IL-17 binding molecule to the patient during week eight; and b) administering the IL-17 antagonist, e.g., IL-17 binding molecule to the patient during a maintenance regimen comprising: i. administering about 75 mg-about 300 mg (e.g., about 150 mg-about 300 mg) of the IL-17 binding molecule to the patient each month, every two months or every three months; or ii. administering at least one dose of about 75 mg-about 300 mg (e.g., about 150 mg-about 300 mg) of the IL-17 antagonist, e.g., IL-17 binding molecule to the patient at start of relapse.

Disclosed herein are IL-17 binding molecules for use in treating psoriasis, characterized in that the IL-17 antagonist, e.g., IL-17 binding molecule is to be administered: a) during an induction regimen, wherein the induction regimen comprises a loading regimen, wherein the loading regimen comprises administering five doses of about 75 mg-about 300 mg (e.g., about 150 mg-about 300 mg) of the IL-17 antagonist, e.g., IL-17 binding molecule, each of the five doses being delivered weekly, beginning on week zero; and b) thereafter, during a maintenance regimen.

Disclosed herein are IL-17 antagonists, e.g., IL-17 binding molecules for use in treating psoriasis, characterized in that the IL-17 antagonist, e.g., IL-17 binding molecule is: a) to be administered to a patient in need thereof as five doses of about 75 mg-about 300 mg (e.g., about 150 mg-about 300 mg), each of the five doses being delivered weekly, beginning on week zero; b) thereafter to be administered to the patient during week eight in an amount of about 75 mg-about 300 mg (e.g., about 150 mg-about 300 mg); c) thereafter to be administered to the patient as at least one dose of about 75 mg-about 300 mg (e.g., about 150 mg-about 300 mg) at start of relapse; and d) thereafter to be administered to the patient at start of each additional relapse as at least one dose of about 75 mg-about 300 mg (e.g., about 150 mg-about 300 mg).

Disclosed herein are IL-17 antagonists, e.g., IL-17 binding molecules for use in treating psoriasis, characterized in that the IL-17 antagonist, e.g., IL-17 binding molecule is: a) to be administered to a patient in need thereof during an induction regimen comprising: i. the IL-17 antagonist, e.g., IL-17 binding molecule is to be administered to the patient at a dose of about 75 mg-about 300 mg (e.g., about 150 mg-about 300 mg) weekly for five weeks, wherein the first dose of the IL-17 antagonist, e.g., IL-17 binding molecule is to be administered during week zero; and ii. thereafter the IL-17 antagonist, e.g., IL-17 binding molecule is to be administered to the patient at a dose of about 75 mg-about 300 mg (e.g., about 150 mg-about 300 mg) during week eight; and b) to be administered to the patient during a maintenance regimen comprising: i. the IL-17 antagonist, e.g., IL-17 binding molecule is to be administered to the patient at a dose of about 75 mg-about 300 mg (e.g., about 150 mg-about 300 mg) each month, every two months or every three months; or ii. the IL-17 antagonist, e.g., IL-17 binding molecule is to be administered to the patient as at least one dose of about 75 mg-about 300 mg (e.g., about 150 mg-about 300 mg) of the IL-17 antagonist, e.g., IL-17 binding molecule at start of relapse.

Disclosed herein are uses of IL-17 antagonists, e.g., IL-17 binding molecules for the manufacture of a medicament for treating psoriasis, characterized in that the IL-17 antagonist, e.g., IL-17 binding molecule is to be administered to a patient at start of relapse from a prior treatment with the IL-17 antagonist, e.g., IL-17 binding molecule.

Disclosed herein are IL-17 antagonists, e.g., IL-17 binding molecules for use in treating psoriasis in a patient, wherein said patient is to be identified at start of relapse from a prior treatment with the IL-17 antagonist, e.g., IL-17 binding molecule and wherein said patient is to be administered at least one dose of the IL-17 antagonist, e.g., IL-17 binding molecule.

Disclosed herein are pharmaceutical compositions for treating psoriasis, comprising as an active ingredient and the IL-17 antagonist, e.g., IL-17 binding molecule, wherein the IL-17 antagonist, e.g., IL-17 binding molecule is to be administered to a patient at start of relapse from a prior treatment with the IL-17 antagonist, e.g., IL-17 binding molecule.

Disclosed herein are methods of treating psoriasis, comprising: a) administering a patient in need thereof five weekly doses of about 75 mg-about 300 mg (e.g., about 150 mg-about 300 mg) of an IL-17 antagonist, e.g., IL-17 binding molecule; and b) thereafter administering: i) about 75 mg-about 300 mg (e.g., about 150 mg-about 300 mg) of the IL-17 antagonist, e.g., IL-17 binding molecule to the patient monthly or ii) one dose of about 75 mg-about 300 mg (e.g., about 150 mg-about 300 mg) of the IL-17 antagonist, e.g., IL-17 binding molecule to the patient about one month following step a) and thereafter administering at least one dose of about 75 mg-about 300 mg (e.g., about 150 mg-about 300 mg) of the IL-17 antagonist, e.g., IL-17 binding molecule to the patient at start of relapse.

Disclosed herein are therapeutic regimens for treating psoriasis, comprising: a) administering a patient in need thereof five weekly doses of about 75 mg-about 300 mg (e.g., about 150 mg-about 300 mg) of an IL-17 antagonist, e.g., IL-17 binding molecule; and b) thereafter administering: i) about 75 mg-about 300 mg (e.g., about 150 mg-about 300 mg) of the IL-17 antagonist, e.g., IL-17 binding molecule to the patient monthly or ii) one dose of about 75 mg-about 300 mg (e.g., about 150 mg-about 300 mg) of the IL-17 antagonist, e.g., IL-17 binding molecule to the patient about one month following step a) and thereafter administering at least one dose of about 75 mg-about 300 mg (e.g., about 150 mg-about 300 mg) of the IL-17 antagonist, e.g., IL-17 binding molecule to the patient at start of relapse.

Disclosed herein are methods of treating psoriasis, comprising: a) administering an IL-17 antagonist, e.g., IL-17 binding molecule to a patient in need thereof during an induction regimen, wherein the induction regimen comprises a loading regimen that provides a mean maximum plasma concentration ($C_{max}$) of the IL-17 antagonist, e.g., IL-17 binding molecule of about 52 µg/ml-about 104 µg/ml; and b) thereafter administering the IL-17 antagonist, e.g., IL-17 binding molecule to the patient during a maintenance regimen that provides an average steady-state trough level of the IL-17 antagonist, e.g., IL-17 binding molecule between about 5 µg/ml-about 70 µg/ml.

Disclosed herein are IL-17 binding molecules for use in treating psoriasis, characterized in that the IL-17 binding molecule: a) is to be administered to the patient during an induction regimen, wherein the induction regimen comprises a loading regimen that provides a mean maximum plasma concentration ($C_{max}$) of the IL-17 binding molecule of about 52 µg/ml-about 104 µg/ml; and b) thereafter, is to be administered to the patient during a maintenance regimen that provides an average steady-state trough level of the IL-17 binding molecule between about 5 µg/ml-about 70 µg/ml.

Disclosed herein are methods of treating psoriasis, comprising: a) administering an IL-17 antagonist, e.g., IL-17 binding molecule to a patient in need thereof during an induction regimen, wherein the induction regimen comprises a loading regimen that provides a mean trough level one month after the fourth dose of about 29.2 µg/ml; and b) thereafter administering the IL-17 antagonist, e.g., IL-17 binding molecule to the patient during a maintenance regimen that provides an average steady-state trough level of the IL-17 antagonist, e.g., IL-17 binding molecule of about 15 µg/ml.

Disclosed herein are IL-17 binding molecules for use in treating psoriasis, characterized in that the IL-17 binding molecule: a) is to be administered to the patient during an induction regimen, wherein the induction regimen comprises a loading regimen that provides a mean trough level one month after the fourth dose of about 29.2 µg/ml; and b) thereafter, is to be administered to the patient during a maintenance regimen that provides an average steady-state trough level of the IL-17 binding molecule of about 15 µg/ml.

In some of the above mentioned methods, therapeutic regimens, kits, uses, and pharmaceutical compositions, the prior treatment with the IL-17 antagonist, e.g., IL-17 binding molecule comprises an induction regimen. In further embodiments, the induction regimen comprises a loading regimen. In some embodiments, the loading regimen comprises administering the patient five doses of about 75 mg-about 300 mg (e.g., about 150 mg-about 300 mg) of the IL-17 antagonist, e.g., IL-17 binding molecule, each of the five doses being delivered weekly, beginning on week zero. In some embodiments, the five doses are each about 75 mg, about 150 mg or about 300 mg. In some embodiments, five doses of about 150 mg are administered to the patient if the patient weighs less than 90 kg and five doses of about 300 mg are administered to the patient if the patient weighs more than or equal to 90 kg. In some embodiments, the induction regimen further comprises administering the patient about 75 mg-about 300 mg (e.g., about 150 mg-about 300 mg) the IL-17 antagonist, e.g., IL-17 binding molecule during week eight. In some embodiments, the prior treatment with the IL-17 antagonist, e.g., IL-17 binding molecule comprises administering to the patient at least one dose of the IL-17 antagonist, e.g., IL-17 binding molecule at start of relapse. In some of the above mentioned methods, therapeutic regimens, kits, uses, and pharmaceutical compositions, start of relapse is defined as the loss of 20% of the maximum PASI response achieved at any time before the visit at which the assessment of start of relapse is made and loss of PASI 75. In some of the above mentioned methods, therapeutic regimens, kits, uses, and pharmaceutical compositions, the psoriasis is chronic plaque-type psoriasis.

In some of the above mentioned methods, therapeutic regimens, combinations, combination therapies, kits, uses, and pharmaceutical compositions, the IL-17 antagonist, e.g., IL-17 binding molecule is selected from the group consisting of:

a) secukinumab;

b) an IL-17 antibody that binds to an epitope of IL-17 comprising Leu74, Tyr85, His86, Met87, Asn88, Val124, Thr125, Pro126, Ile127, Val128, His129;

c) an IL-17 antibody that binds to an epitope of IL-17 comprising Tyr43, Tyr44, Arg46, Ala79, Asp80;

d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain;

e) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 μM, and wherein the IL-17 binding molecule has an in vivo half-life of about 4 weeks; and f) an IL-17 antibody that comprises an antibody selected from the group consisting of:
  i) an immunoglobulin heavy chain variable domain ($V_H$) comprising the amino acid sequence set forth as SEQ ID NO:8;
  ii) an immunoglobulin light chain variable domain ($V_L$) comprising the amino acid sequence set forth as SEQ ID NO:10;
  iii) an immunoglobulin $V_H$ domain comprising the amino acid sequence set forth as SEQ ID NO:8 and an immunoglobulin $V_L$ domain comprising the amino acid sequence set forth as SEQ ID NO:10;
  iv) an immunoglobulin $V_H$ domain comprising the hypervariable regions set forth as SEQ ID NO:1, SEQ ID NO:2, and SEQ ID NO:3;
  v) an immunoglobulin $V_L$ domain comprising the hypervariable regions set forth as SEQ ID NO:4, SEQ ID NO:5 and SEQ ID NO:6;
  vi) an immunoglobulin $V_H$ domain comprising the hypervariable regions set forth as SEQ ID NO:11, SEQ ID NO:12 and SEQ ID NO:13;
  vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; and
  viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

In the above mentioned methods, therapeutic regimens, kits, uses, and pharmaceutical compositions, a preferred embodiment employs a human antibody to IL-17, e.g., most preferably secukinumab.

BRIEF DESCRIPTION OF THE DRAWINGS

FIG. 1 shows that rebound is not observed in secukinumab-treated patients within 8 weeks after dosing. The figure shows individual patient profiles from study CAIN457A2212. All patients in each group are shown. Baseline PASI is shown as 100% for all patients. A PASI 75 response is achieved if the curve reaches 25% on the Y-axis. A rebound would have been observed if 125% on the Y-Axis (marked with a horizontal gray line) would have been reached within 8 weeks after last study drug administration. Note that the time point of eight weeks after last study drug administration (marked in the figure with a vertical gray line) is at Week 8 for the groups "1×3 mg/kg" and "1×10 m/kg", but at Week 12 for the "3×10 mg/kg" group; the "placebo" group did not receive any active treatment.

FIG. 2 shows the study design for clinical trial CAIN457A2211.

FIG. 3 shows PASI75 response rates in study CAIN457A2211 during the 12 week induction phase, following different treatment regimens of 150 mg s.c. secukinumab. The arrows indicate the time points of secukinumab administration. No secukinumab was administered in the placebo arm.

FIG. 4 Study CAIN457A2211: PASI 75 achievement response rates by patient visit treatment week (subgroup of subjects randomized to the maintenance period). By definition, the PASI 75 response rate at Week 13 was 100%, as only patients with a PASI 75 achievement were re-randomized into the double-blind maintenance treatment period of the study. Patients in the "Fixed Interval" group received 150 mg of secukinumab at Week 13 and at Week 25. Patients in the "Start of Relapse" group did not receive secukinumab at Week 13; the received 150 mg of secukinumab at Weeks 17, 21, 25, and 29 ONLY if they suffered from a start of relapse at the respective time point. 4A shows results for both the "Fixed Interval" and the "Start of Relapse" groups. 4B shows only the results of the "Fixed Interval" group. The difference in response rate compared to Week 13 (100% by definition) is given for Weeks 17, 21, and 25. The time points of secukinumab (AIN457) administration are indicated.

FIG. 5 shows the observed cumulative probability to experience "Start of Relapse" in "individualized treatment" maintenance in study CAIN457A2211. In the figure the percentage of subjects with start of relapse (y-axis) is plotted versus time in weeks since last secukinumab injection in the induction period. Patients were treated with one of the three secukinumab induction regimes ("Single", "Monthly", and "Early") during the first twelve weeks. As a result, the time since last secukinumab administration differs within this group.

FIG. 6 shows the study design for clinical trial CAIN457A2220.

FIG. 7 shows PASI 75 response rates from in study CAIN457A2220 (12 weeks). Subjects with "monthly" treatment received injections of secukinumab at Weeks 0, 4, and 8. Subjects in the "25 mg single" arm received secukinumab at Week 0 only. Placebo patients did not receive secukinumab injections.

FIG. 8 shows simulated PK plasma concentration profiles of secukinumab for the regimens implemented in phase III (subcutaneous), as well as for regimens in studies CAIN457A2212 (intravenous route of administration) and CAIN457A2211 (subcutaneous). All simulated profiles are for typical patients, assuming a body weight of 90.9 kg (based on the typical body weight observed in secukinumab in psoriasis studies)."

FIG. 9 shows simulated PASI 75 induction and maintenance response rates for doses 75 mg. 150 mg and 300 mg for a treatment duration of 200 days. After induction treatment (Weeks 0, 1, 2, 3, 4, and 8), doses are given at Week 12 and every four weeks thereafter.

FIG. 10 shows simulated PASI 75 response rates for different fixed treatment intervals. On the basis of one of the doses for phase III (150 mg), the impact of different fixed treatment intervals (4, 8, and 12 weeks) is simulated for the treatment duration of 365 days. Induction treatment is identical for all three groups, and the first dose in maintenance is given on day 84 (=Week 12) in all groups.

FIG. 11 shows the study design for clinical trial CAIN457A2304.

DETAILED DESCRIPTION OF THE DISCLOSURE

Various aspects of the disclosure are described in further detail in the following subsections. All patents, published patent applications, publications, references and other material referred to herein are incorporated by reference herein in their entirety.

The term "comprising" encompasses "including" as well as "consisting," e.g., a composition "comprising" X may consist exclusively of X or may include something additional, e.g., X+Y.

The term "about" in relation to a numerical value x means +/−10%, unless the cotext dictates otherwise.

The word "substantially" does not exclude "completely" e.g., a composition which is "substantially free" from Y may be completely free from Y. Where necessary, the word "substantially" may be omitted from the definition of the disclosure.

"IL-17 antagonist" as used herein refers to a molecule capable of antagonizing (e.g., reducing, inhibiting, decreasing, delaying) IL-17 function, expression and/or signalling (e.g., by blocking the binding of IL-17 to the IL-17 receptor). Non-limiting examples of IL-17 antagonists include IL-17 binding molecules and IL-17 receptor binding molecules. In some embodiments of the disclosed methods, regimens, kits, processes, uses and compositions, an IL-17 antagonist is employed.

By "IL-17 binding molecule" is meant any molecule capable of binding to the human IL-17 antigen either alone or associated with other molecules. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity but of the same isotype, e.g. an anti-CD25 antibody, is used. Non-limiting examples of IL-17 binding molecules include small molecules, IL-17 receptor decoys, and antibodies as produced by B-cells or hybridomas and chimeric, CDR-grafted or human antibodies or any fragment thereof, e.g., F(ab')$_2$ and Fab fragments, as well as single chain or single domain antibodies. Preferably the IL-17 binding molecule antagonizes (e.g., reduces, inhibits, decreases, delays) IL-17 function, expression and/or signalling. In some embodiments of the disclosed methods, regimens, kits, processes, uses and compositions, an IL-17 binding molecule is employed.

By "IL-17 receptor binding molecule" is meant any molecule capable of binding to the human IL-17 receptor either alone or associated with other molecules. The binding reaction may be shown by standard methods (qualitative assays) including, for example, a binding assay, competition assay or a bioassay for determining the inhibition of IL-17 receptor binding to IL-17 or any kind of binding assays, with reference to a negative control test in which an antibody of unrelated specificity but of the same isotype, e.g. an anti-CD25 antibody, is used. Non-limiting examples of IL-17 receptor binding molecules include small molecules, IL-17 decoys, and antibodies to the IL-17 receptor as produced by B-cells or hybridomas and chimeric, CDR-grafted or human antibodies or any fragment thereof, e.g., F(ab')$_2$ and Fab fragments, as well as single chain or single domain antibodies. Preferably the IL-17 receptor binding molecule antagonizes (e.g., reduces, inhibits, decreases, delays) IL-17 function, expression and/or signalling. In some embodiments of the disclosed methods, regimens, kits, processes, uses and compositions, an IL-17 receptor binding molecule is employed.

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to IL-17 or the IL-17 receptor is employed.

The term "antigen-binding portion" of an antibody as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR). Exemplary antigen binding sites include the CDRs of secukinumab as set forth in SEQ ID NOs:1-6 and 11-13 (Table 5), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art. In some embodiments of the disclosed methods, regimens, kits, processes, uses and compositions, a single chain antibody or an antigen-binding portion of an antibody against IL-17 or the IL-17 receptor is employed.

The term "pharmaceutically acceptable" means a non-toxic material that does not interfere with the effectiveness of the biological activity of the active ingredient(s).

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). An isolated antibody may be substantially free of other cellular material and/or chemicals. An isolated antibody that "specifically binds" IL-17 may be crossreactive with other antigens, such as IL-17 molecules from other species. In some embodiments of the disclosed methods, regimens, kits, processes, uses and compositions, the IL-17 binding molecule is an isolated antibody.

The terms "monoclonal antibody" or "monoclonal antibody composition" as used herein refer to a preparation of antibody molecules of single molecular composition. A monoclonal antibody composition displays a single binding specificity and affinity for a particular epitope. In some embodiments of the disclosed methods, regimens, kits, processes, uses and compositions, the IL-17 binding molecule is a monoclonal antibody.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. (2000. J Mol Biol 296, 57-86). A "human antibody" need not be produced by a human, human tissue or human cell. The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In some embodiments of the disclosed methods, regimens, kits, processes, uses and compositions, the IL-17 binding molecule is a human antibody.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_{dis}$" or "$K_D$," as used herein, is intended to refer to the dissociation rate of a particular antibody-antigen interaction, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore analysis. Assays to evaluate the effects of the antibodies on functional properties of IL-17 (e.g., receptor binding, preventing or ameliorating osteolysis) are described in further detail in the Examples.

As used herein, the term "subject" and "patient" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

An antibody that "inhibits" one or more of the functional properties of IL-17 (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity causes a statistically significant decrease, e.g., by at least 10% of the measured parameter, by at least 50%, 80% or 90%, and in certain embodiments an antibody of the disclosure may inhibit greater than 95%, 98% or 99% of IL-17 functional activity.

The term "derivative", unless otherwise indicated, is used to define amino acid sequence variants, and covalent modifications of the IL-17 binding molecules and IL-17 receptor binding molecules according to the present disclosure, e.g., of a specified sequence.

A "functional derivative" includes a molecule having a qualitative biological activity in common with the disclosed IL-17 binding molecules and IL-17 receptor binding molecules. A functional derivative includes fragments and peptide analogs of an IL-17 binding molecule or an IL-17 receptor binding molecule according to the present disclosure. Fragments comprise regions within the sequence of a polypeptide according to the present disclosure, e.g., of a specified sequence. Functional derivatives of the IL-17 binding molecules or IL-17 receptor binding molecules disclosed herein preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 binding molecules and IL-17 receptor binding molecules disclosed herein (e.g., the $V_H$ and/or $V_L$ sequences of Table 5), or comprise CDRs that have at least about 65%, 75%, 85%, 95%, 96%, 97%, 98%, or even 99% overall sequence identity with the CDRs of the IL-17 binding molecules (e.g., secukinumab) or IL-17 receptor binding molecules disclosed herein (e.g., have 1, 2, or 3 amino acid differences from the CDRs set forth in Table 5), and substantially retain the ability to bind the human IL-17 or, e.g., inhibit IL-6 production of IL-17 induced human dermal fibroblasts. In some embodiments of the disclosed methods, regimens, kits, processes, uses and compositions, functional derivatives of the IL-17 binding molecules and IL-17 receptor binding molecules disclosed herein are employed.

"Inhibit IL-6" as used herein refers to the ability of an IL-17 binding molecule to decrease IL-6 production from primary human dermal fibroblasts. The production of IL-6 in primary human (dermal) fibroblasts is dependent on IL-17 (Hwang S Y et al., (2004) Arthritis Res Ther; 6:R120-128. In short, human dermal fibroblasts are stimulated with recombinant IL-17 in the presence of various concentrations of an IL-17 binding molecule or human IL-17 receptor with Fc part. The chimeric anti-CD25 antibody Simulect® (basiliximab) may be conveniently used as a negative control. Supernatant is taken after 16 h stimulation and assayed for IL-6 by ELISA. An IL-17 binding molecule typically has an $IC_{50}$ for inhibition of IL-6 production (in the presence 1 nM human IL-17) of about 50 nM or less (e.g., from about 0.01 to about 50 nM) when tested as above, i.e., said inhibitory activity being measured on IL-6 production induced by hu-IL-17 in human dermal fibroblasts. In some embodiments of the disclosed methods, regimens, kits, processes, uses and compositions, IL-17 binding molecules and functional derivatives thereof have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

The term "covalent modification" includes modifications of a polypeptide according to the present disclosure, e.g., of a specified sequence; or a fragment thereof with an organic proteinaceous or non-proteinaceous derivatizing agent, fusions to heterologous polypeptide sequences, and post-translational modifications. Covalent modified polypeptides, e.g., of a specified sequence, still have the ability to bind the human IL-17 or, e.g., inhibit IL-6 production of IL-17 induced human dermal fibroblasts by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see, e.g., T. E. Creighton, Proteins: Structure and Molecular Properties, W. H. Freeman & Co., San Francisco, pp. 79-86 (1983). Covalent modifications, e.g., include fusion proteins comprising a polypeptide according to the present disclosure, e.g., of a specified sequence and their amino acid sequence variants, such as immunoadhesins, and N-terminal fusions to heterologous signal sequences. A common example of a non-naturally occurring covalent modification is pegylation. In some embodiments of the disclosed methods, regimens, kits, processes, uses and compositions, the IL-17 binding molecules or IL-17 receptor binding molecules disclosed herein are covalently modified.

The phrase "substantially identical" means that the relevant amino acid or nucleotide sequence (e.g., CDR(s), $V_H$, or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region. In the case of antibodies, the second antibody has the same specificity and has at least 50% of the affinity of the same. Sequences substantially identical (e.g., at least about 85% sequence identity) to the sequences disclosed herein are also part of this application. In some embodiments, the sequence identity can be about 90% or greater, e.g., 90%, 91%, 92%, 93%, 94%, 95%, 96%, 97%, 98%, 99% or higher.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known.

The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The amino acids are identified by either the well known single-letter or three-letter designations.

The term "amino acid sequence variant" refers to molecules with some differences in their amino acid sequences as compared to the sequences according to the present disclosure. Amino acid sequence variants of a polypeptide according to the present disclosure, e.g., of a specified sequence, still have the ability to bind the human IL-17 or, e.g., inhibit IL-6 production of IL-17 induced human dermal fibroblasts. Substitutional variants are those that have at least one amino acid residue removed and a different amino acid inserted in its place at the same position in a polypeptide according to the present disclosure, e.g., of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present disclosure, e.g., of a specified sequence. Immediately adjacent to an amino acid means connected to either the α-carboxy or α-amino functional group of the amino acid. Deletional variants are those with one or more amino acids in a polypeptide according to the present disclosure, e.g., of a specified sequence, removed. Ordinarily, deletional variants will have one or two amino acids deleted in a particular region of the molecule.

As used herein, a "therapeutically effective amount" refers to an amount of an IL-17 antagonist (e.g.a., an IL-17 binding molecule (e.g., an IL-17 antibody, e.g., secukinumab) or IL-17 receptor binding molecule (e.g., an IL-17 receptor antibody)) that is effective, upon single or multiple dose administration to a subject (such as a human patient) at treating, preventing, curing, delaying, reducing the severity of, ameliorating at least one symptom of a disorder or recurring disorder, or prolonging the survival of the subject beyond that expected in the absence of such treatment. When applied to an individual active ingredient (e.g., an IL-17 binding molecule) administered alone, the term refers to that ingredient alone. When applied to a combination, the term refers to combined amounts of the active ingredients that result in the therapeutic effect, whether administered in combination, serially or simultaneously.

As used herein, the term "psoriasis" includes plaque-type, guttate, inverse, pustular, and erythrodermic psoriasis. A preferred type of psoriasis to be treated with the methods, regimens, combinations, kits and compositions disclosed herein, is plaque-type psoriasis.

The terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment.

The following definitions are used according to Committee for medicinal products for human use (GIMP), European Medicines Agency for the Evaluation of Medicines for Human Use. (2004) Guideline on clinical investigation of medicinal products indicated for the treatment of psoriasis. CHMP/EWP/2454/02 corr document. London, UK:

Treatment response (responder): Patients achieving ≥75% improvement (reduction) in Psoriasis Area and Severity Index (PAST) score compared to baseline (also referred to as PASI 75) are defined as treatment responders.

matory psoriasis occurring within 8 weeks of stopping therapy), e.g., a PASI of >125% of the value at baseline PASI.

In the PASI scoring system, the head, trunk, upper limbs and lower limbs are assessed separately for erythema, thickening (plaque elevation, induration), and scaling (desquamation) as defined in Table 1. The average degree of severity of each sign in each of the four body regions is assigned a score of 0 to 4. The area covered by lesions on each body region is estimated as a percentage of the total area of that particular body region. Because the head and neck, upper limbs, trunk and lower limbs correspond to approximately 10%, 20%, 30% and 40% of the body surface area, respectively, the PASI score is calculated using the formula:

$$PASI=0.1(EH+IH+DH)AH+0.2(EU+IU+DU)AU+0.3(ET+IT+DT)AT+0.4(EL+IL+DL)AL$$

PASI scores can range from a lower value of 0, corresponding to no signs of psoriasis, up to a theoretic maximum of 72.0. PASI scores are specific to a tenth of a point, e.g., 9.0, 10.1, 14.2, 17.3, etc. Further information on PASI scoring is available in Henseler T, Schmitt-Rau K (2008) Int. J. Dermatol.; 47: 1019-1023.

TABLE 1

The PASI Scoring System

| Body Region | Erythema (E) | Thickening (I) (plaque levation, induration) | Scaling (D) (desquamation) | Area score (A) (based on true area %)* |
|---|---|---|---|---|
| Head and neck (H) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Upper limbs (U) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Trunk, axillae and groin (T) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Lower limbs and buttocks (L) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |

Partial response (partial responder): Patients achieving a ≥50% improvement from baseline PASI score (also referred to as PASI 50) but less than 75% (also referred to as PASI 75) are defined as partial responders.

Non response (non-responder): Patients achieving a PASI reduction of <50% from baseline PASI score are defined as non-responders.

Relapse (relapser): If patients loose ≥50% of the PASI gain achieved during the previous time in the study, patients will be regarded as having a "relapse".

Rebound (rebounder): Worsening of the value at baseline PASI (or new pustular, erythrodermic or more inflam- As used herein, the phrase "start of relapse" (SoR) refers to the loss of 15%-25%, of the maximum drug response (compared to baseline) achieved at any time before the visit at which the assessment of start of relapse is made and loss of PASI 75. In some embodiments of the disclosed methods, uses and regimens, the psoriasis patient has experienced a SoR. In some embodiments of the disclosure, SoR refers to the loss of 20% of the maximum drug response (compared to baseline) achieved at any time before the visit at which the assessment of start of relapse is made and loss of PASI 75.

Table 2 provides several non-limiting examples of calculations determining whether a patient displays "start of relapse" ("SoR") using the PASI scoring system. The definition for SoR employed in Table 2 is loss of 20% of PASI gain and loss of PASI75 response. This definition allows patients having a high response (either an initial response or a response following SoR treatment) to continue without additional dosing even though they have lost 20% of the best improvement gain ever achieved (see Patient 5 in Table 2). With a responder such as Patient 5, SoR treatment will not be initiated until PASI75 is lost (value F for Patient 5), nor will it be continued until PASI75 is again lost (value K for Patient 5).

do not achieve at least PASI75 (compare value B to value $G_2$ for Patient 2).

In Table 2, it is also illustrated that a patient, once identified as experiencing SoR, will be treated with the IL-17 binding molecule, e.g., secukinumab, every 4 weeks until PASI75 (value B) is surpassed. In some cases, e.g., Patients 4-5, only a single dose of the IL-17 binding molecule, e.g., secukinumab, is required to again achieve

TABLE 2

Examples of Start of Relapse, wherein Start or Relapse is loss of 20% of PASI gain and loss of PASI75 response.

| Item | Patient 1 | Patient 2 | Patient 3 | Patient 4 | Patient 5 | Patient 6 |
|---|---|---|---|---|---|---|
| (A) Baseline PASI Score | 60.0 | 60.0 | 60.0 | 60.0 | 60.0 | 60.0 |
| (B) PASI75 score = ¼A | 15.0 | 15.0 | 15.0 | 15.0 | 15.0 | 15.0 |
| Benchmark Example | | | | | | |
| (C) Lowest PASI Score Ever Achieved | 30.0⊤ | 15.0 | 15.0 | 5.0 | 2.5 | 10.0 |
| (D) Best Improvement Gain Ever Achieved D = A − C | NA∞ | 45.0 | 45.0 | 55.0 | 57.5 | 50.0 |
| (E) 20% Best Improvement Gain Ever Achieved E = 20% (D) | NA∞ | 9.0 | 9.0 | 11.0 | 11.5 | 10.0 |
| (F) Start of relapse PASI score$^\Omega$ F = C + E if C + E > B F = B + 0.1$^\pounds$ if C + E < B | NA∞ | 24.0 | 24.0 | 16.0 | 15.1 * | 20.0 |
| SoR Treatment Example⁻ | | | | | | |
| ($G_1$) New PASI score following initial SoR treatment (G1). | NA∞ | 18.0 | 18.0 | 4.0 | 2.0 | 14.0 |
| ($G_2$) New PASI score following continued administration (if required) | NA∞ | 16.0 | 10.0 | NA¥ | NA¥ | NA¥ |
| (G) The lower of $G_1$ or $G_2$ or $G_1$ if $G_2$ is NA. | NA∞ | NA∞ | 10.0 ∮ | 4.0 ∮ | 2.0 ∮ | 14.0 |
| (H) New Improvement Gain H = A − G | NA∞ | NA∞ | 50.0 | 56.0 | 58.0 | 46.0 |
| (I) 20% New Improvement Gain I = 20% (H) | NA∞ | NA∞ | 10.0 | 11.2 | 11.6 | 9.2 |
| (J) Potential Next SoR PASI Score J = G + I if H > D J = F if H < D | NA∞ | NA∞ | 20.0 | 15.2 | 13.6 | 20.0 |
| (K) Next SoR PASI Score∮∮ K = J if J > B K = B + 0.1 if J < B | NA∞ | NA∞ | 20.0 | 15.2 | 15.1 | 20.0 |
| Further SoR Treatment . . . | | | | | | |

⊤ Not a candidate for SoR treatment because PASI75 not achieved (C > B).
∞ Not calculated because PASI75 not achieved (C > B).
$^\Omega$ When PASI score is greater than or equal to F, SoR Treatment is initiated.
$^\pounds$ The value B + 0.1 is used to reflect a score greater than PASI75 (B), because PASI scores are specific to the nearest 0.1 decimal point.
* In this example, because Patient 5 has responded very favorably to initial treatment, Patient 5 must loose PASI75 (i.e., have a PASI score of greater than 15 (B), e.g., 15.1) to enter SoR treatment.
⁻ Once SoR treatment has been initiated, a patient will be treated every 4 weeks until PASI75 (B) is achieved. Once PASI75 (B) is achieved, the patient will again become eligible for SoR Treatment.
¥ No continued administration is needed, since PASI75 was already achieved in $G_1$.
∮ In these examples, the new PASI (G) is better than the Lowest PASI Score Ever Achieved (C), and therefore G will become the new benchmark, i.e., the new Lowest PASI Score Ever Achieved.
∮∮ When PASI score is greater than or equal to K, Further SoR Treatment is initiated.

Table 2 illustrates, inter alia, that patients will not be eligible for SoR treatment until PASI75 is achieved (compare value B to value C for Patient 1). It also illustrates that some patients who initially receive SoR treatment will not again be eligible for continued SoR treatment, because they PASI75 (value $G_1$ for Patients 4-5). In other cases, e.g., Patient 3, more than one dose is required to again achieve PASI75 (value $G_2$ for Patient 3).

As shown in Table 2, once PASI75 is achieved during SoR treatment, a new calculation is undertaken to determine the next SoR PASI score (value K). In the case of Patients 3 and 4, because the new improvement gains (values H) following SoR treatment are the best improvement gain ever achieved (compare H to D for each patient), those new improvement gains (values H) will be used in determining a new SoR PASI score (value K). However, in some situations, e.g., Patient 6, the new improvement gain (value H) following SoR treatment will not be the best improvement gain ever achieved (compare H to D for Patient 6), and therefore the best improvement gain ever achieved (value D) will remain the benchmark in determining the next SoR PASI score (value K).

It will be understood that maximum response, improvement, gained improvement, lost improvement, SoR, etc., may be measured by any available scoring system, e.g., physician's assessed efficacy measures, such as PASI, visual assessment of index lesions, body surface measurement (BSA), clinical signs score: Total Severity Sign score (TSS), Physician's global assessment of improvement (PGA) or other global score (e.g., Investigators global assessment of improvement (IGA)); or patient's assessed efficacy measures, such as symptom improvement (pruritis, soreness), Patient's assessment of global improvement, Patient's assessment of PASI (self-administered PASI-SAPASI), or HRQL scales for dermatology (general scales, such as DLQI, DQOLS and specific psoriasis scales, such as PDI, PLSI)). In a preferred example, SoR is assessed using the PASI scoring system (physician assessed or patient assessed, preferably physician assessed).

If a patient has already displayed a SoR, and later displays another SoR, that subsequent relapse is referred to as an "additional start of relapse" or an "additional SoR". In some embodiments of the disclosure, the patient has experienced an additional SoR.

As used herein, the phrases "has been previously treated with a systemic agent for psoriasis" and "prior psoriasis treatment" are used to mean a patient that has previously undergone psoriasis treatment using a systemic agent, e.g., the patient is a non-responder, a responder, a relapser, a rebounder, or a partial responder. Such patients include those previously treated with biologics, such as efalizumab, and those previously treated with non-biologics, such as cyclosporine. As used herein, a patient having previously been treated for psoriasis with secukinumab is referred to as having undergone "prior secukinumab treatment". In some embodiments of the disclosure, the patient has been previously treated with a systemic agent for psoriasis.

As used herein, the phrase "has not been previously treated with a systemic agent for psoriasis" is used to mean a patient that has not previously undergone systemic psoriasis treatment. In some embodiments of the disclosure, the patient has not been previously treated with a systemic agent for psoriasis.

As used herein, the term "naïve" refers to patient that has not previously undergone systemic psoriasis treatment. In some embodiments of the disclosure, the patient is naïve.

By "therapeutic regimen" is meant the pattern of treatment of an illness, e.g., the pattern of dosing used during the treatment of psoriasis. A therapeutic regimen may include an induction regimen and a maintenance regimen. In some embodiments of the disclosure, the patient is given an induction regimen and a maintenance regimen of the IL-17 antagonist (e.g., IL-17 binding molecule, e.g., IL-17 antibody, e.g., secukinumab, or IL-17 receptor binding molecule, e.g., IL-17 receptor antibody). Table 3 gives examples of approved therapeutic regimens for treatment of psoriasis. Notably, none of these regimens provide for treatment at SoR.

TABLE 3

Examples of therapeutic regimens for biological treatment of psoriasis

| Standard | Route | Induction Regimen | Maintenance Regimen | Approved for any type of relapse treatment? |
|---|---|---|---|---|
| adalimumab | S.C. | 80 mg once | 40 mg every other week starting one week after initial dose | No |
| alefacept | I.M. or I.V. | 15 mg once weekly for 12 weeks | If the course is repeated there must be a gap of at least 12 weeks between courses | No |
| etanercept | S.C. | 50 mg twice weekly for 12 weeks | 50 mg weekly | No |
| infliximab | I.V. | 5 mg/kg weeks 0, 2, 6 | 5 mg/kg every 8 weeks | No |
| ustekinumab | S.C. | Weight ≤100 kg-45 mg initially and 4 weeks later Weight >100 kg-90 mg initially and 4 weeks later | 45 mg every 12 weeks 90 mg every 12 weeks | No |

The phrase "induction regimen" refers to a treatment regimen (or the portion of a treatment regimen) that is used for the initial treatment of a disease. During the treatment of psoriasis, the first 12 weeks of treatment is generally referred to as the "induction period", and it is during this time that an induction regimen is employed. The general goal of an induction regimen is to provide a high level of drug in the system of a patient during the induction period. An induction regimen may employ (in part or in whole) a "loading regimen", which may include administering a greater dose of the drug than a physician would employ during a maintenance regimen, administering a drug more frequently than a physician would administer the drug during a maintenance regimen, or both. Delivery of an IL-17 antagonist, e.g., an IL-17 binding molecule (e.g., an IL-17 antibody, such as secukinumab) or an IL-17 receptor binding molecule (e.g., an IL-17 receptor antibody) during an induction regimen may be via a subcutaneous route, e.g., delivery of dosages of about 75 mg-about 300 mg s.c., via an intravenous route, e.g., delivery of dosages of about 1 mg/kg-about 50 mg/kg i.v. (e.g., about 1 mg/kg, about 3 mg/kg, about 10 mg/kg, about 30 mg/kg, about 40 mg/kg, about 50 mg/kg, etc.) or any other route of administration (e.g, intramuscular, i.m.). In some embodiments, the dose of the IL-17 binding molecule (e.g., secukinumab) used during an induction regimen is about 150 mg or about 300 mg, which is delivered s.c.

An induction regimen for delivery of an IL-17 antagonist, e.g., an IL-17 binding molecule (e.g., an IL-17 antibody, such as secukinumab) or an IL-17 receptor binding molecule (e.g., an IL-17 receptor antibody) may also be designed using PK information (see Table 10), rather than specific dosages. For the disclosed regimens and methods, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide a mean trough level of about 29.2 µg/mL (with a 30-40% inter-patient variation). Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide a $C_{max}$ for a typical 90 kg patient of between about 52 µg/ml-about 104 µg/ml. In some embodiments, the IL-17 binding molecule (e.g., an IL-17 antibody, e.g., secukinumab) has a $T_{max}$ of about 7-8 days and an elimination half-life of about 30 days.

The phrase "maintenance regimen" refers to a treatment regimen (or the portion of a treatment regimen) that is used for the maintenance of a patient during treatment of an illness, e.g., to keep the patient in remission for longer periods of time (months or years). This time frame is referred to as a "maintenance period". A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, PASI score, etc.]). Delivery of an IL-17 antagonist, e.g., an IL-17 binding molecule (e.g., an IL-17 antibody, such as secukinumab) or an IL-17 receptor binding molecule (e.g., an IL-17 receptor antibody) during a maintenance regimen may be via a subcutaneous route, e.g., delivery of dosages of about 75 mg-about 300 mg s.c., via an intravenous route, e.g., delivery of dosages of about 1 mg/kg-about 50 mg/kg i.v. (e.g., about 1 mg/kg, about 3 mg/kg, about 10 mg/kg, about 30 mg/kg, about 40 mg/kg, about 50 mg/kg, etc.), or any other route of administration (e.g, intramuscular, i.m.). In some embodiments of the disclosed subject matter, the dose of the IL-17 binding molecule (e.g., secukinumab) used during a maintenance regimen is about 150 mg or about 300 mg (e.g., delivered s.c.). A dose may be delivered as one or more than one injection, e.g., a dose of 150 mg may be delivered as two injections of 75 mg and a dose of 300 mg may be delivered as two injections of 150 mg.

A maintenance regimen for delivery of an IL-17 antagonist, e.g., an IL-17 binding molecule (e.g., an IL-17 antibody, such as secukinumab) or an IL-17 receptor binding molecule (e.g., an IL-17 receptor antibody) may also be designed using PK information (see Table 10), rather than specific dosages. For the disclosed regimens and methods, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during a maintenance regimen to provide an average steady-state trough level of about 15 µg/mL (with a 30-40% inter-patient variation). Alternatively, an artisan may deliver an IL-17 binding molecule (e.g., an IL-17 antibody, e.g., secukinumab) during an induction regimen to provide an average steady-state trough level for a typical 90 kg patient of between about 5 µg/ml-about 70 µg/ml, e.g., about 5 µg/ml-about 33 µg/ml or about 11 µg/ml-about 70 µg/ml, preferably about 16 µg/ml or about 33 µg/ml. In some embodiments, the IL-17 binding molecule (e.g., an IL-17 antibody, e.g., secukinumab) has a $T_{max}$ of about 7-8 days. In some embodiments, the IL-17 binding molecule (e.g., an IL-17 antibody, e.g., secukinumab) has an elimination half-life of about 30 days.

In one embodiment, the maintenance regimen employs administration of at least one (e.g., one or two doses) of the drug, e.g., a single dose of secukinumab, upon manifestation of predefined response criteria (e.g., PASI scores or clinical signs indicating SoR). Such therapy is known as intermittent therapy (e.g., as compared to continuous therapy); a form of intermittent therapy is treatment at SoR. Administering secukinumab at SoR may be followed by monitoring the patient (or by the patient self-monitoring) for achievement of a predefined response criteria (e.g., PASI75). If the patient does not achieve the predefined response criteria following SoR treatment, then the patient may continue treatment with the IL-17 antagonist, e.g., an IL-17 binding molecule (e.g., an IL-17 antibody, such as secukinumab) or an IL-17 receptor binding molecule (e.g., an IL-17 receptor antibody) until that predefined response criteria is achieved. If the patient does achieve the predefined response criteria following SoR treatment, then treatment will be discontinued until an additional SoR occurs. If the patient manifests a score indicative of an additional SoR, the patient may then be administered (or may self-administer) at least one (e.g., one or two) dose of secukinumab, e.g., another single dose of secukinumab. This process will repeat during SoR therapy. It will be recognized that treatment at SoR provides a unique approach to psoriasis management, as it maintains the lowest level of drug exposure possible to achieve a clinically meaningful response, while allowing a patient to experience a completely individualized therapy.

Accordingly, in some embodiments, a maintenance regimen may employ administration of the IL-17 antagonist, e.g., an IL-17 binding molecule (e.g., an IL-17 antibody, such as secukinumab) or an IL-17 receptor binding molecule (e.g., an IL-17 receptor antibody) until a given endpoint is met, e.g, achievement of PASI75. In further embodiments, the maintenance regimen comprises treating the patient with a dose of about 75 mg-about 300 mg of the IL-17 binding molecule at start of relapse and thereafter treating the patient monthly with a dose of about 75 mg-about 300 mg of the IL-17 binding molecule until PASI75 is achieved.

In some embodiments, once a patient experiences SoR (e.g., loss of 20% of the maximum response achieved at any time before the visit at which the assessment of SoR is made and loss of PASI 75), the patient will be administered at least one (e.g., one, two, three, four, or more) dose of the IL-17 binding molecule (e.g., secukinumab), e.g., in monthly doses (every 4 weeks), which will continue until the pre-defined response criteria (e.g., PASI75) is again achieved. In another embodiment, once a patient experiences SoR (e.g., loss of 20% of the maximum response achieved at any time before the visit at which the assessment of SoR is made and loss of PASI 75), the patient is administered at least one dose (e.g., one, two, three, four, or more) of about 75 mg to about 300 mg (e.g., about 75 mg, about 150 mg, about 300 mg, preferably about 150 mg or about 300 mg) of the IL-17 binding molecule (e.g., IL-17 antibody, e.g, secukinumab) monthly until PASI75 is achieved. In some embodiments, the IL-17 binding molecule is administered to the patient shortly after SoR is diagnosed (e.g., 1, 2, 3, 4, 5, 6, 7, 10, 14, 21 days), and is thereafter administered on a monthly basis until PASI75 is achieved. In other embodiments, a patient identified as displaying SoR will be administered the IL-17 binding molecule at the next scheduled appointment and thereafter the patient will be administered the IL-17 binding molecule on a monthly basis until PASI75 is achieved.

As used herein, "identifying a patient at start of relapse", "identify a patient at start of relapse", and the like, means that a patient, due to manifestation of a certain predetermined score, e.g., a PASI score, is recognized by a physician as displaying a SoR. In some embodiments, the disclosed methods, regimens, and uses provide for identifying a patient at SoR.

The timing of dosing is generally measured from the day of the first dose of secukinumab (which is also known as "baseline"). However, health care providers often use different naming conventions to identify dosing schedules, as shown in Table 4.

TABLE 4

Common naming conventions for dosing regimens. Bolded items refer to the naming convention used herein.

| Week | 0/1 | 1/2 | 2/3 | 3/4 | 4/5 | 5/6 | 6/7 | 7/8 | 8/9 | 9/10 | 10/11 | etc |
|---|---|---|---|---|---|---|---|---|---|---|---|---|
| 1st day of week | 0/1 | 7/8 | 14/15 | 21/22 | 28/29 | 35/36 | 42/43 | 49/50 | 56/57 | 63/64 | 70/71 | etc. |

Notably, week zero may be referred to as week one by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the IL-17 binding molecule regardless of whether the physician refers to a particular week as "week 1" or "week 2". As an example of naming using the convention designated herein, five loading doses of secukinumab administered weekly during an induction regimen may be provided during week 0 (e.g., on about day 1), during week 1 (e.g., on about day 8), during week 2 (e.g., on about day 15), during week 3 (e.g., on about day 22), and during week 4 (e.g., on about day 29). This portion of an induction regimen is also referred to as "weekly for five weeks". Loading doses may be administered every two weeks (i.e., every other week), e.g., during week 0, during week 2, during week 4, etc. Loading doses may be administered every three weeks, e.g., during week 0, during week 3, during week 6, etc. Loading doses may be administered daily for one week, e.g., on day 1-7.

During an induction regimen, an additional dose of secukinumab may be provided at around day 57 (during week 8). This portion of an induction regimen is referred to as "monthly" and this time point is referred to as being "during week eight". Loading doses may also be administered every week (e.g., during week 0, 1, 2, 3, 4, etc.) or every other week, (e.g., during week 0, 2, 4, 6, 8, 10 etc.) Alternatively, a loading dose may be delivered as a single high dose infusion (e.g., about 10 mg/kg, about 30 mg/kg) during the first month, and thereafter monthly s.c. injections may be administered (e.g., during week 4 and during week 8, etc.). Alternatively, a loading dose may be delivered as more than one high dose infusion (e.g., 3 doses of about 10 mg/kg) during the first month, and thereafter monthly s.c. injections may be administered. It will be understood that a dose need not be provided at an exact time point, e.g., a dose due on day 57 could be provided, e.g., on day 52 to day 62 (+/−5 days). In preferred embodiments, the induction regimen employs dosing weekly for five weeks (week 0, 1, 2, 3, and 4), followed by a monthly dose during week 8.

For a maintenance regimen, a dose may be provided every month (also called "monthly" dosing) (i.e., every 4 weeks, i.e., about every 28 days), every two months (i.e., every 8 weeks, i.e., about every 56 days), or every three months (i.e., every 12 weeks, i.e., about every 84 days). As used herein, the first dose of a maintenance regimen employing continuous therapy will be administered on a date measured from the final dose of the induction regimen. Thus, as an example, if the final dose of the induction regimen is provided during week 8, then the first dose as part of a monthly maintenance regimen will be delivered during week 12, the first dose as part of an every two month maintenance regimen will be delivered during week 16, the first dose as part of an every three month maintenance regimen will be delivered during week 20, etc. In preferred embodiments, the maintenance regimen employs monthly dosing beginning on week 12.

As used herein, the phrase "means for administering" is used to indicate any available implement for systemically administering a biologic, including, but not limited to, a pre-filled syringe, a vial and syringe, an injection pen, an autoinjector, an i.v. drip and bag, a patch, a gel, a pump, etc. With such items, a patient may self-administer the drug (i.e., administer the drug on their own behalf) or a physician may administer the drug.

In some embodiments, the IL-17 antagonist, e.g., IL-17 binding molecule (e.g., IL-17 antibody, e.g, secukinumab) or IL-17 receptor binding molecule (e.g., IL-17 receptor antibody) may be administered as a dose of about 150 mg at weeks 0, 1, 2, 3, 4, and 8 followed by about 150 mg every month (i.e., every 4 weeks) thereafter as a continuous maintenance therapy. In some embodiments, the IL-17 antagonist, e.g., IL-17 binding molecule (e.g., IL-17 antibody, e.g, secukinumab) or IL-17 receptor binding molecule (e.g., IL-17 receptor antibody) may be administered as a dose of about 300 mg at weeks 0, 1, 2, 3, 4, and 8 followed by about 300 mg every month (i.e., every 4 weeks) thereafter as a continuous maintenance therapy. In further embodiments, once a satisfactory response is achieved, the IL-17 antagonist, e.g., IL-17 binding molecule (e.g., IL-17 antibody, e.g, secukinumab) or IL-17 receptor binding molecule (e.g., IL-17 receptor antibody) may be discontinued and subsequent relapse managed with reintroduction of the IL-17 antagonist, e.g., IL-17 binding molecule (e.g., IL-17 antibody, e.g, secukinumab) or IL-17 receptor binding molecule (e.g., IL-17 receptor antibody) at the previous effective dose as soon as a SoR or other loss of response is detected.

In some embodiments, a booster dose may be employed during therapy with the IL-17 antagonist, e.g., IL-17 binding molecule (e.g., IL-17 antibody, e.g, secukinumab) or IL-17 receptor binding molecule (e.g., IL-17 receptor antibody). A "booster dose", as used herein, refers to a dose (or several doses) of an IL-17 antagonist, e.g., IL-17 binding molecule (e.g., IL-17 antibody, e.g, secukinumab) or IL-17 receptor binding molecule (e.g., IL-17 receptor antibody) that is greater than the standard doses delivered during psoriasis therapy with the IL-17 binding molecule. For example, the dose of the IL-17 antagonist, e.g., IL-17 binding molecule (e.g., IL-17 antibody, e.g, secukinumab) or IL-17 receptor binding molecule (e.g., IL-17 receptor antibody) may be escalated for patients who do not respond or who are partial responders during an induction period. Thus, a patient having been treated with 150 mg of IL-17 binding molecule during week 0, 1, 2, 3, and 8 may be provided with about 300 mg of the IL-17 binding molecule during week 12, and if the patient is then converted to a responder, the patient will thereafter be treated with doses of 150 mg. Alternatively, a physician may deliver a booster dose during week 16 (i.e., rather than during week 12). In some embodiments, a physician may employ one or more booster doses (e.g., a single booster dose at week 12 and thereafter standard doses, a booster dose at week 12 and 16 and thereafter standard doses, etc.). In some embodiments, if the original dose was 150 mg, the booster will be, e.g., about 300 mg or at least about 10 mg/kg (e.g., about 10 mg/kg given 1, 2, 3, 4 or 5 times [e.g., twice a week, every week, every two weeks, every three weeks, etc.]; about 15 mg/kg given 1, 2, 3, 4 or 5 times [e.g., twice a week, every week, every two weeks, every three weeks, etc.]; about 20 mg/kg given 1, 2, 3, 4 or 5 times [e.g., twice a week, every week, every two weeks, every three weeks, etc.]; about 30 mg/kg given 1, 2, 3, 4 or 5 times [e.g., twice a week, every week, every two weeks, every three weeks, etc.], etc.). In some embodiments, if the original dose was 300 mg, the booster will be, e.g., at least about 10 mg/kg e.g., about 10 mg/kg given 1, 2, 3, 4 or 5 times [e.g., twice a week, every week, every two weeks, every three weeks, etc.]; about 15 mg/kg given 1, 2, 3, 4 or 5 times [e.g., twice a week, every week, every two weeks, every three weeks, etc.]; about 20 mg/kg given 1, 2, 3, 4 or 5 times [e.g., twice a week, every week, every two weeks, every three weeks, etc.]; about 30 mg/kg given 1, 2, 3, 4 or 5 times [e.g., twice a week, every week, every two weeks, every three weeks, etc.], etc.). In some embodiments, a partial responder or a non-responder is provided booster doses for 4-8 weeks following the induction period.

In some embodiments, the maintenance regimen comprises treating the patient with a booster dose of the IL-17 binding molecule that is higher than the dose of the IL-17 binding molecule employed during the induction regimen if the patient is a partial responder or a non-responder during the induction regimen.

In a preferred embodiment, the methods and uses of the IL-17 binding molecule provide treatment of moderate to severe chronic plaque-type psoriasis in adult patients who are candidates for systemic therapy (or phototherapy). It is also expected that the methods and uses herein will provide relief (i.e., reduction) from various signs and symptoms of psoriasis, including, e.g., psoriasis-related itching, flaking, peeling, cracking, pain, scaling and redness.

IL-17 Binding Molecules

The various disclosed pharmaceutical compositions, regimens uses, methods and kits utilize an IL-17 antagonist, e.g., IL-17 binding molecule (e.g., IL-17 antibody, e.g, secukinumab) or IL-17 receptor binding molecule (e.g., IL-17 receptor antibody), such as secukinumab.

In one embodiment, the IL-17 binding molecule comprises at least one immunoglobulin heavy chain variable domain ($V_H$) comprising in sequence hypervariable regions CDR1, CDR2 and CDR3, said CDR1 having the amino acid sequence SEQ ID NO:1 (N-Y-W-M-N), said CDR2 having the amino acid sequence SEQ ID NO:2 (A-I-N-Q-D-G-S-E-K-Y-Y-V-G-S-V-K-G), and said CDR3 having the amino acid sequence SEQ ID NO:3 (D-Y-Y-D-I-L-T-D-Y-Y-I-H-Y-W-Y-F-D-L).

In one embodiment, the IL-17 binding molecule comprises at least one immunoglobulin heavy chain variable domain ($V_H$) comprising in sequence hypervariable regions CDR1-x, CDR2-x and CDR3-x, said CDR1-x having the amino acid sequence SEQ ID NO:11 (G-F-T-F-S-N-Y-W-M-N), said CDR2-x having the amino acid sequence SEQ ID NO:12 (A-I-N-Q-D-G-S-E-K-Y-Y), and said CDR3-x having the amino acid sequence SEQ ID NO:13 (C-V-R-D-Y-Y-D-I-L-T-D-Y-Y-I-H-Y-W-Y-F-D-L-W-G).

In one embodiment, the IL-17 binding molecule comprises at least one immunoglobulin light chain variable domain ($V_L$) comprising in sequence hypervariable regions CDR1', CDR2' and CDR3', said CDR1' having the amino acid sequence SEQ ID NO:4 (R-A-S-Q-S-V-S-S-S-Y-L-A), said CDR2' having the amino acid sequence SEQ ID NO:5 (G-A-S-S-R-A-T) and said CDR3' having the amino acid sequence SEQ ID NO:6 (Q-Q-Y-G-S-S-P-C-T).

In one embodiment, the IL-17 binding molecule comprises at least one immunoglobulin $V_H$ domain and at least one immunoglobulin $V_L$ domain, wherein: a) the immunoglobulin $V_H$ domain comprises: i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the immunoglobulin $V_L$ domain comprises hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 binding molecule (e.g., IL-17 antibody, e.g., secukinumab) comprises at least one immunoglobulin $V_H$ domain and at least one immunoglobulin $V_L$ domain, wherein: a) the at least one immunoglobulin $V_H$ domain comprises in sequence hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) the at least one immunoglobulin $V_L$ domain comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 binding molecule (e.g., IL-17 antibody, e.g., secukinumab) comprises at least one immunoglobulin $V_H$ domain and at least one immunoglobulin $V_L$ domain, wherein: a) the at least one immunoglobulin $V_H$ domain comprises in sequence hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the at least one immunoglobulin $V_L$ domain comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 binding molecule comprises:
a) an immunoglobulin heavy chain variable domain ($V_H$) comprising the amino acid sequence set forth as SEQ ID NO:8;
b) an immunoglobulin light chain variable domain ($V_L$) comprising the amino acid sequence set forth as SEQ ID NO:10;
c) an immunoglobulin $V_H$ domain comprising the amino acid sequence set forth as SEQ ID NO:8 and an immunoglobulin $V_L$ domain comprising the amino acid sequence set forth as SEQ ID NO:10;
d) an immunoglobulin $V_H$ domain comprising the hypervariable regions set forth as SEQ ID NO:1, SEQ ID NO:2, and SEQ ID NO:3;
e) an immunoglobulin $V_L$ domain comprising the hypervariable regions set forth as SEQ ID NO:4, SEQ ID NO:5 and SEQ ID NO:6;
f) an immunoglobulin $V_H$ domain comprising the hypervariable regions set forth as SEQ ID NO:11, SEQ ID NO:12 and SEQ ID NO:13;
g) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; or
h) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

The amino acid sequences of the hypervariable regions of secukinumab, based on the Kabat definition and as determined by the X-ray analysis and using the approach of Chothia and coworkers, is provided in Table 5.

Interest", Kabat E. A. et al, US Department of Health and Human Services, Public Health Service, National Institute of Health.

In some embodiments, an IL-17 binding molecule of the disclosure comprises the variable light domain of SEQ ID NO:10. In other embodiments, an IL-17 binding molecule of the disclosure comprises the variable heavy domain of SEQ ID NO:8. In other embodiments, an IL-17 binding molecule of the disclosure comprises the variable light domain of SEQ ID NO:10 and the variable heavy domain of SEQ ID NO:8. In some embodiments, an IL-17 binding molecule of the disclosure comprises the three CDRs of SEQ ID NO:10. In other embodiments, an IL-17 binding molecule of the disclosure comprises the three CDRs of SEQ ID NO: 8. In other embodiments, an IL-17 binding molecule of the disclosure comprises the three CDRs of SEQ ID NO:10 and the three CDRs of SEQ ID NO:8. CDRs of SEQ ID NO:8 and SEQ ID NO:10, according to both the Chothia and Kabat definition, may be found in Table 5.

In some embodiments, an IL-17 binding molecule of the disclosure comprises the light domain of SEQ ID NO:15. In other embodiments, an IL-17 binding molecule of the disclosure comprises the heavy domain of SEQ ID NO:17. In other embodiments, an IL-17 binding molecule of the disclosure comprises the light domain of SEQ ID NO:15 and the heavy domain of SEQ ID NO:17. In some embodiments, an IL-17 binding molecule of the disclosure comprises the three CDRs of SEQ ID NO:15. In other embodiments, an IL-17 binding molecule of the disclosure comprises the three CDRs of SEQ ID NO:17. In other embodiments, an IL-17 binding molecule of the disclosure comprises the three CDRs of SEQ ID NO:15 and the three CDRs of SEQ ID NO:17. CDRs of SEQ ID NO:15 and SEQ ID NO:17, according to both the Chothia and Kabat definition, may be found in Table 5.

TABLE 5

Amino acid sequences of the hypervariable regions of the secukinumab monoclonal antibodies. Amino acid highlighted in bold are part of the CDR loops, while those shown in plain style are part of the antibody framework.

Light-chain

| | | |
|---|---|---|
| CDR1' | Kabat definition | R-A-S-Q-S-V-S-S-S-Y-L-A (SEQ ID NO: 4) |
| | Chothia/X-ray definition | R-A-S-Q-S-V-S-S-S-Y-L-A (SEQ ID NO: 4) |
| CDR2' | Kabat definition | G-A-S-S-R-A-T (SEQ ID NO: 5) |
| | Chothia/X-ray definition | G-A-S-S-R-A-T (SEQ ID NO: 5) |
| CDR3' | Kabat definition | Q-Q-Y-G-S-S-P-C-T (SEQ ID NO: 6) |
| | Chothia/X-ray definition | Q-Q-Y-G-S-S-P-C-T (SEQ ID NO: 6) |

Heavy-chain

| | | |
|---|---|---|
| CDR1 | Kabat definition | N-Y-W-M-N (SEQ ID NO: 1) |
| CDR1-x | Chothia/X-ray definition | G-F-T-F-S-N-Y-W-M-N (SEQ ID NO: 11) |
| CDR2 | Kabat definition | A-I-N-Q-D-G-S-E-K-Y-Y-V-G-S-V-K-G (SEQ ID NO: 2) |
| CDR2-x | Chothia/X-ray definition | A-I-N-Q-D-G-S-E-K-Y-Y (SEQ ID NO: 12) |
| CDR3 | Kabat definition | D-Y-Y-D-I-L-T-D-Y-Y-I-H-Y-W-Y-F-D-L (SEQ ID NO: 3) |
| CDR3-x | Chothia/X-ray definition | C-V-R-D-Y-Y-D-I-L-T-D-Y-Y-I-H-Y-W-Y-F-D-L-W-G (SEQ ID NO: 13) |

In preferred embodiments, the variable domains of both heavy and light chains are of human origin, for instance those of the secukinumab antibody which are shown in SEQ ID NO:10 (=variable domain of light chain, i.e., amino acid 1 to 109 of SEQ ID NO:10) and SEQ ID NO:8 (=variable domain of heavy chain, i.e., amino acid 1 to 127 of SEQ ID NO:8). The constant region domains preferably also comprise suitable human constant region domains, for instance as described in "Sequences of Proteins of Immunological Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, an IL-17 binding molecule is selected from a human anti-IL-17 antibody that comprises at least: a) an immunoglobulin heavy chain or fragment thereof which comprises a variable domain comprising in sequence the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof which comprises a variable domain comprising in sequence the hypervariable regions and optionally also the CDR1', CDR2', and CDR3' hypervariable regions and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO:6.

In one embodiment, an IL-17 binding molecule is selected from a single chain binding molecule which comprises an antigen binding site comprising: a) a first domain comprising in sequence the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO: 3; and b) a second domain comprising the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, an IL-17 binding molecule may comprise at least one antigen binding site comprising at least one immunoglobulin heavy chain variable domain ($V_H$) which comprises in sequence: a) hypervariable regions CDR1 (SEQ ID NO: 1), CDR2 (SEQ ID NO: 2) and CDR3 (SEQ ID NO: 3); or b) hypervariable regions $CDR1_i$, $CDR2_i$, $CDR3_i$, said hypervariable region CDR1, differs by 3, preferably 2, more preferably 1 amino acid(s) from the hypervariable region of CDR1 as shown in SEQ ID NO: 1, said hypervariable region CDR2, differs by 3, preferably 2, more preferably 1 amino acid(s) from the hypervariable region of CDR2 as shown in SEQ ID NO: 2; and said hypervariable region CDR3, differs by 3, preferably 2, more preferably 1 amino acid(s) from the hypervariable region of CDR3 as shown in SEQ ID NO: 3; and said binding IL-17 molecule is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Similarly, an IL-17 binding molecule may comprise at least one antigen binding site comprising at least one immunoglobulin heavy chain variable domain ($V_H$) which comprises in sequence: a) hypervariable regions CDR1-x (SEQ ID NO: 11), CDR2-x (SEQ ID NO: 12) and CDR3-x (SEQ ID NO: 13); or b) hypervariable regions $CDR1_i$-x, $CDR2_i$-x, $CDR3_i$-x, said hypervariable region $CDR1_i$-x differs by 3, preferably 2, more preferably 1 amino acid(s) from the hypervariable region of CDR1-x as shown in SEQ ID NO: 11, said hypervariable region $CDR2_i$-x differs by 3, preferably 2, more preferably 1 amino acid(s) from the hypervariable region of CDR2-x as shown in SEQ ID NO: 12; and said hypervariable region $CDR3_i$-x differs by 3, preferably 2, more preferably 1 amino acid(s) from the hypervariable region of CDR3-x as shown in SEQ ID NO: 13; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Similarly, an IL-17 binding molecule may comprise at least one antigen binding site comprising at least one immunoglobulin light chain variable domain ($V_L$) which comprises in sequence: a) hypervariable regions CDR'1 (SEQ ID NO: 4), CDR'2 (SEQ ID NO: 5) and CDR'3 (SEQ ID NO: 6); or b) hypervariable regions $CDR'1_i$, $CDR'2_i$, $CDR'3_i$, said hypervariable region $CDR'1_i$ differs by 3, preferably 2, more preferably 1 amino acid(s) from the hypervariable region of CDR'1 as shown in SEQ ID NO: 4, said hypervariable region $CDR'2_i$ differs by 3, preferably 2, more preferably 1 amino acid(s) from the hypervariable region of CDR'2 as shown in SEQ ID NO: 5; and said hypervariable region $CDR'3_i$ differs by 3, preferably 2, more preferably 1 amino acid(s) from the hypervariable region of CDR'3 as shown in SEQ ID NO: 6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Alternatively, an IL-17 binding molecule may comprise both heavy ($V_H$) and light chain (VL) variable domains and said IL-17 binding molecule having at least one antigen binding site comprising: a) an immunoglobulin heavy chain variable domain ($V_H$) which comprises in sequence hypervariable regions CDR1 (SEQ ID NO: 1), CDR2 (SEQ ID NO: 2) and CDR3 (SEQ ID NO: 3); and an immunoglobulin light chain variable domain ($V_L$) which comprises in sequence hypervariable regions CDR1' (SEQ ID NO: 4), CDR2' (SEQ ID NO: 5) and CDR3' (SEQ ID NO: 6); or b) an immunoglobulin heavy chain variable domain ($V_H$) which comprises in sequence hypervariable regions $CDR1_i$, $CDR2_i$, and $CDR3_i$, said hypervariable region $CDR1_i$ differs by 3, preferably 2, more preferably 1 amino acid(s) from the hypervariable region of CDR1 as shown in SEQ ID NO: 1, said hypervariable region $CDR2_i$ differs by 3, preferably 2, more preferably 1 amino acid(s) from the hypervariable region of CDR2 as shown in SEQ ID NO: 2; and said hypervariable region $CDR3_i$ differs by 3, preferably 2, more preferably 1 amino acid(s) from the hypervariable region of CDR3 as shown in SEQ ID NO: 3; and an immunoglobulin light chain variable domain ($V_L$) which comprises in sequence hypervariable regions $CDR'1_i$, $CDR'2_i$, $CDR'3_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Alternatively, an IL-17 binding molecule may comprise both heavy ($V_H$) and light chain (VL) variable domains and said IL-17 binding molecule comprises at least one antigen binding site comprising: a) an immunoglobulin heavy chain variable domain ($V_H$) which comprises in sequence hypervariable regions CDR1-x (SEQ ID NO:11), CDR2-x (SEQ ID NO:12) and CDR3-x (SEQ ID NO:13); and an immunoglobulin light chain variable domain ($V_L$) which comprises in sequence hypervariable regions CDR1' (SEQ ID NO: 4), CDR2' (SEQ ID NO: 5) and CDR3' (SEQ ID NO:6); or b) an immunoglobulin heavy chain variable domain ($V_H$) which comprises in sequence hypervariable regions CDR1$_i$-x, CDR2$_i$-x, and CDR3$_i$-x, said hypervariable region hypervariable regions CDR1$_i$-x, CDR2$_i$-x, CDR3$_i$-x, said hypervariable region CDR1$_i$-x differs by 3, preferably 2, more preferably 1 amino acid(s) from the hypervariable region of CDR1-x as shown in SEQ ID NO: 11, said hypervariable region CDR2$_i$-x differs by 3, preferably 2, more preferably 1 amino acid(s) from the hypervariable region of CDR2-x as shown in SEQ ID NO: 12; and said hypervariable region CDR3$_i$-x differs by 3, preferably 2, more preferably 1 amino acid(s) from the hypervariable region of CDR3-x as shown in SEQ ID NO: 13; and an immunoglobulin light chain variable domain ($V_L$) which comprises in sequence hypervariable regions CDR1'$_i$, CDR2'$_i$, CDR3'$_i$, said hypervariable region CDR1'$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO:5; and said hypervariable region CDR'3$_i$ differs by 3, preferably 2, more preferably 1 amino acid(s) from the hypervariable region of CDR'3 as shown in SEQ ID NO: 6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

A human IL-17 antibody disclosed herein may comprise a heavy chain that is substantially identical to that set forth as SEQ ID NO:17 and a light chain that is substantially identical to that set forth as SEQ ID NO:15. A human IL-17 antibody disclosed herein may comprise a heavy chain that comprises SEQ ID NO:17 and a light chain that comprises SEQ ID NO:15.

A human IL-17 antibody disclosed herein may comprise: a) one heavy chain which comprises a variable domain having an amino acid sequence substantially identical to that shown in SEQ ID NO:8 and the constant part of a human heavy chain; and b) one light chain which comprises a variable domain having an amino acid sequence substantially identical to that shown in SEQ ID NO:10 and the constant part of a human light chain.

The inhibition of the binding of IL-17 to its receptor may be conveniently tested in various assays including such assays as described in WO 2006/013107. By the term "to the same extent" is meant that the reference and the equivalent molecules exhibit, on a statistical basis, essentially identical IL-17 inhibitory activity in one of the assays referred to herein (see Example 1 of WO 2006/013107). For example, IL-17 binding molecules of the disclosure typically have $IC_{50}$s for the inhibition of human IL-17 on IL-6 production induced by human IL-17 in human dermal fibroblasts which are below about 10 nM, more preferably about 9, 8, 7, 6, 5, 4, 3, 2, or about 1 nM of that of, preferably substantially the same as, the $IC_{50}$ of the corresponding reference molecule when assayed as described in Example 1 of WO 2006/013107. Alternatively, the assay used may be an assay of competitive inhibition of binding of IL-17 by soluble IL-17 receptors (e.g. the human IL-17 R/Fc constructs of Example 1 of WO 2006/013107) and the IL-17 binding molecules of the disclosure.

The disclosure also includes IL-17 binding molecules in which one or more of the amino acid residues of CDR1, CDR2, CDR3, CDR1-x, CDR2-x, CDR3-x, CDR1', CDR2' or CDR3' or the frameworks, typically only a few (e.g., 1-4), are changed; for instance by mutation, e.g., site directed mutagenesis of the corresponding DNA sequences. The disclosure includes the DNA sequences coding for such changed IL-17 binding molecules. In particular the disclosure includes IL-17 binding molecules in which one or more residues of CDR1' or CDR2' have been changed from the residues shown in SEQ ID NO:4 (for CDR1') and SEQ ID NO:5 (for CDR2').

The disclosure also includes IL-17 binding molecules that have binding specificity for human IL-17, in particular IL-17 antibodies capable of inhibiting the binding of IL-17 to its receptor and IL-17 antibodies capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50% (said inhibitory activity being measured on IL-6 production induced by hu-IL-17 in human dermal fibroblasts).

In some embodiments, the IL-17 binding molecule, e.g., IL-17 antibody, e.g., secukinumab, binds to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (ie., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 µM. In some embodiments, the IL-17 antibody has an $IC_{50}$ of about 0.4 nM for in vitro neutralization of the biological activity of about 0.67 nM human IL-17A. In some embodiments, the IL-17 antibody has an in vivo half-life of about 4 weeks (e.g., about 23 to about 30 days). In some embodiments, the absolute bioavailability of subcutaneously (s.c.) administered IL-17 antibody has a range of about 60-about 80%, e.g., about 76%.

Particularly preferred IL-17 binding molecules of the disclosure are human antibodies, especially secukinumab, as described in Examples 1 and 2 of WO 2006/013107. Secukinumab (AIN457) is a recombinant high-affinity, fully human monoclonal anti-human interleukin-17A (IL-17A, IL-17) antibody of the IgG1/kappa isotype that is currently in clinical trials for the treatment of immune-mediated inflammatory conditions.

Treatment Regimens, Methods of Treatment, Pharmaceutical Compositions and Uses

The disclosed IL-17 antagonists, e.g., IL-17 binding molecules, e.g., an IL-17 antibody, such as secukinumab, are useful for the treatment, prevention, or amelioration of psoriasis.

The IL-17 antagonists, e.g., IL-17 binding molecules, e.g., an IL-17 antibody, such as secukinumab, may be used in vitro, ex vivo, or incorporated into pharmaceutical compositions and administered to individuals (e.g., human subjects) in vivo to treat, ameliorate, or prevent psoriasis. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

The IL-17 antagonists, e.g., IL-17 binding molecules, e.g., an IL-17 antibody, such as secukinumab, may be used as a pharmaceutical composition when combined with a pharmaceutically acceptable carrier. Such a composition may contain, in addition to an IL-17 binding molecule, carriers, various diluents, fillers, salts, buffers, stabilizers, solubilizers, and other materials well known in the art. The characteristics of the carrier will depend on the route of administration.

The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the IL-17 binding molecules, or to minimize side effects caused by the IL-17 binding molecules.

The pharmaceutical composition of the disclosure may be in the form of a liposome in which the IL-17 binding molecule is combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, etc.

In practicing the method of treatment or use of the present disclosure, a therapeutically effective amount of an IL-17 binding molecule is administered to a subject, e.g., a mammal (e.g., a human). An IL-17 binding molecule may be administered in accordance with the method of the disclosure either alone or in combination with other therapies, such as, e.g., in combination with additional therapies for inflammation. When coadministered with one or more agents, an IL-17 binding molecule may be administered either simultaneously with the other agent, or sequentially. If administered sequentially, the attending physician will decide on the appropriate sequence of administering the IL-17 binding molecule in combination with other agents.

When a therapeutically effective amount of an IL-17 binding molecule is administered orally, the binding agent will be in the form of a tablet, capsule, powder, solution or elixir. When administered in tablet form, the pharmaceutical composition of the disclosure may additionally contain a solid carrier such as a gelatin or an adjuvant. When administered in liquid form, a liquid carrier such as water, petroleum, oils of animal or plant origin such as peanut oil (exercising caution in relation to peanut allergies), mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol.

When a therapeutically effective amount of an IL-17 binding molecule is administered by intravenous, cutaneous or subcutaneous injection, the IL-17 binding molecule will be in the form of a pyrogen-free, parenterally acceptable solution. A pharmaceutical composition for intravenous, cutaneous, or subcutaneous injection may contain, in addition to the IL-17 binding molecule, an isotonic vehicle such as sodium chloride injection, Ringer's injection, dextrose injection, dextrose and sodium chloride injection, lactated Ringer's injection, or other vehicle as known in the art.

Pharmaceutical compositions for use in the disclosed methods may be manufactured in conventional manner. In one embodiment, the pharmaceutical composition is preferably provided in lyophilized form. For immediate administration it is dissolved in a suitable aqueous carrier, for example sterile water for injection or sterile buffered physiological saline. If it is considered desirable to make up a solution of larger volume for administration by infusion rather than a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

The appropriate dosage will, of course, vary depending upon, for example, the particular IL-17 binding molecule to be employed, the host, the mode of administration and the nature and severity of the condition being treated, and on the nature of prior treatments that the patient has undergone. Ultimately, the attending physician will decide the amount of the IL-17 binding molecule with which to treat each individual subject. In some embodiments, the attending physician may administer low doses of the IL-17 binding molecule and observe the subject's response. In other embodiments, the initial dose(s) of IL-17 binding molecule administered to a subject are high, and then are titrated downward until signs of relapse occur. Larger doses of the IL-17 binding molecule may be administered until the optimal therapeutic effect is obtained for the subject, and at that point the dosage is not generally increased further.

An IL-17 binding molecule is conveniently administered parenterally, intravenously, e.g. into the antecubital or other peripheral vein, intramuscularly, or subcutaneously. The duration of intravenous (i.v.) therapy using a pharmaceutical composition of the present disclosure will vary, depending on the severity of the disease being treated and the condition and personal response of each individual patient. Also contemplated is subcutaneous (s.c.) therapy using a pharmaceutical composition of the present disclosure. The attending physician will decide on the appropriate duration of i.v. or s.c. therapy and the timing of administration of the therapy, using the pharmaceutical composition of the present disclosure.

Satisfactory results (treatment, prophylaxis, delay of onset of symptoms) are generally indicated to be obtained at dosages from about 0.05 mg to about 20 mg per kilogram body weight, more usually from about 0.1 mg to about 20 mg per kilogram body weight. The frequency of dosing may be in the range from about once per week up to about once every three months, e.g., in the range from about once every 2 weeks up to about once every 12 weeks, e.g., once every four to eight weeks. The dosing frequency will depend on, inter alia, the phase of the treatment regimen.

In some embodiments, an IL-17 binding molecule (e.g., IL-17 antibody, such as secukinumab) is administered during an induction regimen and/or maintenance regimen. In some embodiments, the induction regimen comprises a loading regimen. In further embodiments, the loading regimen comprises administration of 1, 2, 3, 4, 5, 6, or more weekly doses of secukinumab, preferably five weekly doses of secukinumab (e.g., delivered during weeks 0, 1, 2, 3, 4). In some embodiments, the loading regimen comprises administration of daily doses of secukinumab, e.g., daily doses of secukinumab delivered for one week. In some embodiments, the loading dosage that may be administered in these weekly or daily amounts may be about 25 mg-about 300 mg delivered s.c., e.g., about 150 mg-about 300 mg s.c, e.g., about 150 mg or about 300 mg delivered s.c. In other embodiments, the induction regimen, in addition to including a loading regimen, further comprises delivery of secukinumab as monthly doses, e.g., 1, 2, 3, 4, 5 or more monthly doses of secukinumab, preferably one monthly dose of secukinumab delivered at week eight.

In some embodiments, the maintenance regimen comprises administration of an IL-17 binding molecule (e.g., IL-17 antibody, such as secukinumab) (e.g., about 75 mg-about 300 mg delivered s.c., e.g., about 150 mg-about 300 mg s.c, e.g., about 150 mg or about 300 mg) in a continuous fashion delivered bimonthly, monthly, every two months or every three months. In a preferred embodiment, a maintenance dose is delivered monthly. In some embodiments, if the dose during the maintenance regimen is delivered monthly, the first monthly dose is delivered on week 12, and then monthly (e.g., about every 4 weeks or about every 28 days) thereafter. In some embodiments, if the dose during the maintenance regimen is delivered every two months, the first dose is delivered on week 16, and then every two months (e.g., about every 8 weeks or about every 56 days) thereafter. In some embodiments, if the dose during the maintenance regimen is delivered every three months, the first dose is delivered on week 20, and then every three months (e.g., about every 12 weeks or about every 84 days) thereafter.

In some embodiments, the maintenance regimen comprises intermittent administration of an IL-17 binding molecule (e.g., IL-17 antibody, such as secukinumab) (e.g., about 75 mg-about 300 mg delivered s.c., e.g., about 150 mg-about 300 mg s.c, e.g., about 150 mg or about 300 mg) as one or two doses (e.g., a single dose) following SoR. Following these one or two doses, the patient is monitored for an additional SoR as defined herein. Upon observation of an additional SoR (which can be determined using any acceptable dermatological scoring system, preferably the PASI scoring system), the patient may be administered an additional one or two doses (e.g., a single dose) of secukinumab. This treatment at SoR may be continued for the life of the patient, as long as the patient's psoriatic symptoms are efficiently retreated with intermittent therapy delivered at SoR (e.g., the relapse PASI score can be improved to an acceptable PASI score). In some embodiments, SoR is defined as the loss of 20% of the maximum PASI response achieved at any time before the visit at which the assessment of start of relapse is made and loss of PASI 75.

In some embodiments, the maintenance regimen following SoR comprises administration of at least one dose (e.g., one, two, three, four, or more) of secukinumab (e.g., about 75 mg-about 300 mg delivered s.c., e.g., about 150 mg-about 300 mg s.c, e.g., about 150 mg or about 300 mg) until a given endpoint is met, e.g., achievement of PASI75. In a preferred embodiment, once a patient experiences SoR, the patient is s.c. administered at least one dose (e.g., one, two, three, four, or more) of about 75 mg-about 300 mg (e.g., about 75 mg, about 150 mg, about 300 mg, preferably about 150 mg or about 300 mg) of the IL-17 binding molecule (e.g., secukinumab) monthly until PASI75 is achieved.

Should intermittent therapy, e.g., treatment at SoR, no longer improve a patient's psoriatic symptoms (e.g., the relapse PASI score can no longer be improved to an acceptable PASI score, e.g., PASI75), then the patient may enter into continuous therapy. In a maintenance regimen employing continuous therapy, the patient may be administered secukinumab (e.g., about 150 mg-about 300 mg s.c., e.g., about 150 mg or about 300 mg s.c.) weekly, bimonthly, monthly, every two months or every three months. Alternatively, a maintenance regimen may begin as an intermittent therapy (e.g., treatment SoR), but may be switched to a continuous therapy. For example, if a patient shows regular intervals between SoR, a physician might decide to switch the patient to continuous treatment, but using a particular interval identified for that individual patient (rather than a pre-defined interval). This would result in a "semi-individualized" approach, rather than a completely individualized approach during which each dose is triggered by SoR. For example, if a patient persistently presents with SoR scores every 5-6 weeks, then a physician may switch the patient from intermittent therapy (treatment at SoR) to continuous administration of secukinumab every five or six weeks.

In some embodiments, the dosage of secukinumab used in the disclosed induction and/or maintenance regimens is based on the patient's weight. In one embodiment, the patient is administered about 150 mg s.c. if the patient weighs less than or equal to about 90 kg. In one embodiment, the patient is administered about 150 mg s.c. if the patient weighs less than or equal to about 100 kg. In another embodiment, the patient is administered about 300 mg s.c. if the patient weighs more than about 90 kg. In another embodiment, the patient is administered about 300 mg s.c. if the patient weighs more than about 100 kg. Other types of weight-based dosing for use in the disclosed methods include, e.g., 75 mg for less than 70 kg, 150 mg for less than 90 kg, 300 mg for greater than or equal to 90 kg. Furthermore, an artisan could also administer the IL-17 binding molecule based on a combination of bodyweight-based dosing and response-based dosing, e.g., non-responders to 150 mg who are, e.g., less than 70 kg, are escalated to 300 mg.

It will be understood that dose escalation may be required (e.g., during the induction and/or maintenance phase) for certain patients, e.g., patients that display partial response non-response to treatment with the IL-17 binding molecules (e.g., secukinumab). Thus, dosages of secukinumab may be greater than about 75 mg to about 300 mg s.c., e.g., about 80 mg, about 100 mg, about 125 mg, about 175 mg, about 200 mg, about 250 mg, about 350 mg, about 400 mg, etc. It will also be understood that dose reduction may also be required (e.g., during the induction and/or maintenance phase) for certain patients, e.g., patients that display adverse events or an adverse response to treatment with the IL-17 binding molecules (e.g., secukinumab). Thus, dosages of secukinumab may be less than about 75 mg to about 300 mg s.c., e.g., about 25 mg, about 50 mg, about 80 mg, about 100 mg, about 125 mg, about 175 mg, about 200 mg, 250 mg, etc.

Disclosed herein are methods of treating psoriasis, comprising: a) administering an IL-17 binding molecule to a patient in need thereof during an induction regimen, wherein the induction regimen comprises a loading regimen, wherein the loading regimen comprises administering the patient five doses of about 75 mg-about 300 mg (e.g., about 150 mg-about 300 mg) of the IL-17 binding molecule, each of the five doses being delivered weekly, beginning on week zero; and b) thereafter administering the IL-17 binding molecule to the patient during a maintenance regimen.

In some embodiments, the five doses of the IL-17 binding molecule are about 75 mg-about 300 mg each. In some embodiments, the five doses are each about 150 mg or about 300 mg each. In some embodiments, the five doses of about 150 mg are administered to the patient if the patient weighs less than 90 kg and wherein the five doses of about 300 mg are administered to the patient if the patient weighs more than or equal to 90 kg. In some embodiments, the induction regimen further comprises administering the patient about 75 mg-about 300 mg of the IL-17 binding molecule during week eight.

In some embodiments, the maintenance regimen comprises treating the patient with about 75 mg-about 300 mg of the IL-17 binding molecule monthly, every two months or every three months. In some embodiments, the maintenance regimen comprises treating the patient with at least one dose of about 75 mg-about 300 mg of the IL-17 binding molecule at start of relapse. In some embodiments, the maintenance regimen further comprises treating the patient with at least one dose of about 75 mg-about 300 mg of the IL-17 binding molecule at each additional start of relapse. In some embodiments, the maintenance regimen comprises treating the patient with a dose of about 75 mg-about 300 mg of the IL-17 binding molecule at start of relapse and thereafter treating the patient monthly with a dose of about 75 mg-about 300 mg of the IL-17 binding molecule until PASI75 is achieved. In some embodiments, the maintenance regimen comprises treating the patient with a booster dose of the IL-17 binding molecule that is higher than the dose of the IL-17 binding molecule employed during the induction regimen if the patient is a partial responder or a non-responder to treatment with the IL-17 binding molecule during the induction regimen.

Disclosed herein are IL-17 binding molecules for use in treating psoriasis, characterized in that at least one dose of the IL-17 binding molecule is administered to a patient at start of relapse from a prior treatment with the IL-17 binding molecule. Also disclosed herein are methods of treating psoriasis, comprising: a) identifying a patient at start of relapse from a prior psoriasis treatment employing an IL-17 binding molecule; and b) administering to the patient at least one dose of the IL-17 binding molecule.

In some embodiments, the at least one dose of the IL-17 binding molecule is about 75 mg-about 300 mg each. In some embodiments, the at least one dose of the IL-17 binding molecule is about 150 mg or about 300 mg each. In some embodiments, steps a) and b) are repeated.

In some embodiments, the prior treatment with the IL-17 binding molecule comprises an induction regimen. In some embodiments, the induction regimen comprises a loading regimen. In some embodiments, the loading regimen comprises administering the patient five doses of about 75 mg-about 300 mg of the IL-17 binding molecule, each of the five doses being delivered weekly, beginning on week zero. In some embodiments, the five doses are each about 150 mg or about 300 mg. In some embodiments, the five doses of about 150 mg are administered to the patient if the patient weighs less than 90 kg and wherein the five doses of about 300 mg are administered to the patient if the patient weighs more than or equal to 90 kg. In some embodiments, the induction regimen further comprises administering the patient about 75 mg-about 300 mg the IL-17 binding molecule during week eight.

In some embodiments, the prior treatment with the IL-17 binding molecule comprises administering to the patient at least one dose of the IL-17 binding molecule at start of relapse.

Disclosed herein are methods of treating psoriasis, comprising: a) administering a patient in need thereof five doses of about 75 mg-about 300 mg (e.g., about 150 mg-about 300 mg) of an IL-17 binding molecule, each of the five doses being delivered weekly, beginning on week zero; b) administering the patient about 75 mg-about 300 mg (e.g., about 150 mg-about 300 mg) the IL-17 binding molecule during week eight; c) administering the patient at least one dose of about 75 mg-about 300 mg (e.g., about 150 mg-about 300 mg) the IL-17 binding molecule at start of relapse; and d) repeating step c) at each additional start of relapse.

Disclosed herein are therapeutic regimens for treating psoriasis, comprising:

a) administering an IL-17 binding molecule to a patient in need thereof during an induction regimen comprising; i. administering about 75 mg-about 300 mg (e.g., about 150 mg-about 300 mg) of the IL-17 binding molecule to the patient weekly for five weeks, wherein the first dose of the IL-17 binding molecule is administered during week zero; and ii. thereafter administering about 75 mg-about 300 mg (e.g., about 150 mg-about 300 mg) of the IL-17 binding molecule to the patient during week eight; and b) administering the IL-17 binding molecule to the patient during a maintenance regimen comprising; i. administering about 75 mg-about 300 mg (e.g., about 150 mg-about 300 mg) of the IL-17 binding molecule to the patient each month, every two months or every three months; or ii. administering at least one dose of about 75 mg-about 300 mg (e.g., about 150 mg-about 300 mg) of the IL-17 binding molecule to the patient at start of relapse.

Disclosed herein are IL-17 binding molecules for use in treating psoriasis, characterized in that the IL-17 binding molecule: a) is to be administered during an induction regimen, wherein the induction regimen comprises a loading regimen, wherein the loading regimen comprises administering five doses of about 75 mg-about 300 mg (e.g., about 150 mg-about 300 mg) of the IL-17 binding molecule, each of the five doses being delivered weekly, beginning on week zero; and b) thereafter, is to be administered during a maintenance regimen.

In some embodiments, the loading regimen comprises administering five doses of about 150 mg or about 300 mg of the IL-17 binding molecule. In some embodiments, the five doses of about 150 mg are administered to the patient if the patient weighs less than 90 kg and wherein the five doses of about 300 mg are administered to the patient if the patient weighs more than or equal to 90 kg. In some embodiments, the induction regimen further comprises administering the patient about 75 mg-about 300 mg of the IL-17 binding molecule during week eight.

In some embodiments, the maintenance regimen comprises treating the patient with about 75 mg-about 300 mg of the IL-17 binding molecule monthly, every two months or every three months. In some embodiments, the maintenance regimen comprises treating the patient with at least one dose of about 75 mg-about 300 mg of the IL-17 binding molecule at start of relapse. In some embodiments, the maintenance regimen further comprises treating the patient with at least one dose of about 75 mg-about 300 mg of a the IL-17 binding molecule at each additional start of relapse.

Disclosed herein are IL-17 binding molecules for use in treating psoriasis, characterized in that the IL-17 binding molecule is: a) to be administered to a patient in need thereof as five doses of about 75 mg-about 300 mg (e.g., about 150 mg-about 300 mg), each of the five doses being delivered weekly, beginning on week zero; b) thereafter to be administered to the patient during week eight in an amount of about 75 mg-about 300 mg (e.g., about 150 mg-about 300 mg); c) thereafter to be administered to the patient as at least one dose of about 75 mg-about 300 mg (e.g., about 150 mg-about 300 mg) at start of relapse; and d) thereafter to be administered to the patient at start of each additional relapse as at least one dose of about 75 mg-about 300 mg (e.g., about 150 mg-about 300 mg).

Disclosed herein are IL-17 binding molecules for use in treating psoriasis, characterized in that the IL-17 binding molecule is:

a) to be administered to a patient in need thereof during an induction regimen comprising; i. the IL-17 binding molecule is to be administered to the patient at a dose of about 75 mg-about 300 mg (e.g., about 150 mg-about 300 mg) weekly for five weeks, wherein the first dose of the IL-17 binding molecule is to be administered during week zero; and ii. thereafter the IL-17 binding molecule is to be administered to the patient at a dose of about 75 mg-about 300 mg (e.g., about 150 mg-about 300 mg) during week eight; and b) to be administered to the patient during a maintenance regimen comprising; i. the IL-17 binding molecule is to be administered to the patient at a dose of about 75 mg-about 300 mg (e.g., about 150 mg-about 300 mg) each month, every two months or every three months; or ii. the IL-17 binding molecule is to be administered to the patient as at least one dose of about 75 mg-about 300 mg (e.g., about 150 mg-about 300 mg) of the IL-17 binding molecule at start of relapse.

Disclosed herein are uses of IL-17 binding molecules for the manufacture of a medicament for treating psoriasis, characterized in that the IL-17 binding molecule is to be administered to a patient at start of relapse from a prior treatment with the IL-17 binding molecule.

Disclosed herein are IL-17 binding molecules for use in treating psoriasis in a patient, wherein said patient is to be identified at start of relapse from a prior treatment with the IL-17 binding molecule and wherein said patient is to be administered at least one dose of the IL-17 binding molecule.

Disclosed herein are pharmaceutical compositions for treating psoriasis, comprising as an active ingredient and the IL-17 binding molecule, wherein the IL-17 binding molecule is to be administered to a patient at start of relapse from a prior treatment with the IL-17 binding molecule.

Disclosed herein are methods of treating psoriasis, comprising: a) administering a patient in need thereof five weekly doses of about 75 mg-about 300 mg (e.g., about 150 mg-about 300 mg) of an IL-17 binding molecule; and b) thereafter administering: i) about 75 mg-about 300 mg (e.g., about 150 mg-about 300 mg) of the IL-17 binding molecule to the patient monthly or ii) one dose of about 75 mg-about 300 mg (e.g., about 150 mg-about 300 mg) of the IL-17 binding molecule to the patient about one month following step a) and thereafter administering at least one dose of about 75 mg-about 300 mg (e.g., about 150 mg-about 300 mg) of the IL-17 binding molecule to the patient at start of relapse.

Disclosed herein are therapeutic regimens for treating psoriasis, comprising: a) administering a patient in need thereof five weekly doses of about 75 mg-about 300 mg (e.g., about 150 mg-about 300 mg) of an IL-17 binding molecule; and b) thereafter administering: i) about 75 mg-about 300 mg (e.g., about 150 mg-about 300 mg) of the IL-17 binding molecule to the patient monthly or ii) one dose of about 75 mg-about 300 mg (e.g., about 150 mg-about 300 mg) of the IL-17 binding molecule to the patient about one month following step a) and thereafter administering at least one dose of about 75 mg-about 300 mg (e.g., about 150 mg-about 300 mg) of the IL-17 binding molecule to the patient at start of relapse.

Disclosed herein are methods of treating psoriasis, comprising: a) administering an IL-17 binding molecule to a patient in need thereof during an induction regimen, wherein the induction regimen comprises a loading regimen that provides a mean maximum plasma concentration ($C_{max}$) of the IL-17 binding molecule of about 52 μg/ml-about 104 μg/ml; and b) thereafter administering the IL-17 binding molecule to the patient during a maintenance regimen that provides an average steady-state trough level of the IL-17 binding molecule between about 5 μg/ml-about 70 μg/ml.

Disclosed herein are IL-17 binding molecules for use in treating psoriasis, characterized in that the IL-17 binding molecule: a) is to be administered to the patient during an induction regimen, wherein the induction regimen comprises a loading regimen that provides a mean maximum plasma concentration ($C_{max}$) of the IL-17 binding molecule of about 52 μg/ml-about 104 μg/ml; and b) thereafter, is to be administered to the patient during a maintenance regimen that provides an average steady-state trough level of the IL-17 binding molecule between about 5 μg/ml-about 70 μg/ml.

In some embodiments, the loading regimen provides a $C_{max}$ of the IL-17 binding molecule of about 52 μg/ml at about day 32. In some embodiments, the maintenance regimen provides an average steady-state trough level of the IL-17 binding molecule of about 5 μg/ml-about 33 μg/ml. In some embodiments, the maintenance provides an average steady-state trough level of the IL-17 binding molecule of about 16 μg/ml. In some embodiments, the loading regimen provides a $C_{max}$ of the IL-17 binding molecule of about 104 μg/ml at about day 32. In some embodiments, the maintenance regimen provides an average steady-state trough level of the IL-17 binding molecule of about 11 μg/ml-about 70 μg/ml. In some embodiments, the maintenance regimen provides an average steady-state trough level of the IL-17 binding molecule of about 33 μg/ml. In some embodiments, the induction regimen is twelve weeks. In some embodiments, the maintenance regimen employs monthly dosing of the IL-17 binding molecule.

Disclosed herein are methods of treating psoriasis, comprising: a) administering an IL-17 binding molecule to a patient in need thereof during an induction regimen, wherein the induction regimen comprises a loading regimen that provides a mean trough level one month after the fourth dose of about 29.2 µg/ml; and b) thereafter administering the IL-17 binding molecule to the patient during a maintenance regimen that provides an average steady-state trough level of the IL-17 binding molecule of about 15 µg/ml.

Disclosed herein are IL-17 binding molecules for use in treating psoriasis, characterized in that the IL-17 binding molecule: a) is to be administered to the patient during an induction regimen, wherein the induction regimen comprises a loading regimen that provides a mean trough level one month after the fourth dose of about 29.2 µg/ml; and b) thereafter, is to be administered to the patient during a maintenance regimen that provides an average steady-state trough level of the IL-17 binding molecule of about 15 µg/ml.

Combination Therapies for the Treatment of Psoriasis

In practicing the methods of treatment, regimens, or uses of the present disclosure, a therapeutically effective amount of an IL-17 antagonist, e.g., an IL-17 binding molecule (e.g., an IL-17 antibody, such as secukinumab) or and IL-17 receptor binding molecule, is administered to a subject, e.g., a mammal (e.g., a human). An IL-17 antagonist, e.g., an IL-17 binding molecule (e.g., an IL-17 antibody, such as secukinumab) or and IL-17 receptor binding molecule may be administered in accordance with the method of the disclosure either alone or in combination with other therapies, such as, e.g., in combination with additional agents and therapies for psoriasis. When coadministered with one or more additional agents, an IL-17 antagonist, e.g., an IL-17 binding molecule (e.g., an IL-17 antibody, such as secukinumab) or and IL-17 receptor binding molecule may be administered either simultaneously with the other agent, or sequentially. If administered sequentially, the attending physician will decide on the appropriate sequence of administering the IL-17 antagonist, e.g., an IL-17 binding molecule (e.g., an IL-17 antibody, such as secukinumab) or and IL-17 receptor binding molecule in combination with other agents.

Various therapies may be beneficially combined with the disclosed IL-17 antagonists, e.g., IL-17 binding molecules (e.g., an IL-17 antibody, such as secukinumab) and IL-17 receptor binding molecules, during treatment of psoriasis. Such therapies include topicals (over the counter, non-steroidal compounds and steroidal compound), phototherapy and systemic treatment (e.g., with biologic or chemical entities). Non-limiting examples of topical agents for use with the disclosed IL-17 antagonists, e.g., IL-17 binding molecules (e.g., an IL-17 antibody, such as secukinumab) and IL-17 receptor binding molecules, include salicylic acid, coal tar, Dovonex® (calcipotriene), Taclonex® (calcipotriene and betamethasone dipropionate), Tazorec® (tazarotene), pimecrolimus, tacrolimus, Vectical® (calcitriol), Zithranol-RR® (anthralin) and topical steroids (e.g., corticosteroids). Examples of phototherapy for use with the disclosed IL-17 antagonists, e.g., IL-17 binding molecules (e.g., an IL-17 antibody, such as secukinumab) and IL-17 receptor binding molecules, includes treatment with psoralen+UVA or treatment with UVB (with or without tar). Examples of agents used in systemic treatment for use with the disclosed IL-17 antagonists, e.g., IL-17 binding molecules (e.g., an IL-17 antibody, such as secukinumab) and IL-17 receptor binding molecules, include retionoids such as Acitretin (Soriatane®), cyclosporine, methotrexate, Hydrea® (hydroxyurea), isotretinoin, mycophenolate mofetil, mycophenolic acid, sulfasalazine, 6-thioguanine, fumarates (e.g, dimethylfumarate and fumaric acid esters), azathioprine, corticosteroids, leflunomide, tacrolimus, T-cell blockers (such as Amevive® (alefacept) and Raptiva® (efalizumab), tumor necrosis factor-alpha (TNF-alpha) blockers (such as Enbrel® (etanercept), Humira® (adalimumab), Remicade® (infliximab) and Simponi® (golimumab)) and interleukin 12/23 blockers (such as Stelara® (ustekinumab), tasocitinib, Efalizumab, and briakinumab.

Additional agents for use in combination with the disclosed IL-17 antagonists, e.g., IL-17 binding molecules (e.g., an IL-17 antibody, such as secukinumab) and IL-17 receptor binding molecules, during treatment of psoriasis include apremilast, mometasome, voclosporin, Ketokonazol, Neuroskin Forte, recombinant human interleukin-10, voclosporin, VX-765, MED-1545, fluphenazine decanoate, acetomuinophn, bimosiamose cream, doxycycline, vancomycin, AbGn168, Vitamin D3, RO5310074, fludarabine Calcipotriol and hydrocortisone (LEO 80190), LE80185 (Taclonex® Scalp topical suspension/Xamiol® gel), Focetria (Monovalent MF59-Adjuvanted vaccine, tgAAC94 gene therapy vector, Apremilast, Capsaicin, Psirelax, ABT-874 (anti IL-12), IDEC-114, MEDI-522, INCB018424 phosphate cream, LE29102, BMS 587101, CD 2027, CRx-191, 8-methoxypsoralen or 5-methoxypsoralen, Bicillin L-A, LY2525623, INCB018424, LY2439821, CEP-701, CC-10004, certolizumab (CZP), GW786034 (pazopanib), doxycycline Curcuminoids C3 Complex, NYC 0462, RG3421, hOKT3gamma1 (Ala-Ala), BT061, teplizumab, Chondroitin sulphate, CNTO 1275, monoclonal antibody to IL-12p40 and IL-23 p40 subunits, BMS-582949, MK0873, MEDI-507, M518101, ABT-874, AMG 827, AN2728, AMG 714, AMG 139, PTH (1-34), U0267 Foam, CNTO 1275, QRX-101, CNTO 1959, LEO 22811, Imiquimod, CTLA4Ig, Alga Dunaliella Bardawil, AS101 Cream, pioglitazone, pimecrolimus, ranibizumab, Zidovudine CDP870 (Certolizumab pegol), Onercept (r-hTBP-1), ACT-128800, 4,4-dimethyl-benziso-2H-selenazine, CRx-191, CRx-197, doxercalciferol, LEO 19123 Cream (calcipotriol plus LEO 80122), LAS 41004, WBI-1001, tacrolimus, RAD001, rapamycin, rosiglitazone, pioglitazone, ABT-874, Aminopterin, AN2728, CD2027, ACT-128800, mometasone furoate, CT 327, clobetasol+LCD, BTT1023, E6201, topical vitamin B12, INCB018424 Phosphate Cream, Xamiol gel, IP10.C8, BFH772, LEO 22811, Fluphenazine, MM-093, Clobex, SCH 527123, CF101, SRT2104, BIRT2584, CC10004, Tetrathiomolybdate, CP-690,550, U0267, ASP015K, VB-201, Acitretin (also called U0279), RWJ-445380, Psoralait, Clobetasol propionate, botulinum toxin type A, alefacept, erlotinib, BCT194, Ultravate Ointment, Roflumilast, CNTO 1275, halobetasol, CTA018 cream, ILV-094, COL-121, MEDI-507, AEB071. Additional agents for use in combination with secukinumab during treatment of psoriasis include IL-6 antagonists, CD20 antagonistis, CTLA4 antagonists, IL-17 antagonists, IL-8 antagonists, IL-21 antagonistis, IL-22 antagonist, VGEF antagonists, CXCL antagonists, MMP antagonists, defensin antagonists, IL-1beta antagonists, and IL-23 antagonists (e.g., receptor decoys, antagonistic antibodies, etc.). A skilled artisan will be able to discern the appropriate dosages of the above agents for co-delivery with the disclosed IL-17 antagonists, e.g., IL-17 binding molecules (e.g., an IL-17 antibody, such as secukinumab) and IL-17 receptor binding molecules.

Kits for the Treatment of Psoriasis

Provided herein are kits useful for providing IL-17 antagonists, e.g., IL-17 binding molecules (e.g., an IL-17 antibody, such as secukinumab) and IL-17 receptor binding molecules, for the treatment of psoriasis. Such kits may comprise an IL-17 antagonist (e.g., in liquid or lyophilized form) or a pharmaceutical composition comprising the IL-17 antagonist. Additionally, such kits may comprise means for administering the IL-17 binding molecule (e.g., a syringe or a prefilled pen) and instructions for use. These kits may contain additional therapeutic agents (described supra) for treating psoriasis, e.g., for delivery in combination with the enclosed IL-17 antagonists, e.g., secukinumab.

Accordingly, disclosed herein are kits comprising: a) a pharmaceutical composition comprising a therapeutically effective amount of an IL-17 binding molecule; b) means for administering the IL-17 antagonist (e.g., IL-17 binding molecule or IL-17 receptor binding molecule) to a patient having psoriasis; and c) instructions providing: i) administering the IL-17 antagonist (e.g., IL-17 binding molecule or IL-17 receptor binding molecule) to the patient during an induction regimen comprising: a. administering about 75 mg-about 300 mg of the IL-17 antagonist (e.g., IL-17 binding molecule or IL-17 receptor binding molecule) to the patient weekly for five weeks, wherein the first dose of the IL-17 binding molecule is administered during week zero; and b. thereafter administering about 75 mg-about 300 mg of the IL-17 antagonist (e.g., IL-17 binding molecule or IL-17 receptor binding molecule) to the patient during week eight; and ii) administering the IL-17 antagonist (e.g., IL-17 binding molecule or IL-17 receptor binding molecule) to the patient during a maintenance regimen comprising: a. administering about 75 mg-about 300 mg of the IL-17 antagonist (e.g., IL-17 binding molecule or IL-17 receptor binding molecule) to the patient each month, every two months or every three months; or b. administering at least one dose of about 75 mg-about 300 mg of the IL-17 antagonist (e.g., IL-17 binding molecule or IL-17 receptor binding molecule) to the patient at start of relapse.

General

In some embodiments of the disclosed methods, regimens, kits, uses, or pharmaceutical compositions, the IL-17 antagonist (e.g., IL-17 binding molecule or IL-17 receptor binding molecule) is selected from the group consisting of:
  a) secukinumab;
  b) an IL-17 antibody that binds to an epitope of IL-17 comprising Leu74, Tyr85, His86, Met87, Asn88, Val124, Thr125, Pro126, Ile127, Val128, His129;
  c) an IL-17 antibody that binds to an epitope of IL-17 comprising Tyr43, Tyr44, Arg46, Ala79, Asp80;
  d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain;
  e) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 µM, and wherein the IL-17 binding molecule has an in vivo half-life of about 4 weeks; and f) an IL-17 antibody that comprises an antibody selected from the group consisting of:
    i) an immunoglobulin heavy chain variable domain ($V_H$) comprising the amino acid sequence set forth as SEQ ID NO:8;
    ii) an immunoglobulin light chain variable domain ($V_L$) comprising the amino acid sequence set forth as SEQ ID NO:10;
    iii) an immunoglobulin $V_H$ domain comprising the amino acid sequence set forth as SEQ ID NO:8 and an immunoglobulin $V_L$ domain comprising the amino acid sequence set forth as SEQ ID NO:10;
    iv) an immunoglobulin $V_H$ domain comprising the hypervariable regions set forth as SEQ ID NO:1, SEQ ID NO:2, and SEQ ID NO:3;
    v) an immunoglobulin $V_L$ domain comprising the hypervariable regions set forth as SEQ ID NO:4, SEQ ID NO:5 and SEQ ID NO:6;
    vi) an immunoglobulin $V_H$ domain comprising the hypervariable regions set forth as SEQ ID NO:11, SEQ ID NO:12 and SEQ ID NO:13;
    vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; and
    viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

In the above mentioned methods, therapeutic regimens, uses, pharmaceutical compositions, combinations, combination therapies, and kits, a preferred embodiment employs a human IL-17 antibody, e.g., a human IL-17 antibody (e.g., a human monoclonal antibody), most preferably secukinumab.

In some embodiments of the disclosed methods, regimens, kits, IL-17 binding molecules, uses and pharmaceutical compositions, the IL-17 antagonist (e.g., IL-17 binding molecule or IL-17 receptor binding molecule) is self-administered by the patient.

In some of the above mentioned methods, therapeutic regimens, uses, pharmaceutical compositions, combinations, combination therapies, and kits, the patient to be treated with secukinumab is a naïve patient (i.e., has not been previously treated for psoriasis). In other embodiments, the patient to be treated with secukinumab has been previously treated with a systemic agent for psoriasis, e.g., with an agent selected from the group consisting of methotrexate, cyclosporine, fumaric acid esters, acitretin, alefacept, adalimumab, efalizumab, etanercept, infliximab, golimumab or ustekinumab. In preferred embodiments, the systemic agent is methotrexate.

In some embodiments, the disclosed treatment regimens are used in patients having moderate to severe chronic plaque psoriasis who are candidates for systemic therapy or phototherapy. In some embodiments, the disclosed treatment regimens are used in patients having moderate to severe chronic plaque psoriasis who are candidates for systemic therapy or phototherapy, and when other systemic therapies are medically less appropriate. In some embodiments, the disclosed treatment regimens are used in patients having moderate to severe chronic plaque psoriasis who are candidates for systemic therapy, and when other systemic therapies are medically less appropriate. In some embodiments, the patient may be an anti-TNF alpha psoriasis treatment non-responder, partial responder (e.g., an inadequate responder), relapser or rebounder.

In some of the above mentioned methods, therapeutic regimens, uses, pharmaceutical compositions, combinations, combination therapies, and kits, start of relapse is defined as: a) the loss of at least 20% (⅕) of the maximum PASI response achieved at any time before the visit at which the assessment of start or relapse is made; and b) loss of PASI75.

In some of the above mentioned methods, therapeutic regimens, uses, pharmaceutical compositions, combinations, combination therapies, and kits, the patient suffers from psoriasis of the palms and/or soles, face psoriasis, scalp psoriasis, genital psoriasis, inverse psoriasis, or nail psoriasis. In further embodiments, the psoriasis is chronic plaque-type psoriasis.

EXAMPLES

Example 1

Proof of Concept Using Secukinumab to Treat Psoriasis

In a completed proof of concept (PoC) study (CAIN457A2102), the effects of secukinumab administered at 3 mg/kg as a single intravenous infusion were compared with that of placebo in thirty-six patients with active chronic plaque type psoriasis. The study demonstrated efficacy at the 4-week endpoint and continuous efficacy at 12 weeks based on Psoriasis Area an Severity Index (PAST) and Investigator Global Assessment (IGA) endpoints.

In a follow up (CAIN457A2212) study, three secukinumab i.v. regimens were tested in patients with active chronic plaque-type psoriasis: 1×3 mg/kg (administered on day 1), 1×10 mg/kg (administered on day 1), and 3×10 mg/kg (administered on days 1, 15, and 29). The 3 mg/kg i.v. arm confirmed the efficacy seen in PoC (40% of patients achieving PASI75 after 12 wks). The 10 mg/kg i.v. arms displayed much improved efficacy compared to 3 mg/kg i.v. treatment arm, with 73% (10 mg/kg)-87% (3×10 mg/kg) patients achieve PASI75 at week 12. Moreover, the onset of action of secukinumab was very fast (about 2 weeks). Notably, as shown in FIG. 1, no rebound is observed in secukinumab-treated patients within 8 weeks after dosing. This is in contrast to various other psoriasis treatments, which have been shown to induce rebound in patients, e.g., some TNF alpha antagonists and cyclosporin. This lack of rebound suggests the feasibility of intermittent psoriasis treatment, e.g., treatment at SoR, with secukinumab.

Example 2

Study CAIN457A2211

Example 2.1

Protocol

Primary Objectives

To evaluate the efficacy of three induction regimens of secukinumab administered subcutaneously in patients with moderate to severe chronic plaque-type psoriasis with respect to PASI 75 achievement after 12 weeks of treatment, compared to placebo.

Study Design

This multicenter study uses a parallel-group, randomized, double-blind design. A graphical illustration of the study is shown in FIG. 2. The study consists of 4 periods: the screening period, the induction period, the maintenance period and the follow-up period. The screening period of 4 weeks will be used to assess eligibility and to taper patients off disallowed medications. At the baseline visit, eligible patients will be randomized to one of the induction treatment arms. Randomization will be stratified according to body weight (≥90 kg or <90 kg). Patients will be randomized as follows:

Induction Period

Patients will be assigned to one of the following four induction treatment arms in a ratio of 1:2:2:1 respectively:
- Induction with single injection—"Single": secukinumab 150 mg s.c. administered at week 1
- Induction with monthly injections—"Monthly": secukinumab 150 mg s.c. administered at weeks 1, 5, 9
- Early loading induction—"Early": secukinumab 150 mg s.c. administered at weeks 1, 2, 3, 5
- Placebo—"Placebo": Placebo administered at weeks 1, 2, 3, 5, 9

In each of the active treatment arms, placebo injections will be administered to maintain the blind in the study.

Maintenance Period

At week 13, patients will be classified as responders (achieving at least PASI 75), partial responders (achieving PASI 50, but not PASI 75) or non-responders (not achieving PASI 50). Responders at week 13 will be further randomized to one of the following maintenance treatment arms in a ratio of 1:1:
- Fixed-time interval regimen—"FI": secukinumab 150 mg s.c. administered at week 13 and at week 25 and placebo at regular scheduled visit at which a start of relapse is observed.
- Treatment at start of relapse regimen—"SR": Placebo administered at week 13 and possibly at week 25 if no start of relapse observed, and secukinumab 150 mg s.c. administered at regular scheduled visit at which a start of relapse is observed.

Responders on placebo regimen will remain on the placebo arm and will receive placebo at week 13 and at week 25 and placebo at regular scheduled visit at which a start of relapse is observed.

Open Label Phase

Non responders and partial responders at week 13 and patients who experience 2 consecutive relapses at scheduled visits from week 13 onwards will be eligible to enter the open label phase—"OL": secukinumab 150 mg s.c. administered every 4 weeks. The last study drug administration for all patients remaining in the study will potentially be at week 33. All randomized patients will enter the treatment-free follow-up period 4 weeks after the last study drug administration to monitor safety and will be monitored for 12 weeks (Visits 13, 14 and 15). The assessment to address the primary objective will be performed at the end of the induction period (week 13).

Psoriasis Area and Severity Index: PASI

A PASI score will be derived at scheduled visits. In the PASI scoring system, the head, trunk, upper limbs and lower limbs are assessed separately for erythema, thickening (plaque elevation, induration), and scaling (desquamation) (see Table 1).

Example 2.2

Results for CAIN457A2211

Interim Analysis Results (12 Weeks):

PASI Response

Data available from the interim analysis performed at week 12 shows a PASI75 of 12% in the "Single" arm, 43% in the "Monthly" arm and 55% in the "Early" arm compared to 5% in the placebo arm (Table 5 and FIG. 3). Both "Monthly" and "Early" arms showed statistical significance compared to placebo (p<0.001). The "Early" arm (4×150 mg secukinumab s.c. within the first five weeks) showed the highest efficacy, which was better than 3 mg/kg IV (PoC), but lower than 10 mg/kg IV (CAIN457A2212).

TABLE 5

PASI achievement after 12 weeks of treatment with secukinumab compared to placebo in both "Monthly" and "Early" arms (p < 0.001) in study CAIN457A2211.

| Treatment Group | PASI 50 | PASI 75 | PASI 90 |
|---|---|---|---|
| secukinumab 150 mg × 1 ("Single"; N = 66) | 28.8% | 12.1% | 4.5% |
| secukinumab 150 mg × 3 ("Monthly"; N = 138) | 60.9% | 42.8% | 18.1% |
| secukinumab 150 mg × 4 ("Early"; N = 133) | 76.5% | 54.5% | 31.8% |
| Placebo (N = 67) | 13.6% | 4.5% | 4.5% |

In study CAIN457A2211, response rates did not meaningfully improve after Week 8 in the "Early" arm (which did not include dosing at Week 8), whereas the response rate clearly improved after Week 8 in the "Monthly" arm (which did include dosing at Week 8) (FIG. 3). Moreover, 8 patients in the "Early" arm who had already achieved a PASI 75 response at Week 8 had lost the PASI 75 by Week 12. This data supports monthly dosing after weekly loading.

A body-weight-response relationship was also shown in study CAIN457A2211; 60.9% of patients with a body weight of <90 kg showed a PASI 75 response after twelve weeks of treatment, whereas only 47.6% achieved this response in the group of patients weighing ≥90 kg (Table 6). The response rate for achievement of an Investigator's Global Assessment (IGA) score or 0 or 1 was also statistically significantly better for the "Monthly" (22.6%) and "Early" (37.9%) arms, when compared to placebo (3.0%; p<0.001). The short term safety profile of secukinumab in this study was comparable to placebo without a dose effect seen and a similar percentage (~60-70%) of adverse events across all dose arms and placebo. This included infectious events which were 21%, 39%, 33% in the "single", "monthly" and "early" cohorts respectively compared to 37% in the placebo cohort. Percentage of serious adverse events (SAEs) were 5%, 2%, 5% in the "single", "monthly" and "early" cohorts respectively compared to 3% in the placebo cohort.

TABLE 6

PASI achievement analyzed by weight after 12 weeks of treatment with secukinumab compared to placebo.

| Treatment Group | <90 kg | ≥90 kg | All |
|---|---|---|---|
| secukinumab 150 mg ×1 ("Single"; N = 66) | 20.6% (7/34) | 3.1% (1/32) | 12.1% |
| secukinumab 150 mg ×3 ("Monthly"; N = 138) | 53.6% (37/69) | 31.9% (22/69) | 42.8% |
| secukinumab 150 mg ×4 ("Early"; N = 133) | 60.9% (42/69) | 47.6% (30/63) | 54.5% |
| Placebo (N = 67) | 5.9% (2/34) | 3.1% (1/32) | 4.5% |

IGA Response

In addition to the PASI response, the primary endpoint analysis was performed on the Investigator's Global Assessment (IGA) achievement. A scale from 0 (clear) to 5 (very severe) was used. A patient was regarded as an IGA responder if an IGA of 0 (clear) or 1 (almost clear) was reached; an inclusion criterion was a baseline IGA of ≥3. After twelve weeks of treatment, an IGA response was achieved by 4.5% of the patients in the "Single" arm, 22.6% of the patients in the "Monthly" arm, and 37.9% in the "Early" arm; only 3.0% of patients in the placebo arm achieved an IGA 0/1 response.

Just as for the PASI response over time, it was shown that the number of IGA responders increased after administration of secukinumab after eight weeks in the "Monthly" arm, but only slightly so in the "Early" arm, in which no secukinumab was given after eight weeks. Furthermore, a body weight-IGA response relationship was also shown for the "Single" and the "Monthly" regimen, but not for the "Early" regimen. In the "Single" arm, the IGA response rate after twelve weeks of treatment was 8.8% in the weight group of <90 kg, but 0.0% in the weight group ≥90 kg. Similarly, in the "Monthly" arm, the response rates were 35.3% and 10.1%. In the "Early" arm, the response rates were very similar between body weight groups, with 39.1% (<90 kg) and 36.5% (≥90 kg).

Interim Analysis Results (28 Weeks):

An interim analysis (IA) was performed 16 weeks after 103 patients had reached a PASI 75 response after twelve weeks of treatment. In this IA, the key secondary objective of comparing the two maintenance regimens ("fixed interval" and "treatment at start of relapse") was assessed by an internal Data Monitoring Committee (DMC).

Baseline Demographics

Compared to the demographics at randomization, the population in this interim analysis consisted of patients with a lower mean body weight (85.1 kg compared to 93.1 kg at randomization). Otherwise, the demographics were comparable. The difference in mean body weight was expected, as only responders entered the double blind maintenance period, and a lower body weight is associated with a higher probability of showing a response after treatment with secukinumab.

PASI Response

In the "fixed interval" treatment arm (51 patients; maintenance treatment with 150 mg of secukinumab s.c. twelve and twenty-four weeks after randomization), 94.1% of patients showed a PASI 75 response (loss of 5.9% response) four weeks into maintenance, 80.4% after eight weeks (loss of 19.6%), and 66.7% twelve weeks into the maintenance period (loss of 33.3%) (FIGS. 4A and 4B). At the Week 25 visit, patients were re-treated with secukinumab, and four weeks later, the percentage of patients with a PASI 75 response slightly increased to 68.6%.

In addition, the fixed interval of four weeks was tested in the open label part of study CAIN457A2211. By definition, the patients who entered this part of the study did not have a PASI 75 response at Week 12. When treated with secukinumab 150 mg open label every four weeks, a significant percentage of patients converted to responder status within eight to twelve weeks (Table 7). To support the rationale of a maintenance interval of four weeks, it should be noted that once a certain level of PASI 75 response rate is achieved ("Single" and "Monthly": Week 20; "Early" and Placebo: Week 24), this percentage is kept at the same level or is slightly improved with this regimen. The safety analysis of the patients in the open label arm of study CAIN457A2211, during which patients were treated with 150 mg of secukinumab every four weeks, reveals no clinically meaningful difference between the open label arm and the other treatment regimens (i.e. fixed interval=treatment every 12 weeks, and re-treatment at start of relapse). This supports the assumption that treatment with secukinumab in maintenance every four weeks promises to show an acceptable safety profile.

TABLE 7

Observed PASI 75 response rates of patients in the open label arm of study CAIN457A2211 receiving 150 mg s.c. every 4 weeks after 12 weeks. Shown in the table are the patients that provided data up to Week 28 in the open label arm for the interim analysis of study CAIN457A2211.

| | Induction treatment up to Week 12 | | | |
|---|---|---|---|---|
| Week | Single (n = 54) | Monthly (n = 78) | Early (n = 57) | Placebo (n = 58) |
| 12 | 0.0% | 0.0% | 0.0% | 0.0% |
| 16 | 14.8% | 19.2% | 19.3% | 15.5% |
| 20 | 35.2% | 26.9% | 19.3% | 39.7% |
| 24 | 40.7% | 28.2% | 31.6% | 55.2% |
| 28 | 42.6% | 29.5% | 29.8% | 60.3% |

In addition, the time until patients suffered from a "start of relapse" (in the CAIN457A2211 study: this was defined as loss of at least 33% of the PASI gain achieved before, where PASI gain was PASI score at randomization minus the lowest PASI ever achieved during the study) was assessed. In the "start of relapse" arm (in which patients were only retreated if they suffered from a "start of relapse"), the first "start of relapse" observations were made thirteen weeks after last study drug administration (6.0% of patients). At sixteen weeks after last study drug administration, only 28.5% of patients experienced a "start of relapse", 41.4% at Week 20, and 55.6% at Week 24 (FIG. 4A, dashed line).

IGA Response

At the beginning of the maintenance period (i.e., twelve weeks after start of study drug), 64.7% of patients in the "fixed interval" arm showed an IGA 0 ("clear") or 1 ("almost clear") response. Four weeks into maintenance, this response was shown by 70.6% of patients, and at eight weeks by 60.8% of the patients. Twelve weeks into the maintenance period, before the patients were retreated for the first time in maintenance, 52.9% of patients had an IGA 0/1 response, and this level was kept four weeks later (51.0%).

Discussion and Analysis

An internal Primary Endpoint Analysis (PEA) was performed after all patients had reached twelve weeks of treatment. The results confirmed that secukinumab is efficacious in the studied indication, meeting the primary endpoint of showing the effect of secukinumab with regard to PASI 75 achievement after twelve weeks of treatment, compared to placebo, in the "Monthly" and "Early" arms.

An Interim Analysis was performed on 103 patients that were responders after twelve weeks of treatment. The key secondary endpoint of comparing the two maintenance regimens ("fixed interval" and "treatment at start of relapse") was assessed by an internal Data Monitoring Committee (DMC). Considering that the treatment goal during maintenance in a "fixed interval" regimen is to keep patients in a status of PASI 75 response, the interim analysis showed that the revised fixed treatment interval should be four weeks. This regimen is used in all phase III studies analyzing fixed dosing.

The interpretation of the maintenance information from study CAIN457A2211 showed that to keep most patients in a PASI 75 response, a fixed treatment interval of four weeks is required (FIG. 4). However, 66.7% of patients kept their PASI 75 response until 12 weeks after last administration of secukinumab, and therefore might not necessarily need re-treatment earlier than at this time point (FIGS. 4A and B). The analysis of the re-treatment at start of relapse approach shows that some patients might be successfully re-treated at longer intervals. FIG. 5 presents the number of subjects with start of relapse over time, and shows that even after about 6 months following last secukinumab administration, a significant percentage of patients maintain a meaningful clinical response. These data imply that an individualized maintenance treatment approach could be useful for the treatment of psoriasis with secukinumab. While not all patients would be eligible for such an approach (i.e., because of their individual response/relapse behavior, because of the need for close monitoring of symptoms, or because of the need to reach the physician on short notice), and might therefore prefer a fixed interval treatment regimen, some patients are expected to benefit from individualized therapy. Patients with a need for less frequent injections than every four weeks would be exposed to less drug compared to a regimen with fixed intervals, which is regarded as a safety benefit.

The analysis of the maintenance period of study CAIN457A2211, while showing the feasibility and potential benefit of the individualized treatment approach, also shows that the rules for "re-treatment at start of relapse" can be refined to achieve greater disease control. Therefore both the starting as well as the stopping rule for re-treatment at start of relapse has been modified for phase III in order to maximize and maintain ideal disease control: start of relapse in phase III is defined as a loss of 20% of the previous PASI gain (as opposed to 33% in phase II) and a loss of PASI 75 response. In addition, once re-treatment at start of relapse has been initiated, it will be continued with a single administration of secukinumab every four weeks until a PASI75 response has been reached again.

Example 3

Study A2220

Example 3.1

Protocol

Primary Objective

To assess the efficacy of three different doses of secukinumab s.c. administered monthly (25 mg, 75 mg and 150 mg) or as a single administration (25 mg) in patients with moderate to severe chronic plaque-type psoriasis with respect to PASI 75 achievement 12 weeks after start of treatment, compared to placebo.

Study Design

This is a multicenter, randomized, double-blind, placebo-controlled, parallel-group trial in 120 patients with moderate to severe chronic plaque-type psoriasis. It is expected that patients will be enrolled at around 25 study sites, whereas a site should recruit no less than 5 patients.

The study consists of 3 periods: screening, treatment and follow up. A graphical representation of the study design is shown in FIG. 6.

The screening period of up to 4 weeks will be used to assess eligibility of the patients and taper patients off disallowed medications. The eligible patients will be randomized into one of five treatment groups, and will receive the study medication monthly three times (weeks 1, 5, and 9). Either placebo or one of three different doses as two different regimens of secukinumab will be administered to the patients of each treatment group with a randomization ratio of 1:1:1:1:1. Randomization will be stratified according to body weight (<90 kg or ≥90 kg). During the treatment period, patients will be visiting the site at weeks 2, 3, 5 and 9. At weeks 5 and 9 they will receive study drug. At all visits, safety, efficacy and PK assessments will be performed. At the end of the 12 week treatment period, patients will enter a follow-up period of maximally 24 weeks. If the patient requires other systemic psoriasis treatment or phototherapy before the end of the follow-up, an end of study visit should be preformed.

The primary endpoint (i.e. achievement of PASI 75 12 weeks after start of treatment) will be analyzed once all patients have completed the treatment phase.

Rationale of Study Design

This study will provide dose ranging information for a treatment period of 12 weeks (with last study drug administration at week 9). The purpose of the present study is to determine the dose(s) of secukinumab that reduce(s) the severity of psoriasis symptoms (compared to placebo).

The study is designed to investigate whether there is a reduction of psoriasis symptoms' severity as measured by Psoriasis Area and Severity Index (PAST) and Investigator's Global Assessment (IGA) achievement in patients with moderate to severe plaque type psoriasis 12 weeks after start of treatment with secukinumab. The PASI score, the assessment of the severity of the psoriasis symptoms and the extent to which the patient's body area is affected by the disease, is considered acceptable by health authorities to assess efficacy in conjunction with Investigator's Global Assessment (IGA).

Treatment Arms

Patients will be assigned to one of the following 5 treatment arms in a ratio of 1:1:1:1:1, with 24 patients per arm Arm "3×150 mg": secukinumab 150 mg s.c. administered at weeks 1, 5, and 9

Arm "3×75 mg": secukinumab 75 mg s.c. administered at weeks 1, 5, and 9

Arm "3×25 mg": secukinumab 25 mg s.c. administered at weeks 1, 5, and 9

Arm "1×25 mg": secukinumab 25 mg s.c. administered at week 1, and placebo s.c. administered at weeks 5 and 9

Arm "Placebo": Placebo s.c. administered at weeks 1, 5, and 9

Psoriasis Area and Severity Index: PASI

A PASI score will be derived at scheduled visits. In the PASI scoring system, the head, trunk, upper limbs and lower limbs are assessed separately for erythema, thickening (plaque elevation, induration), and scaling (desquamation) (see Table 1).

Example 3.2

CAIN457A2220 Study Results (Week 12)

PASI Response

Results of the PASI 75 (primary variable), PASI 50 and PASI 90 responses are shown in FIG. 7 and summarized in Table 8. Highest responses were seen in the 3×150 mg cohort with a PASI 75 of 81.5% (p<0.001 vs. placebo) and a PASI 90 of 51.9% (p<0.001 vs. placebo). The 3×75 mg cohort had a PASI 75 of 57.1% (p=0.002 vs. placebo) after 12 weeks of treatment. Thus, a clear dose-response relationship between cohorts can be seen for all cohorts except the 1×25 mg group, which was not statistically different from placebo (i.e., the 1×25 mg at 3.4% (p=0.308) and the 3×25 mg cohort at 19.2% (p=0.362) showed no statistically significant difference when compared to placebo (Table 9)). Notably, PASI 90 was only achieved by 19% of patients in the 3×75 mg cohort and 7.7% in the 3×25 mg cohort. Response rates were very low in the 1×25 mg cohort with none of the patients achieving PASI 90. Placebo response rates were 9.1% (2 of 22 patients) for PASI 75 and 4.5% (1 of 22 patients) for PASI 90. In the subgroup analyses (Table 9), the highest PASI 75 (93.8%) response was seen in patients treated with 3×150 mg and weighing less than 90 kg, whereas only 63.6% of patients weighing more than 90 kg achieved a PASI 75 in this cohort after 12 weeks of treatment.

TABLE 8

Number (%) of subjects achieving PASI 50, PASI 75, or PASI 90 by visit and treatment (full analysis set, LOCF).

| Visit | Criterion | 1 × 25 mg<br>N = 29<br>n (%) | 3 × 25 mg<br>N = 26<br>n (%) | 3 × 75 mg<br>N = 21<br>n (%) | 3 × 150 mg<br>N = 27<br>n % | Placebo<br>N = 22<br>n (%) |
|---|---|---|---|---|---|---|
| Week 2 | n evaluable | 29 | 26 | 21 | 27 | 22 |
|  | PASI 50 | 1 (3.4) | 2 (7.7) | 1 (4.8) | 3 (11.1) | 0 (0.0) |
|  | PASI 75 | 0 (0.0) | 0 (0.0) | 0 (0.0) | 0 (0.0) | 0 (0.0) |
|  | PASI 90 | 0 (0.0) | 0 (0.0) | 0 (0.0) | 0 (0.0) | 0 (0.0) |
| Week 3 | n evaluable | 29 | 26 | 21 | 27 | 22 |
|  | PASI 50 | 1 (3.4) | 2 (7.7) | 5 (23.8) | 5 (18.5) | 1 (4.5) |
|  | PASI 75 | 0 (0.0) | 0 (0.0) | 0 (0.0) | 0 (0.0) | 0 (0.0) |
|  | PASI 90 | 0 (0.0) | 0 (0.0) | 0 (0.0) | 0 (0.0) | 0 (0.0) |

TABLE 8-continued

Number (%) of subjects achieving PASI 50, PASI 75, or PASI 90 by visit and treatment (full analysis set, LOCF).

| Visit | Criterion | 1 × 25 mg N = 29 n (%) | 3 × 25 mg N = 26 n (%) | 3 × 75 mg N = 21 n (%) | 3 × 150 mg N = 27 n % | Placebo N = 22 n (%) |
|---|---|---|---|---|---|---|
| Week 5 | n evaluable | 29 | 26 | 21 | 27 | 22 |
|  | PASI 50 | 3 (10.3) | 4 (15.4) | 6 (28.6) | 13 (48.1) | 1 (4.5) |
|  | PASI 75 | 0 (0.0) | 2 (7.7) | 1 (4.8) | 4 (14.8) | 1 (4.5) |
|  | PASI 90 | 0 (0.0) | 0 (0.0) | 0 (0.0) | 1 (3.7) | 0 (0.0) |
| Week 9 | n evaluable | 29 | 26 | 21 | 27 | 22 |
|  | PASI 50 | 3 (10.3) | 10 (38.5) | 11 (52.4) | 23 (85.2) | 3 (13.6) |
|  | PASI 75 | 1 (3.4) | 3 (11.5) | 7 (33.3) | 18 (66.7) | 2 (9.1) |
|  | PASI 90 | 0 (0.0) | 1 (3.8) | 2 (9.5) | 4 (14.8) | 0 (0.0) |
| Week 13 | n evaluable | 29 | 26 | 21 | 27 | 22 |
|  | PASI 50 | 5 (17.2) | 15 (57.7) | 17 (81.0) | 23 (85.2) | 4 (18.2) |
|  | PASI 75 | 1 (3.4) | 5 (19.2) | 12 (57.1) | 22 (81.5) | 2 (9.1) |
|  | PASI 90 | 0 (0.0) | 2 (7.7) | 4 (19.0) | 14 (51.9) | 1 (4.5) |

Percentages are based on the number of subjects with evaluable data (n evaluable).

TABLE 9

Subgroup analysis: Number (%) of subjects achieving PASI 75 at Week 13, by treatment, by body weight group (full analysis set, LOCF).

| Subgroup Weight stratum | Criterion | 1 × 25 mg N = 29 n (%) | 3 × 25 mg N = 26 n (%) | 3 × 75 mg N = 21 n (%) | 3 × 150 mg N = 27 n (%) | Placebo N = 22 n (%) |
|---|---|---|---|---|---|---|
| All patients |  |  |  |  |  |  |
| Overall | n evaluable | 29 | 26 | 21 | 27 | 22 |
|  | PASI 75 achievement | 1 (3.4) | 5 (19.2) | 12 (57.1) | 22 (81.5) | 2 (9.1) |
| <90 kg | n evaluable | 16 | 13 | 12 | 16 | 10 |
|  | PASI 75 achievement | 1 (6.3) | 5 (38.5) | 7 (58.3) | 15 (93.8) | 2 (20.0) |
| >=90 kg | n evaluable | 13 | 13 | 9 | 11 | 12 |
|  | PASI 75 achievement | 0 (0.0) | 0 (0.0) | 5 (55.6) | 7 (63.6) | 0 (0.0) |

Discussion and Analysis

The results of this 12 week dose finding study further confirm the efficacy of secukinumab in chronic plaque-type psoriasis. Secukinumab 150 mg given s.c. monthly for 3 doses resulted in PASI 75 and PASI 90 response rates of 81.5% and 51.9%, respectively (Table 8). These response rates were higher than those observed in the highest response cohort in study A2211, the "Early" arm, where patients received 4× secukinumab 150 mg s.c. (at Baseline, Week 1, Week 2, and Week 4).

The data from the primary endpoint analysis of this study clearly imply that the clinical effect of a single injection of secukinumab 25 mg s.c. is similar to placebo. Although responses in the 3×25 mg cohort are numerically slightly higher than placebo, they show no statistical significance vs. placebo. Both the 3×75 mg and the 3×150 mg cohorts show good PASI 75 responses. However, only the 3×150 mg cohort achieves PASI 90 responses in excess of 50% at 12 weeks.

As has been observed in some of the dosing regimens for study CAIN457A2211, there is an effect of body weight on response to treatment, with subjects weighing less than 90 kg having markedly higher PASI 75 response rates (Table 9). Although this effect of weight is seen in most dose cohorts, the difference in response between patients <90 kg vs. ≥90 kg in the 1×25 mg and 3×25 mg is not much different from placebo. This is further indication that these low doses offer no clinically meaningful benefit.

In summary, CAIN457A2220 achieved the objective of defining non-effective dose regimens of secukinumab (lx 25 mg, and 3×25 mg) in psoriasis and demonstrates that in order to attain a good PASI 75 response at Week 12, at least 3×150 mg is required. As seen in other trials of secukinumab in psoriasis, this study confirmed that there was an effect of body weight on clinical response rates using the dose regimens assessed.

Example 4

Modelling and Simulation—Improved Induction and Maintenance Regimens

Example 4.3

Modeling Studies

The relationship between secukinumab dose/regimen, secukinumab plasma concentration and the PASI response relationship has been modeled using a population-PK/PD approach. The model has been built incrementally built and updated based on data from the studies CAIN457A2102, CAIN457A2103, CAIN457A2211, CAIN457A2212, and CAIN457A2220.

Studies CAIN457A2102 and CAIN457A2212 are described in Example 1; study CAIN457A2211 is described in Example 2. Study CAIN457A2220 is described in Example 3. Study CAIN457A2103 assessed the absolute bioavailability of secukinumab after subcutaneous administration. Fourteen patients with moderate to severe chronic plaque-type psoriasis were randomized to receive either a subcutaneous (150 mg, n=7) or intravenous (1 mg/kg, n=7) administration of secukinumab at day 1. The second study drug administration at day 29 occurred via the reversed route. Patients were followed up for 12 weeks after last dose. Local tolerability of subcutaneously administered secukinumab was excellent with no evidence of patient reported pain, or physician reported injection site reactions. Bioavailability of subcutaneously administered secukinumab was approximately 60% compared to the intravenous administration. The results supported the subcutaneous administration of secukinumab.

Concentration profiles of secukinumab are described by a two-compartment model, with combined first-order absorption to reflect subcutaneous administration and zero-order absorption to reflect intravenous administration. PASI profiles are characterized by a turnover (indirect response) model. The drug effect acts on the turnover model via an Emax-function, driven by secukinumab concentration in the central compartment. Inter-individual variability is estimated as a random effect on PK parameters (clearance, volume of distribution, inter-compartmental clearance, volume of distribution of peripheral compartment, bioavailability, and absorption rate), and PD parameters (turnover out-rate kout, PASI steady state level, and $EC_{50}$).

Based on this model and the final parameter estimates, simulations were run to predict the expected outcome for the proposed dosing regimen. Uncertainty of fixed effects, as well as random effects variance parameters is taken into account, by sampling new parameter sets per simulation replicate. Model-validation was performed using standard assessment methods (goodness-of-fit analysis, predictive checks, and external validation based on prospective predictions).

Example 4.3

Results of Modeling Studies

While 300 mg secukinumab s.c. was not tested in the phase II studies in psoriasis (although it was tested in rheumatoid arthritis), patients were exposed to higher doses (up to 3×10 mg/kg i.v.) in the psoriasis study CAIN457A2212. As FIG. 8 demonstrates, the proposed loading regimen with 150 mg and 300 mg s.c. will lead to a lower exposure compared to study CAIN457A2212. More specifically, the proposed dose regimen of 300 mg s.c. delivers a similar exposure profile to 10 mg/kg i.v. while avoiding high exposure peaks, and is projected to lead to PASI 75 response rates similar to those seen with 10 mg/kg i.v. Thus, CAIN457A2304 proceeds with s.c. loading regimens using 150 mg and 300 mg doses.

The proposed induction regimen is supported by additional model-based analyses using data from four psoriasis studies (CAIN457A2102, CAIN457A2211, CAIN457A2212, and CAIN457A2220). As seen in FIG. 9, the proposed induction regimen (weekly for five weeks during weeks 1, 2, 3, 4, and 5, followed by an additional induction dose at week 9) is predicted to deliver a notably better PASI 75 response rate after twelve weeks of treatment when compared to the response rates observed in study CAIN457A2211. The predicted efficacy of a 75 mg dose regimen depicted in FIG. 9 is not ideal.

The proposed maintenance regimen is also supported by model-based analyses. Fixed treatment intervals of four, eight and twelve weeks have been simulated for the 150 mg dose, with the results shown in FIG. 10. It can be seen that only the four week interval effectively maintains a PASI 75 response in most patients.

Example 5

Study CAIN457A2304

Study CAIN457A2304 is planned to be a randomized, double-blind, multicenter study of subcutaneous secukinumab, in either a fixed-interval or a treatment-at-start-of-relapse maintenance regimen, to demonstrate the efficacy on Psoriasis Area and Severity Index (PAST) and on Investigator's Global Assessment (IGA) score and to assess the safety and tolerability up to one year in patients with moderate to severe chronic plaque-type psoriasis.

After a screening period of up to four weeks, about 918 patients will be randomized to receive secukinumab in one of two different doses (150 mg or 300 mg). Secukinumab will be administered at Weeks 0, 1, 2, 3, 4, and 8 during the induction phase. At the end of the induction phase, patients who have shown a PASI 75 response after twelve weeks of treatment will be randomized to either receive secukinumab every four weeks (two different doses i.e. 150 mg or 300 mg), starting at Week 12, and up until Week 48 (for an overall treatment duration of 52 weeks); or to receive secukinumab in an individualized treatment regimen. In the individualized regimen, patients will only receive secukinumab when they suffer from a start of relapse (defined as a loss of at least 20% of the maximal PASI gain achieved previously, and a loss of PASI 75 response); they will then continue to receive secukinumab every four weeks until they have achieved a PASI 75 response, after which they will go off treatment again. The individual doses will be equivalent to the doses the patients had received and responded to during the induction period (i.e. 150 mg or 300 mg). A graphical illustration of the study is shown in FIG. 11.

As the primary objective of this study CAIN457A2304 is to compare two different maintenance regimens, and as only very few placebo patients would be expected to enter the maintenance part of the study (i.e. beyond the first twelve weeks of treatment), the study does not contain a placebo group. After the end of the maintenance treatment period, patients will be eligible to enter the extension trial CAIN457A2304E1, or enter a follow-up period of twelve weeks after last study drug administration.

The extension study of CAIN457A2304 (CAIN457A2304E1) is planned to be a randomized, double-blind, multicenter study of subcutaneous secukinumab, in either a fixed-interval or a treatment-at-start-of-relapse maintenance regimen, to demonstrate the efficacy on Psoriasis Area and Severity Index (PAST) and on Investigator's Global Assessment (IGA) score and to assess the safety and tolerability for an additional year in patients with moderate to severe chronic plaque-type psoriasis.

Patients who have participated in study CAIN457A2304 and have completed the maintenance treatment period of the respective study will be eligible to enter this extension trial. Patients will remain on the dose (i.e. either 150 mg or 300 mg of secukinumab) and regimen (i.e. either "dosing at fixed intervals" or "dosing at start of relapse") that they received during the core study. The treatment duration of the extension study is currently planned to be at least 52 weeks.

Example 6

Pharmokinetic (PK) Information for Seckukinumab

Based on data obtained from various studies, including those discussed in the above Examples, the following PK information is provided for seckukinumab (Table 10).

TABLE 10

Pharmokinetic values for secukinumab. Experimental PK values are compiled from various secukinumab psoriasis trials. Simulated values are provided for the indicated psoriasis dosing regimens.

| | |
|---|---|
| Experimental | Induction mean trough level one month after a 4$^{th}$ dose of 150 mg delivered s.c. at weeks 0, 1, 2 and 4 ~29.2 μg/mL, with a 30-40% inter-patient variation<br>Maintenance average steady-state trough levels ~15 μg/ml (for a monthly 150 mg regimen), with a 30-40% inter-patient variation |
| Simulated | Induction (150 or 300 mg delivered s.c. weeks 0, 1, 2, 3, 4, and 8) C$_{max}$ (around 32 days) for a typical 90 kg patient:<br>~52 μg/ml (for 150 mg regimen)<br>~104 μg/ml (for 300 mg regimen)<br>Maintenance (150 or 300 mg delivered s.c. monthly beginning week 12) Average steady-state trough levels for a typical 90 kg psoriasis patient:<br>~16 μg/ml (for a monthly 150 mg regimen)<br>~33 μg/ml (for a monthly 300 mg regimen)<br>95% of the population are predicted to be in the range:<br>5-33 μg/ml (for a monthly 150 mg regimen)<br>11-70 μg/ml (for a monthly 300 mg regimen) |

In addition, it has been determined that secukinumab has a $T_{max}$ of about 7-8 days, and an elimination half-life of about 30 days. The PK information provided in this Example can be used to design different dosing regimens for treatment of psoriasis at SoR, e.g., delivery of a different dosage of the IL-17 binding molecule (e.g., an IL-17 antibody, e.g., secukinumab) from the dosage used in the Examples or delivery of the same dosage as used in the Examples, but which is provided at a different time point from the time points used in the Examples. By maintaining the same PK profile, even though a dosing regimen may change, a skilled artisan is expected to be able to use an IL-17 binding molecule (e.g., an IL-17 antibody, e.g., secukinumab) for treatment of psoriasis, including treatment of psoriasis at SoR.

What is claimed is:

1. A method of treating psoriasis, comprising subcutaneously administering to a patient in need thereof about 150 mg-about 300 mg of an IL-17 antibody weekly during week 0, 1, 2, 3, and 4, and then monthly thereafter, wherein the IL-17 antibody comprises:
   i) an immunoglobulin $V_H$ domain comprising the amino acid sequence set forth as SEQ ID NO:8 and an immunoglobulin $V_L$ domain comprising the amino acid sequence set forth as SEQ ID NO:10;
   ii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6;
   iii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6; or
   iv) secukinumab.

2. The method of claim 1, wherein about 150 mg or about 300 mg of the IL-17 antibody is administered to the patient.

3. The method of claim 2, wherein about 300 mg of the IL-17 antibody is administered to the patient.

4. The method of claim 3, wherein the patient has plaque psoriasis.

5. The method of claim 4, wherein the patient has moderate to severe plaque psoriasis.

6. The method of claim 3, wherein the IL-17 antibody is secukinumab.

7. The method according to claim 1, wherein, prior to treatment with the IL-17 antibody, the patient has not been previously treated with a systemic agent for psoriasis.

8. The method according to claim 1, wherein, prior to treatment with the IL-17 antibody, the patient has been previously treated with a systemic agent for psoriasis.

9. The method according to claim 8, wherein the systemic agent is selected from the group consisting of methotrexate, cyclosporine, fumaric acid esters, acitretin, alefacept, adalimumab, efalizumab, etanercept, infliximab, golimumab and ustekinumab.

10. The method according to claim 8, wherein the systemic agent is methotrexate.

11. A method of treating psoriasis, comprising administering to a patient having moderate to severe plaque psoriasis about 300 mg of secukinumab by subcutaneous injection at weeks 0, 1, 2, 3, and 4, followed by about 300 mg every four weeks.

12. A method of treating psoriasis, comprising administering to a patient having moderate to severe plaque psoriasis about 150 mg of secukinumab by subcutaneous injection at weeks 0, 1, 2, 3, and 4, followed by about 150 mg every four weeks.

13. A method of treating moderate to severe plaque psoriasis in an adult patient who is a candidate for systemic therapy or phototherapy, comprising administering to the patient 300 mg of secukinumab by subcutaneous injection at weeks 0, 1, 2, 3, and 4, followed by 300 mg of secukinumab by subcutaneous injection every four weeks.

14. A method of treating moderate to severe plaque psoriasis in an adult patient who is a candidate for systemic therapy or phototherapy, comprising administering to the patient 150 mg of secukinumab by subcutaneous injection at weeks 0, 1, 2, 3, and 4, followed by 150 mg of secukinumab by subcutaneous injection every four weeks.

\* \* \* \* \*

UNITED STATES PATENT AND TRADEMARK OFFICE
CERTIFICATE OF CORRECTION

| | | |
|---|---|---|
| PATENT NO. | : 9,717,791 B2 | Page 1 of 1 |
| APPLICATION NO. | : 13/876367 | |
| DATED | : August 1, 2017 | |
| INVENTOR(S) | : Guettner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this
Eighteenth Day of December, 2018

Andrei Iancu
*Director of the United States Patent and Trademark Office*

```
SEQUENCE LISTING

<160> NUMBER OF SEQ ID NOS: 17

<210> SEQ ID NO 1
<211> LENGTH: 5
<212> TYPE: PRT
<213> ORGANISM: artificial
<220> FEATURE:
<223> OTHER INFORMATION: CDR1 = hypervariable region 1 of heavy chain
      of AIN457

<400> SEQUENCE: 1

Asn Tyr Trp Met Asn
1               5

<210> SEQ ID NO 2
<211> LENGTH: 17
<212> TYPE: PRT
<213> ORGANISM: ARTIFICIAL
<220> FEATURE:
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
```

```
<211> LENGTH: 12
<212> TYPE: PRT
<213> ORGANISM: ARTIFICIAL
<220> FEATURE:
<223> OTHER INFORMATION: CDR1' = hypervariable region 1 of light chain of
      AIN457

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: ARTIFICIAL
<220> FEATURE:
<223> OTHER INFORMATION: CDR3' = hypervariable region 3 of light chain
      AIN457

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7 gag gtg cag ttg gtg gag tct ggg gga ggc ttg gtc cag cct ggg ggg         48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt aac tat         96
Ser Leu Arg Leu Ser Cys Ala Ala Ser Gly Phe Thr Phe Ser Asn Tyr
            20                  25                  30 tgg atg aac tgg gtc cgc cag gct cca ggg aaa ggg ctg gag tgg gtg        144
Trp Met Asn Trp Val Arg Gln Ala Pro Gly Lys Gly Leu Glu Trp Val
        35                  40                  45 gcc gcc ata aac caa gat gga agt gag aaa tac tat gtg ggc tct gtg        192
Ala Ala Ile Asn Gln Asp Gly Ser Glu Lys Tyr Tyr Val Gly Ser Val
    50                  55                  60 aag ggc cga ttc acc atc tcc aga gac aac gcc aag aac tca ctg tat        240
Lys Gly Arg Phe Thr Ile Ser Arg Asp Asn Ala Lys Asn Ser Leu Tyr
65                  70                  75                  80 ctg caa atg aac agc ctg aga gtc gag gac acg gct gtg tat tac tgt        288
Leu Gln Met Asn Ser Leu Arg Val Glu Asp Thr Ala Val Tyr Tyr Cys
                85                  90                  95 gtg agg gac tat tac gat att ttg acc gat tat tac atc cac tat tgg        336
Val Arg Asp Tyr Tyr Asp Ile Leu Thr Asp Tyr Tyr Ile His Tyr Trp
                100                 105                 110
```

```
tac ttc gat ctc tgg ggc cgt ggc acc ctg gtc act gtc tcc tca          381
Tyr Phe Asp Leu Trp Gly Arg Gly Thr Leu Val Thr Val Ser Ser
            115                 120                 125
```

<210> SEQ ID NO 8
<211> LENGTH: 127
<212> TYPE: PRT
<213> ORGANISM: HOMO SAPIENS

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125
```

<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9

```
gaa att gtg ttg acg cag tct cca ggc acc ctg tct ttg tct cca ggg           48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc           96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc          144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt          192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag          240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg          288
Pro Glu Asp Phe Ala Val Tyr Tyr Cys Gln Gln Tyr Gly Ser Ser Pro
                85                  90                  95 tgc acc ttc ggc caa ggg aca cga ctg gag att aaa cga                      327
Cys Thr Phe Gly Gln Gly Thr Arg Leu Glu Ile Lys Arg
            100                 105
```

<210> SEQ ID NO 10
<211> LENGTH: 109
<212> TYPE: PRT

<213> ORGANISM: HOMO SAPIENS

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105

<210> SEQ ID NO 11
<211> LENGTH: 10
<212> TYPE: PRT
<213> ORGANISM: artificial
<220> FEATURE:
<223> OTHER INFORMATION: CDR1-x = hypervariable domain x of heavy chain
      of AIN457

<400> SEQUENCE: 11

Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 711
<212> TYPE: DNA
<213> ORGANISM: homo sapiens
<220> FEATURE:
<221> NAME/KEY: CDS
<222> LOCATION: (1)..(708)

```
<400> SEQUENCE: 14 acc atg gaa acc cca gcg gag ctt ctc ttc ctc ctg cta ctc tgg ctc      48
Thr Met Glu Thr Pro Ala Glu Leu Leu Phe Leu Leu Leu Leu Trp Leu
1               5                   10                  15 cca gat acc acc gga gaa att gtg ttg acg cag tct cca ggc acc ctg      96
Pro Asp Thr Thr Gly Glu Ile Val Leu Thr Gln Ser Pro Gly Thr Leu
            20                  25                  30 tct ttg tct cca ggg gaa aga gcc acc ctc tcc tgc agg gcc agt cag     144
Ser Leu Ser Pro Gly Glu Arg Ala Thr Leu Ser Cys Arg Ala Ser Gln
        35                  40                  45 agt gtt agc agc agc tac tta gcc tgg tac cag cag aaa cct ggc cag     192
Ser Val Ser Ser Ser Tyr Leu Ala Trp Tyr Gln Gln Lys Pro Gly Gln
    50                  55                  60 gct ccc agg ctc ctc atc tat ggt gca tcc agc agg gcc act ggc atc     240
Ala Pro Arg Leu Leu Ile Tyr Gly Ala Ser Ser Arg Ala Thr Gly Ile
65                  70                  75                  80 cca gac agg ttc agt ggc agt ggg tct ggg aca gac ttc act ctc acc     288
Pro Asp Arg Phe Ser Gly Ser Gly Ser Gly Thr Asp Phe Thr Leu Thr
                85                  90                  95 atc agc aga ctg gag cct gaa gat ttt gca gtg tat tac tgt cag cag     336
Ile Ser Arg Leu Glu Pro Glu Asp Phe Ala Val Tyr Tyr Cys Gln Gln
            100                 105                 110 tat ggt agc tca ccg tgc acc ttc ggc caa ggg aca cga ctg gag att     384
Tyr Gly Ser Ser Pro Cys Thr Phe Gly Gln Gly Thr Arg Leu Glu Ile
        115                 120                 125 aaa cga act gtg gct gca cca tct gtc ttc atc ttc ccg cca tct gat     432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc     528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac     576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac     624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc     672
Glu Lys His Lys Val Tyr Ala Cys Glu Val Thr His Gln Gly Leu Ser
    210                 215                 220 tcg ccc gtc aca aag agc ttc aac agg gga gag tgt tag                  711
Ser Pro Val Thr Lys Ser Phe Asn Arg Gly Glu Cys
225                 230                 235

<210> SEQ ID NO 15
<211> LENGTH: 236
<212> TYPE: PRT
<213> ORGANISM: homo sapiens

<400> SEQUENCE: 15

Thr Met Glu Thr Pro Ala Glu Leu Leu Phe Leu Leu Leu Leu Trp Leu
1               5                   10                  15

Pro Asp Thr Thr Gly Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45
```

```
Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
                100                 105                 110

Tyr Gly Ser Ser Pro Cys Thr Phe Gly Gln Gly Thr Arg Leu Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 16
<211> LENGTH: 783
<212> TYPE: DNA
<213> ORGANISM: homo sapiens
<220> FEATURE:
<221> NAME/KEY: CDS
<222> LOCATION: (1)..(780)

<400> SEQUENCE: 16 acc atg gaa ttg ggg ctg agc tgg gtt ttc ctt gtt gct att tta gaa      48
Thr Met Glu Leu Gly Leu Ser Trp Val Phe Leu Val Ala Ile Leu Glu
1               5                   10                  15 ggt gtc cac tgt gag gtg cag ttg gtg gag tct ggg gga ggc ttg gtc      96
Gly Val His Cys Glu Val Gln Leu Val Glu Ser Gly Gly Gly Leu Val
                20                  25                  30 cag cct ggg ggg tcc ctg aga ctc tcc tgt gca gcc tct gga ttc acc     144
Gln Pro Gly Gly Ser Leu Arg Leu Ser Cys Ala Ala Ser Gly Phe Thr
            35                  40                  45 ttt agt aac tat tgg atg aac tgg gtc cgc cag gct cca ggg aaa ggg     192
Phe Ser Asn Tyr Trp Met Asn Trp Val Arg Gln Ala Pro Gly Lys Gly
        50                  55                  60 ctg gag tgg gtg gcc gcc ata aac caa gat gga agt gag aaa tac tat     240
Leu Glu Trp Val Ala Ala Ile Asn Gln Asp Gly Ser Glu Lys Tyr Tyr
65                  70                  75                  80 gtg ggc tct gtg aag ggc cga ttc acc atc tcc aga gac aac gcc aag     288
Val Gly Ser Val Lys Gly Arg Phe Thr Ile Ser Arg Asp Asn Ala Lys
                85                  90                  95 aac tca ctg tat ctg caa atg aac agc ctg aga gtc gag gac acg gct     336
Asn Ser Leu Tyr Leu Gln Met Asn Ser Leu Arg Val Glu Asp Thr Ala
                100                 105                 110 gtg tat tac tgt gtg agg gac tat tac gat att ttg acc gat tat tac     384
Val Tyr Tyr Cys Val Arg Asp Tyr Tyr Asp Ile Leu Thr Asp Tyr Tyr
            115                 120                 125
```

| | | | | | | | | | | | | | | | | |
|---|---|---|---|---|---|---|---|---|---|---|---|---|---|---|---|---|
| atc | cac | tat | tgg | tac | ttc | gat | ctc | tgg | ggc | cgt | ggc | acc | ctg | gtc | act | 432 |
| Ile | His | Tyr | Trp | Tyr | Phe | Asp | Leu | Trp | Gly | Arg | Gly | Thr | Leu | Val | Thr | |
| | 130 | | | | 135 | | | | | 140 | | | | | | |
| gtc | tcc | tca | gcc | tcc | acc | aag | ggc | cca | tcg | gtc | ttc | ccc | ctg | gca | ccc | 480 |
| Val | Ser | Ser | Ala | Ser | Thr | Lys | Gly | Pro | Ser | Val | Phe | Pro | Leu | Ala | Pro | |
| 145 | | | | | 150 | | | | | 155 | | | | | 160 | |
| tcc | tcc | aag | agc | acc | tct | ggg | ggc | aca | gcg | gcc | ctg | ggc | tgc | ctg | gtc | 528 |
| Ser | Ser | Lys | Ser | Thr | Ser | Gly | Gly | Thr | Ala | Ala | Leu | Gly | Cys | Leu | Val | |
| | | | | 165 | | | | | 170 | | | | | 175 | | |
| aag | gac | tac | ttc | ccc | gaa | ccg | gtg | acg | gtg | tcg | tgg | aac | tca | ggc | gcc | 576 |
| Lys | Asp | Tyr | Phe | Pro | Glu | Pro | Val | Thr | Val | Ser | Trp | Asn | Ser | Gly | Ala | |
| | | | 180 | | | | | 185 | | | | | 190 | | | |
| ctg | acc | agc | ggc | gtg | cac | acc | ttc | ccg | gct | gtc | cta | cag | tcc | tca | gga | 624 |
| Leu | Thr | Ser | Gly | Val | His | Thr | Phe | Pro | Ala | Val | Leu | Gln | Ser | Ser | Gly | |
| | | 195 | | | | | 200 | | | | | 205 | | | | |
| ctc | tac | tcc | ctc | agc | agc | gtg | gtg | acc | gtg | ccc | tcc | agc | agc | ttg | ggc | 672 |
| Leu | Tyr | Ser | Leu | Ser | Ser | Val | Val | Thr | Val | Pro | Ser | Ser | Ser | Leu | Gly | |
| | 210 | | | | | 215 | | | | | 220 | | | | | |
| acc | cag | acc | tac | atc | tgc | aac | gtg | aat | cac | aag | ccc | agc | aac | acc | aag | 720 |
| Thr | Gln | Thr | Tyr | Ile | Cys | Asn | Val | Asn | His | Lys | Pro | Ser | Asn | Thr | Lys | |
| 225 | | | | | 230 | | | | | 235 | | | | | 240 | |
| gtg | gac | aag | aga | gtt | gag | ccc | aaa | tct | tgt | gac | aaa | act | cac | aca | tgc | 768 |
| Val | Asp | Lys | Arg | Val | Glu | Pro | Lys | Ser | Cys | Asp | Lys | Thr | His | Thr | Cys | |
| | | | | 245 | | | | | 250 | | | | | 255 | | |
| cca | ccg | tgc | cca | taa | | | | | | | | | | | | 783 |
| Pro | Pro | Cys | Pro | | | | | | | | | | | | | |
| | | | 260 | | | | | | | | | | | | | |

<210> SEQ ID NO 17
<211> LENGTH: 260
<212> TYPE: PRT
<213> ORGANISM: homo sapiens

<400> SEQUENCE: 17

Thr Met Glu Leu Gly Leu Ser Trp Val Phe Leu Val Ala Ile Leu Glu
1               5                   10                  15

Gly Val His Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Trp Met Asn Trp Val Arg Gln Ala Pro Gly Lys Gly
    50                  55                  60

Leu Glu Trp Val Ala Ala Ile Asn Gln Asp Gly Ser Glu Lys Tyr Tyr
65                  70                  75                  80

Val Gly Ser Val Lys Gly Arg Phe Thr Ile Ser Arg Asp Asn Ala Lys
                85                  90                  95

Asn Ser Leu Tyr Leu Gln Met Asn Ser Leu Arg Val Glu Asp Thr Ala
            100                 105                 110

Val Tyr Tyr Cys Val Arg Asp Tyr Tyr Asp Ile Leu Thr Asp Tyr Tyr
        115                 120                 125

Ile His Tyr Trp Tyr Phe Asp Leu Trp Gly Arg Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

```
Leu Thr Ser Gly Val His Thr Phe Pro Ala Val Leu Gln Ser Ser Gly
        195             200             205
Leu Tyr Ser Leu Ser Ser Val Val Thr Val Pro Ser Ser Ser Leu Gly
        210             215             220
Thr Gln Thr Tyr Ile Cys Asn Val Asn His Lys Pro Ser Asn Thr Lys
225             230             235             240
Val Asp Lys Arg Val Glu Pro Lys Ser Cys Asp Lys Thr His Thr Cys
            245             250             255
Pro Pro Cys Pro
            260
```